United States Patent [19]

Ueda et al.

[11] Patent Number: 5,028,531

[45] Date of Patent: * Jul. 2, 1991

[54] IGF-I FUSION PROTEINS; PROTECTION OF IGF-I FROM DEGRADATION BY HOST CELL; AND PROCESSES FOR THE PRODUCTION THEREOF

[75] Inventors: Ikuo Ueda, Toyonaka; Mineo Niwa, Mukoo; Yoshimasa Saitoh; Susumu Satoh, both of Osaka; Chihiro Kusunoki, Suita; Tadashi Kitaguchi, Amagasaki; Hiroki Ono, Osaka, all of Japan

[73] Assignee: Fujisawa Pharmaceutical Company, Ltd., Osaka, Japan

[*] Notice: The portion of the term of this patent subsequent to May 28, 2008 has been disclaimed.

[21] Appl. No.: 215,826

[22] Filed: Jul. 6, 1988

Related U.S. Application Data

[63] Continuation of Ser. No. 903,242, Sep. 3, 1986, abandoned, which is a continuation-in-part of Ser. No. 708,636, Mar. 6, 1985, abandoned.

[30] Foreign Application Priority Data

Mar. 19, 1984 [GB] United Kingdom ............... 8407044
Sep. 25, 1984 [GB] United Kingdom ............... 8424197
Sep. 17, 1985 [GB] United Kingdom ............... 8522977

[51] Int. Cl.$^5$ .............. C12N 15/00; C12N 15/17; C12N 15/20; C12N 15/70
[52] U.S. Cl. ................. 435/69.4; 435/72.3; 435/252.33; 435/320.1; 536/27; 935/47; 935/60; 935/10; 935/13
[58] Field of Search ............... 435/68, 70, 91, 253, 435/240.1, 317.1, 172.3, 320; 536/27; 935/12, 29, 32, 34, 56, 60; 530/302, 303, 350, 351, 324, 325, 326, 820; 514/2

[56] References Cited

U.S. PATENT DOCUMENTS 4,571,421 2/1986 Itakura .......................... 536/27
4,745,179 5/1988 Ueda et al. .................... 530/350

FOREIGN PATENT DOCUMENTS 0072925 8/1981 European Pat. Off. .
0036776 9/1981 European Pat. Off. .

OTHER PUBLICATIONS

Barr et al., (1983), Abst. ASBC Jun. 5-9, #434.
Jamser et al., (1983), Nature 306:609-611.
Rinder Knecht et al. (1978), J.B.C. 253:2769-2776.
Nilsson et al., Nucleic Acids Res. 13(4) 1151-1163.

Primary Examiner—Richard A. Schwartz
Assistant Examiner—S. L. Nolan
Attorney, Agent, or Firm—Oblon, Spivak, McClelland, Maier & Neustadt

[57] ABSTRACT

IGF-I fused with a protective peptide, in which the protective peptide is a protein peptide and is used for the protection of IGF-I from degradation by protease in cells of *E. coli* is disclosed. Also disclosed are genes coding for the fused IGF-I's, plasmids containing the genes, and *E. coli* microorganisms transformed with the plasmids.

8 Claims, 27 Drawing Sheets

FIG.2B

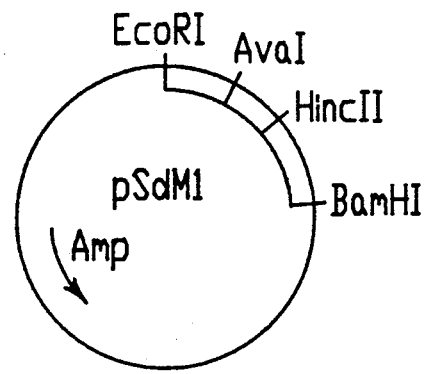
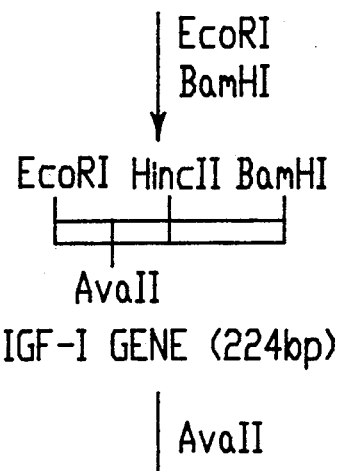
*FIG. 12A*
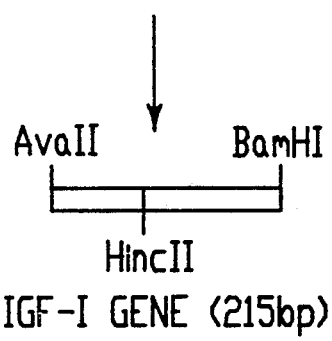
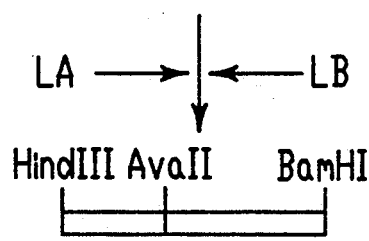
*FIG. 12B*

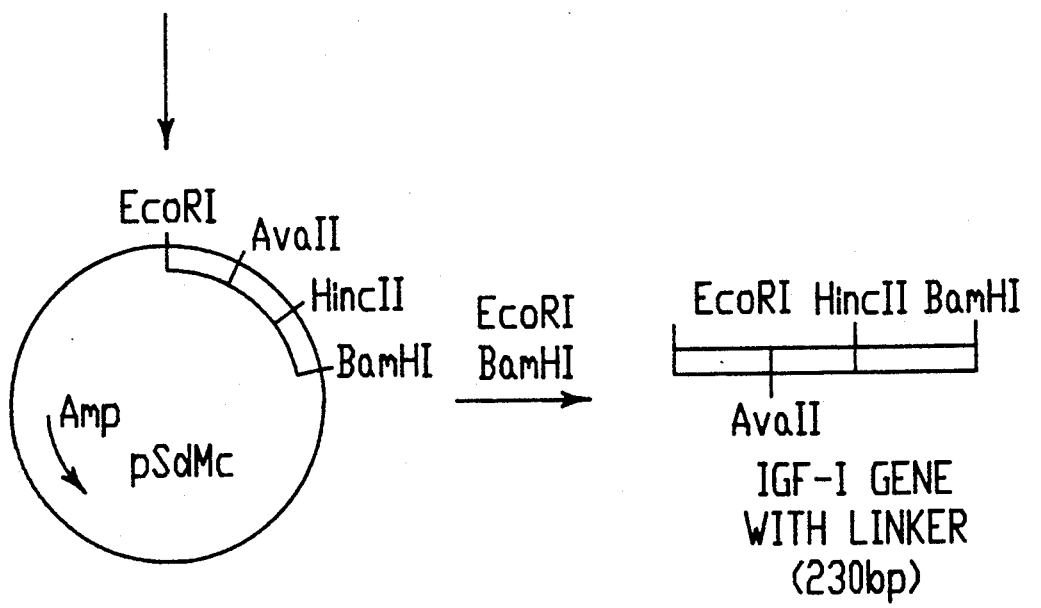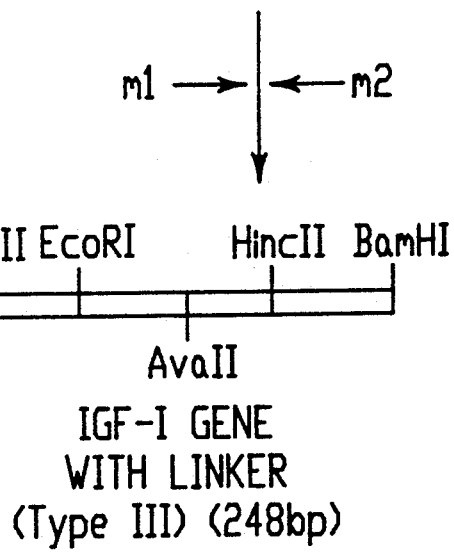
FIG. 13B

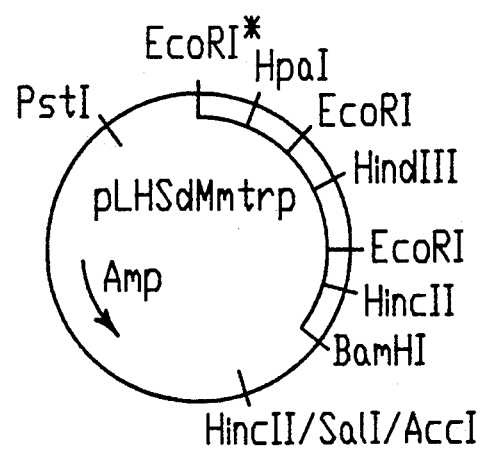
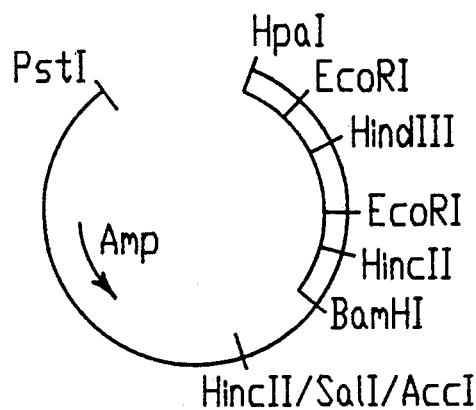
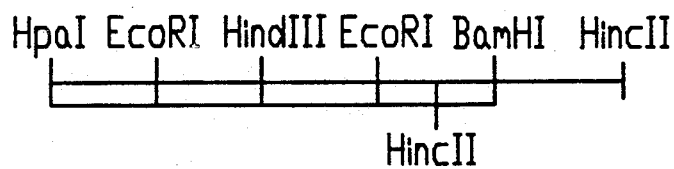
FIG. 14A

IGF-I FUSION PROTEINS; PROTECTION OF IGF-I FROM DEGRADATION BY HOST CELL; AND PROCESSES FOR THE PRODUCTION THEREOF

This is a continuation of application Ser. No. 06/903,242, filed Sept. 3, 1986, now abandoned, which is a continuation-in-part of application Ser. No. 708,636, filed Mar. 6, 1985, now abandoned.

SUMMARY OF THE INVENTION

This invention relates to processes for production of human insulin-like growth factor I (hereinafter referred to as IGF-I), to IGF-I fused with a protective peptide (hereinafter referred to as fused IGF-I), to a gene coding for IGF-I (hereinafter referred to as IGF-I gene), to a gene coding for fused IGF-I (hereinafter referred to as fused IGF-I gene), to a plasmid containing a IGF-I gene, to a plasmid containing fused IGF-I gene(s), to a host organism containing plasmid containing IGF-I gene, to a host organism containing plasmid containing fused IGF-I gene(s), and to processes for the production thereof.

DISCUSSION OF THE BACKGROUND OF THE INVENTION

Figure 1A:
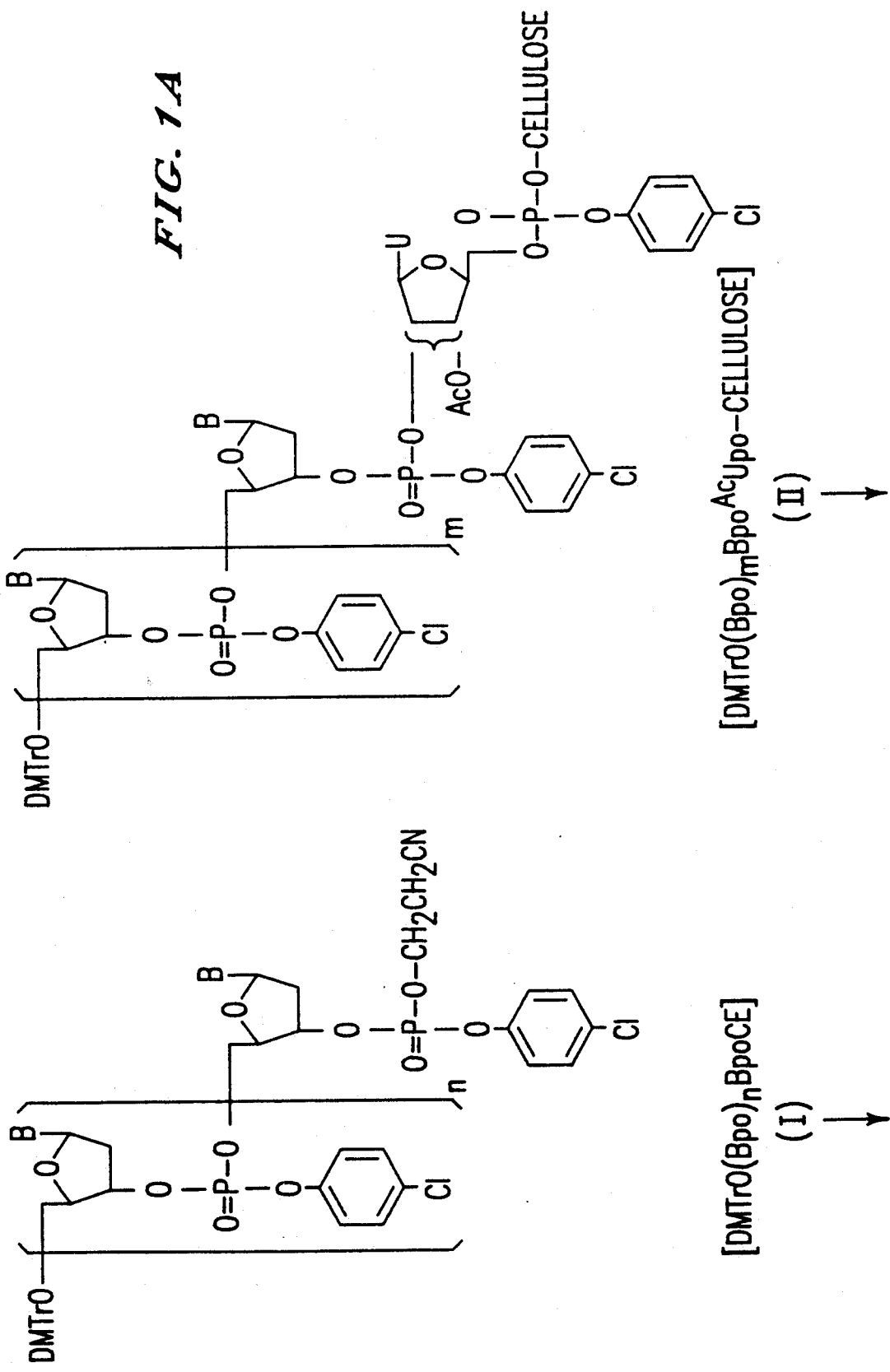
FIGS. 1A, B, C, & D illustrate preparing oligonucleotides from smaller units by successive coupling reactions.
Figure 1B:
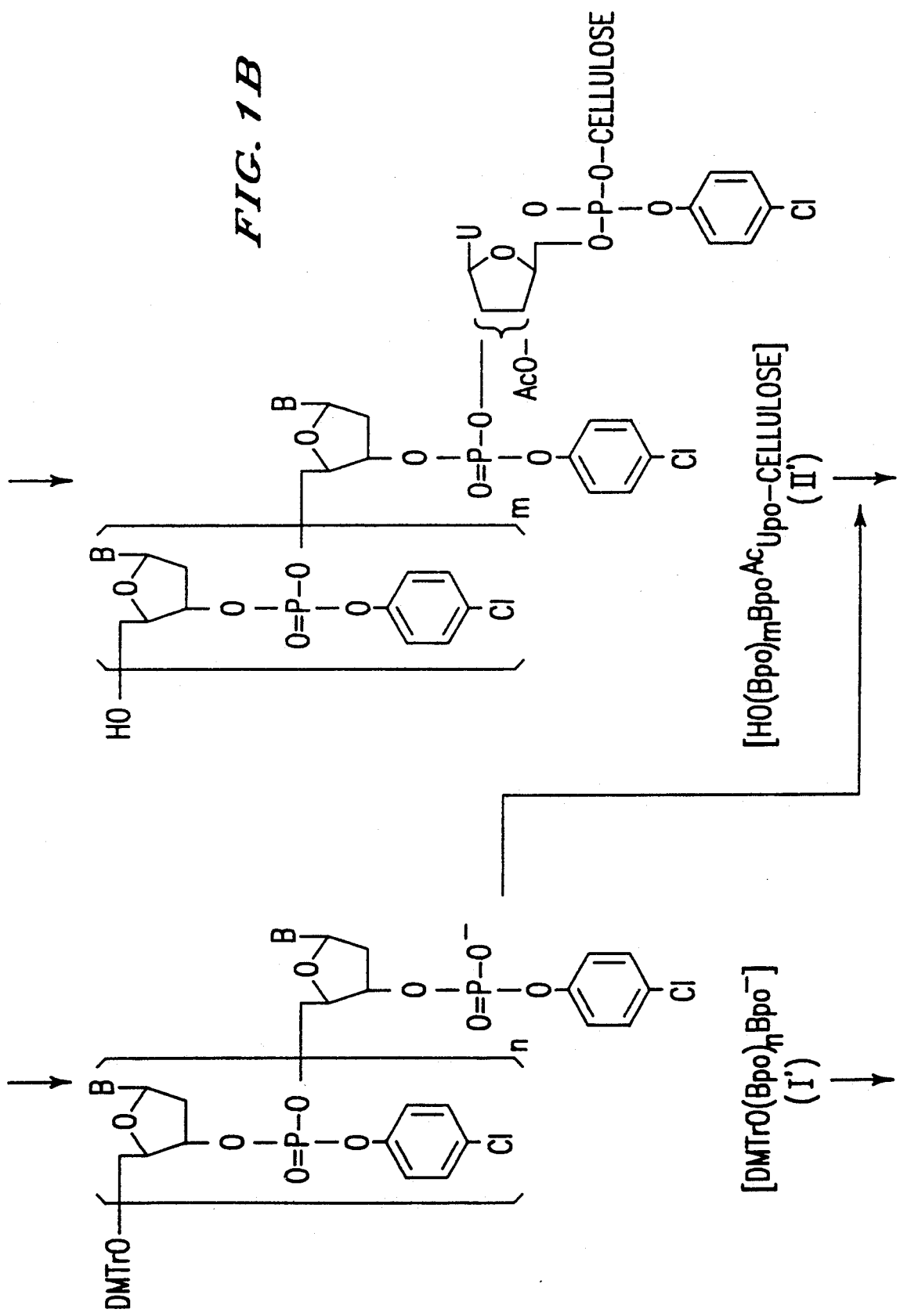
Figure 1C:
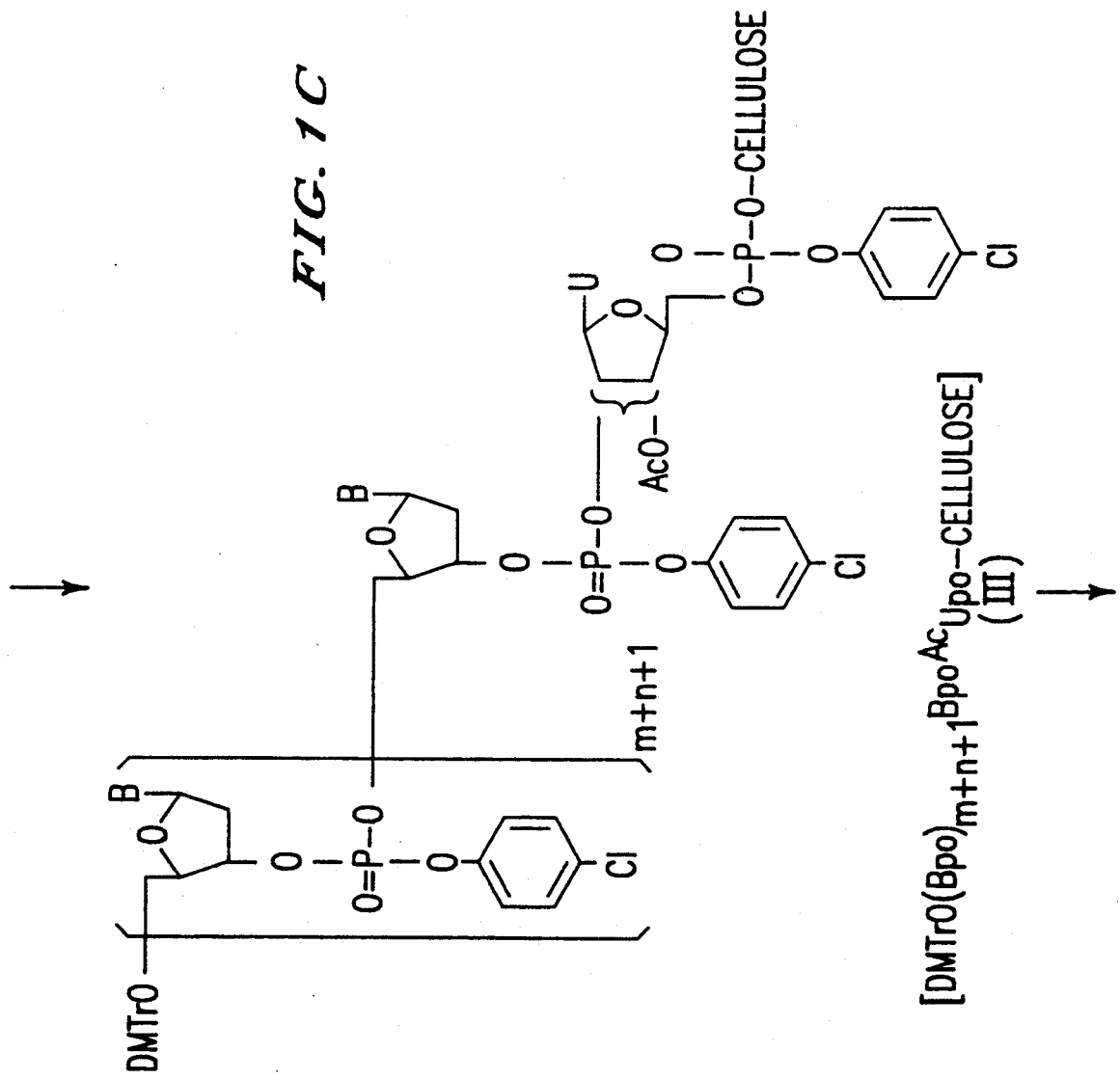
Figure 1D:
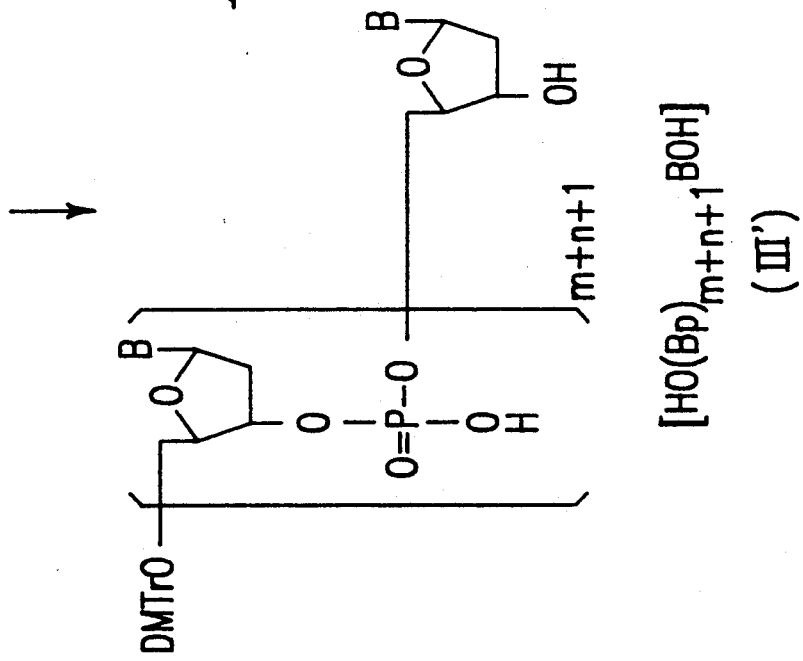

IGF-I is a protein hormone synthesized mainly in human tissues, liver and kidney when these are stimulated by a certain to hormone. IGF-I and is found in human serum.

IGF-I is known to (i) have insulin-like potency, (ii) stimulate the potency of sulfate-uptake by cartilage, and (iii) possibly enhance cellular protein and DNA synthesis.

Therefore, it is useful in promoter of growth and may be useful in clinical treatment of diabetes.

IGF-I is excreted in small amounts in human serum from which it can be isolated only at the rate of a few mgs of IGF-I per several tons of human serum. Additionally, the producing cell of IGF-I was isolated in pure form, and it was found that IGF-I had biological properties as mentioned above. The amino acid sequence of IGF-I has been reported in the literature.

There exists, however, a need for a more viable commercial production of IGF-I, and such a requirement stimulate the accomplishment of this invention.

DETAILED DESCRIPTION OF THE PREFERRED EMBODIMENTS

It was perceived that the application of recombinant DNA and associated technologies would be the most effective way of producing large quantities of IGF-I.

IGF-I is known to consist of the following sequence of 70 amino acids:

```
  1                                              10
Gly—Pro—Glu—Thr—Leu—Cys—Gly—Ala—Glu—Leu—Val—Asp—

20
Ala—Leu—Gln—Phe—Val—Cys—Gly—Asp—Arg—Gly—Phe—Tyr—Phe—

30
Asn—Lys—Pro—Thr—Gly—Tyr—Gly—Ser—Ser—Ser—Arg—Arg—Ala—

40                                         50
Pro—Gln—Thr—Gly—Ile—Val—Asp—Glu—Cys—Cys—Phe—Arg—Ser—

60
Cys—Asp—Leu—Arg—Arg—Leu—Glu—Met—Tyr—Cys—Ala—Pro—Leu—

70
Lys—Pro—Ala—Lys—Ser—Ala.
```

The inventors of this invention succeeded in producing a large amount of IGF-I by using the following essential steps.

Step 1

A process for the production of an IGF-I gene. This process is optionally followed by a process for the production of a fused IGF-I gene, which comprises linking a gene coding for a protective peptide with an IGF-I gene with or without a linker upstream of said IGF-I gene.

Suitable "linker" may include a gene coding for several amino acids and having a suitable restriction enzyme recognition sites to link a protective peptide upstream of an IGF-I gene, and the "linker" per se constructs said protective peptide.

The most suitable "linker" are the ones exemplified hereinafter.

Suitable "fused IGF-I" is the ones as illustrated and exemplified hereinafter in the Examples.

Step 2

A process for the production of an expression plasmid which comprises inserting a promoter gene and an IGF-I gene, or a promoter gene and a polycistronic or not non-polycistronic gene coding for fused IGF-I into a cloning plasmid.

The most suitable "expression plasmid" may include plasmid pSdM1-322trp, pLHSdMmtrp, pLHSdMwtrp, pLHSdMctrp, pLS-T2, pLS-T3 and the like.

The most suitable "cloning plasmid" may include pBR322 and the like.

Step 3

A process for the production of a transformant which comprises transforming a host organism with said expression plasmid.

Suitable "host organisms" may include *Escherichia* (hereinafter referred to as *E.*) *coli* (e. g. *E. coli* HB101, etc.) and the like.

Step 4

A process for the production of IGF-I or fused IGF-I which comprises culturing said transformant in a suitable medium.

Step 5

A process for isolation of IGF-I or fused IGF-I from host organism cells.

Step 6 (optional)

A process for the production of IGF-I which comprises subjecting said fused IGF-I to cleavage reaction conditions to separate the IGF-I from the protective peptide.

The "protective peptide" in the term "fused IGF-I" is used for the protection of IGF-I from degradation by protease in the cells of a host organism, and is removed by cleavage reaction of the fused IGF-I. Namely, said fused IGF-I is an intermediate for preparing IGF-I by cleavage reaction. The protective peptide ("protein/-peptide" hereinafter) can be any cleavable protective peptide derived from a natural or a synthetic protein, a natural or a synthetic peptide, or a fragment thereof.

Suitable "fused IGF-I" may include i) IGF-I fused with a protein peptide through a methionine residue of the protein/peptide, ii) IGF-I fused with a protein peptide through tryplophar residue of the protein/peptide, or iii) IGF-I fused with a protein/peptide through a "-Gly-Pro-Ala-" sequence of the protein/peptide.

Suitable agents which may be used in this cleavage reaction may include cyanogen bromide; (3-bromo-2-o-nitrophenylsulfenyl)skatole (hereinafter referred to as BNPS-skatole) or N-chlorosuccinimide (hereinafter referred to as NCS); collagenase and the like, which can be suitably selected according to the type of starting fused IGF-I.

In this step, when the protein/peptide is fused with IGF-I through a methionine residue of the protein/peptide, fused IGF-I can be converted to IGF-I by cleavage reaction with cyanogen bromide in high yields.

In addition, when the protein/peptide is fused with IGF-I through tryptophan residue of the protein/peptide, fused IGF-I can be converted to IGF-I by cleavage reaction with BNPS-skatole or NCS.

Further, when the protein/peptide is fused with IGF-I through a "-Gly-Pro-Ala-" sequence of the protein/peptide, fused IGF-I can be converted by cleavage reaction to IGF-I with collagenase.

The present cleavage reaction can be conducted under mild conditions in a conventional solvent which does not adversely affect the reaction.

From the above amino acid sequence of IGF-I, a corresponding nucleotide sequence has been invented, subject to a number of specific non-obvious criteria. The IGF-I gene has been cloned by inserting it into a known plasmid, as a cloning plasmid. The IGF-I gene has been excised from the recombinant plasmid, and then inserted into a plasmid specifically designed to maximize expression of the IGF-I gene under the control of a promoter. A structural gene coding for a protective peptide is optionally inserted into the recombinant plasmid upstream of and adjacent to the IGF-I gene.

Although the present invention is illustrated in detail hereinafter, the present invention is not limited thereto.

[1] Preparation and Cloning of an IGF-I gene (1) Preparation of an IGF-I gene

From the above amino acid sequence, because of the diversity of the genetic code, it is possible to predict numerous nucleotide sequences which would code for the IGF-I.

In the present invention, in the determination of an optimum sequence to use from a large number of possibilities, several non-obvious criteria have been observed. Firstly, trinucleotide codons should be used which are acceptable in the host organism used. Secondly, it is desirable to have different restriction enzyme recognition sites at the terminal of the molecule so as to allow insertion thereof into a plasmid in a desired orientation. Moreover, select sites would be used which will allow to use well known cloning plasmids. Thirdly, the synthesis should not be unnecessarily complicated, and illegitimate cross-annealing should be minimized in order to facilitate gene assembly, so that stable off-diagonal interactions might be avoided as much as possible.

One of the preferred sequence selected for the coding for portion of the IGF-I gene (210 bp) is as follows:

```
                 1
              Gly   Pro   Glu   Thr   Leu   Cys   Gly   Ala
Coding:     5'-GGT—CCT—GAA—ACT—CTG—TGC—GGC—GCT—
Noncoding:  3'-CCA—GGA—CTT—TGA—GAC—ACG—CCG—CGA—
```

-continued

```
                  10                                      20
Glu  Leu  Val  Asp  Ala  Leu  Gln  Phe  Val  Cys  Gly  Asp  Arg
GAA—CTG—GTT—GAC—GCT—CTG—CAA—TTT—GTA—TGT—GGT—GAT—CGT—
CTT—GAC—CAA—CTG—CGA—GAC—GTT—AAA—CAT—ACA—CCA—CTA—GCA—

30
Gly  Phe  Tyr  Phe  Asn  Lys  Pro  Thr  Gly  Tyr  Gly  Ser  Ser
GGT—TTC—TAC—TTC—AAC—AAA—CCG—ACC—GGC—TAT—GGC—TCC—AGC—
CCA—AAG—ATG—AAG—TTG—TTT—GGC—TGG—CCG—ATA—CCG—AGG—TCG—

40
Ser  Arg  Arg  Ala  Pro  Gln  Thr  Gly  Ile  Val  Asp  Glu  Cys
TCT—CGT—CGC—GCA—CCG—CAG—ACT—GGT—ATC—GTA—GAC—GAA—TGC—
AGA—GCA—GCG—CGT—GGC—GTC—TGA—CCA—TAG—CAT—CTG—CTT—ACG—

50                                        60
Cys  Phe  Arg  Ser  Cys  Asp  Leu  Arg  Arg  Leu  Glu  Met  Tyr
TGT—TTT—CGT—TCT—TGC—GAT—CTC—CGC—CGT—CTG—GAA—ATG—TAC—
ACA—AAA—GCA—AGA—ACG—CTA—GAG—GCG—GCA—GAC—CTT—TAC—ATG—

70
Cys  Ala  Pro  Leu  Lys  Pro  Ala  Lys  Ser  Ala
TGT—GCT—CCA—CTG—AAG—CCA—GCA—AAA—TCC—GCG-3'
ACA—CGA—GGT—GAC—TTC—GGT—CGT—TTT—AGG—CGC-5'
```

In the sequences given in this specification A, G, C and T represent the following formula:

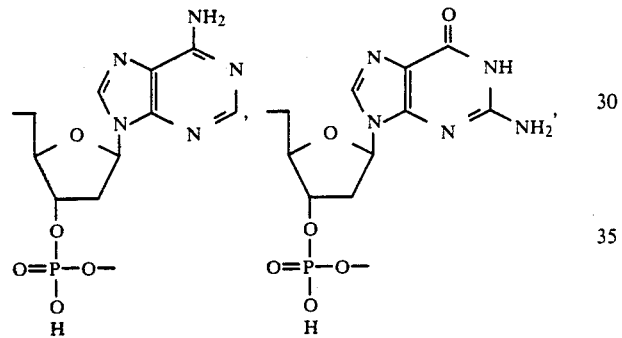

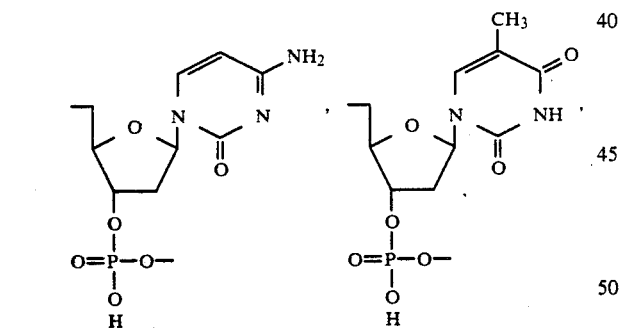

respectively, and 5'-terminal A, G, C and T represent the following formulae:

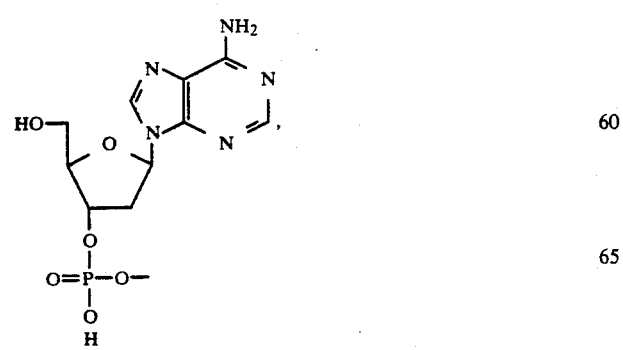

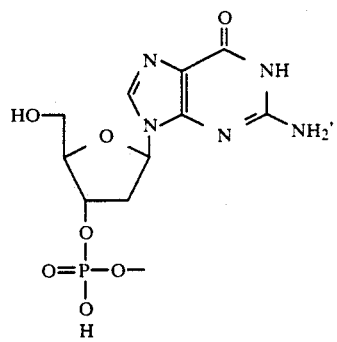

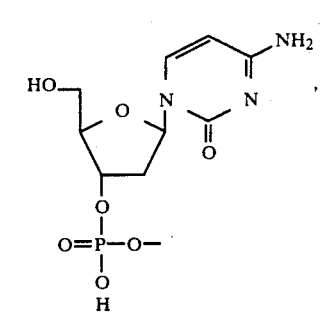

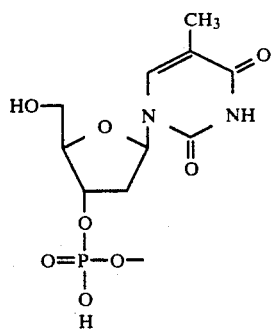

respectively, and 3'-terminal A, G, C and T represent the following formulae:

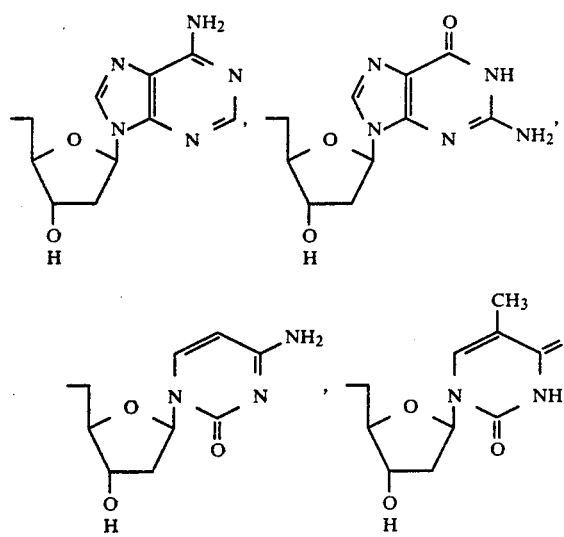

respectively.

Taking into consideration the above-mentioned criteria, particularly in consideration of the second criteria mentioned above, the following slightly longer sequence (224 bp) can be selected.

In a suitable embodiment of this invention, EcoRI and BamHI sites can be selected and introduced at the 5' and 3' ends, respectively.

Further, a methionine codon (ATG) was inserted upstream of and adjacent to the codon of N-terminal amino acid of IGF-I, and two stop codons (TGA and TAG) were inserted downstream of and adjacent to the C-terminal codon.

which were annealed and ligated in pre-determined stages to give the above double-stranded nucleotide sequence.

In the synthesis of oligonucleotides in this specification, the following abbreviations are used.

Ap, Gp, Cp and Tp represent the following formulae:

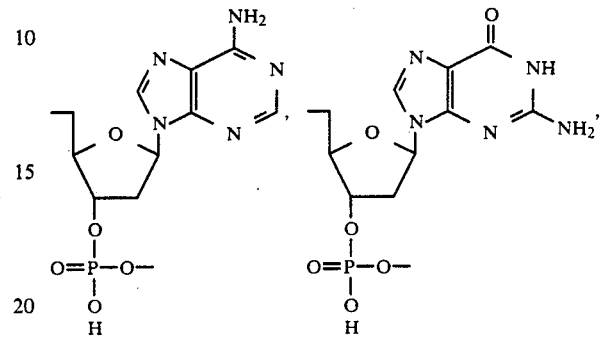

```
                    (AvaII)
            EcoRI    Met   Gly   Pro   Glu   Thr   Leu   Cys   Gly
Coding:     5'-AATTC—ATG—GGT—CCT—GAA—ACT—CTG—TGC—GGC—
Noncoding:       3'-G—TAC—CCA—GGA—CTT—TGA—GAC—ACG—CCG—

10    (Hinc II)                                          20
Ala  Glu  Leu  Val  Asp  Ala  Leu  Gln  Phe  Val  Cys  Gly  Asp  Arg
GCT—GAA—CTG—GTT—GAC—GCT—CTG—CAA—TTT—GTA—TGT—GGT—GAT—CGT—
CGA—CTT—GAC—CAA—CTG—CGA—GAC—GTT—AAA—CAT—ACA—CCA—CTA—GCA—

30
Gly  Phe  Tyr  Phe  Asn  Lys  Pro  Thr  Gly  Tyr  Gly  Ser  Ser  Ser
GGT—TTC—TAC—TTC—AAC—AAA—CCG—ACC—GGC—TAT—GGC—TCC—AGC—TCT—
CCA—AAG—ATG—AAG—TTG—TTT—GGC—TGG—CCG—ATA—CCG—AGG—TCG—AGA—

40
Arg  Arg  Ala  Pro  Gln  Thr  Gly  Ile  Val  Asp  Glu  Cys  Cys  Phe
CGT—CGC—GCA—CCG—CAG—ACT—GGT—ATC—GTA—GAC—GAA—TGC—TGT—TTT—
GCA—GCG—CGT—GGC—GTC—TGA—CCA—TAG—CAT—CTG—CTT—ACG—ACA—AAA—

50                                              60
Arg  Ser  Cys  Asp  Leu  Arg  Arg  Leu  Glu  Met  Tyr  Cys  Ala  Pro
CGT—TCT—TGC—GAT—CTC—CGC—CGT—CTG—GAA—ATG—TAC—TGT—GCT—CCA—
GCA—AGA—ACG—CTA—GAG—GCG—GCA—GAC—CTT—TAC—ATG—ACA—CGA—GGT—

70
Leu  Lys  Pro  Ala  Lys  Ser  Ala  stop  stop  BamHI
CTG—AAG—CCA—GCA—AAA—TCC—GCG—TGA—TAG-3'
GAC—TTC—GGT—CGT—TTT—AGG—CGC—ACT—ATC—CTAG-5'
```

The present invention also relates to a process for the production of such a gene characterized in that it comprises annealing and ligation of a number of the corresponding oligonucleotide blocks.

(i) Synthesis of oligonucleotides

A molecule having the above expanded sequence was synthesized by making 30 synthetic oligonucleotides, which were annealed and ligated in pre-determined stages to give the above double-stranded nucleotide sequence.

respectively, and 3'-teminal A, G, C and T represent the following formulae:

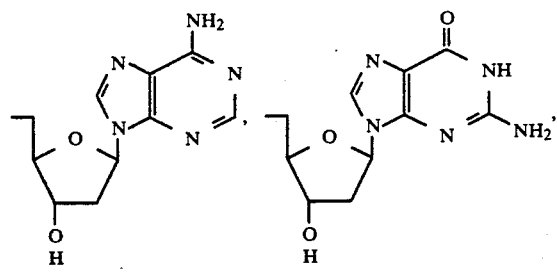

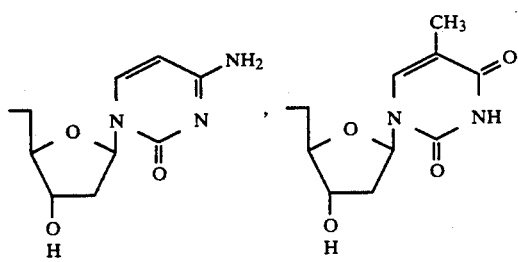

respectively, and $A^{Bz}$po, $G^{iB}$po, $C^{Bz}$po, Tpo and $^{Ac}$Upo represent the following formulae:

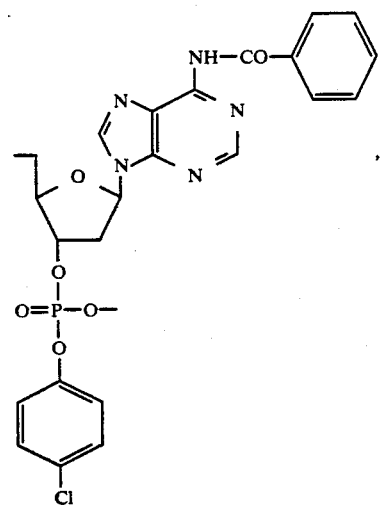

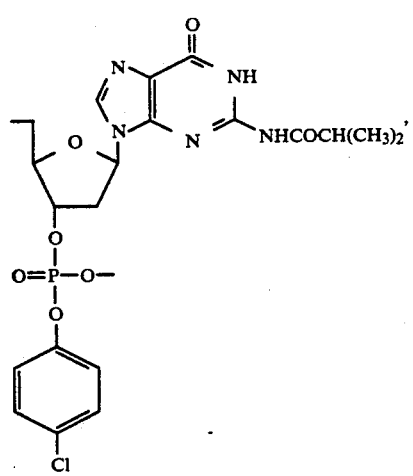

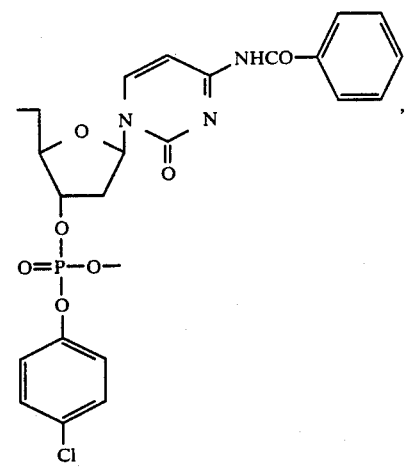

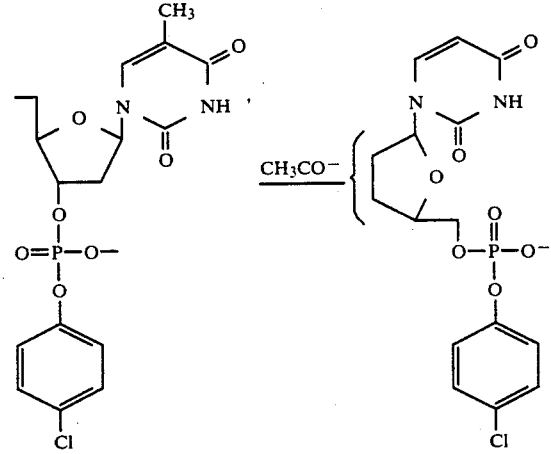

respectively, and
DMTr is dimethoxytrityl,
B is a base selected from adenine, guanine, cytosine and thymine (for convenience, protecting group are not shown),
U is uracil,
Ac is acetyl,
m is an integer of 1 or 2,
n is an integer of 1 to 12, and
CE is cyanoethyl.

The following oligonucleotides were synthesized:
(1) HOApApTpTpCpApTpGpGpGpTOH (A1)
(2) HOTpTpTpCpApGpGpApCpCpCpApTpGOH (A2)
(3) HOCpCpTpGpApApApCpTpCpTpGpTpGOH (B1)
(4) HOCpApGpCpGpCpCpGpCpApCpApGpAp-GOH (B2)
(5) HOCpGpGpCpGpCpTpGpApApCpTpGpG-pTOH (C1)
(6) HOApGpApGpCpGpTpCpApApCpCpApGpT-pTOH (C2)
(7) HOTpGpApCpGpCpTpCpTpGpCpApApTpT-pTOH (D1)
(8) HOCpCpApCpApTpApCpApApApTpTpGpCOH (D2)
(9) HOGpTpApTpGpTpGpGpTpGpApTpCpG-pTOH (E1)
(10) HOTpApGpApApApCpCpApCpGpApTp-CpAOH (E2)

(11) HOGpGpTpTpTpCpTpApCpTpTpCpApAp-COH (F1)

(12) HOGpGpTpCpGpGpTpTpTpGpTpGpApAp-GOH (F2)

(13) HOApApApCpCpGpApCpCpGpGpCpTpApT-pGOH (G1)

(14) HOGpCpTpGpGpApGpCpCpApTpApGpC-pCOH (G2)

(15) HOGpCpTpCpCpApGpCpTpCpTpCpGpT-pCOH (H1)

(16) HOCpGpGpTpGpCpGpCpGpApCpGpApG-pAOH (H2)

(17) HOGpCpGpCpApCpCpGpCpApGpApCpT-pGOH (I1)

(18) HOCpTpApCpGpApTpApCpCpApGpTpCpT-pGOH (I2)

(19) HOGpTpApTpCpGpTpApGpApCpGpApApT-pGOH (J1)

(20) HOGpApApApApCpApGpCpApTpTpCpG-pTOH (J2)

(21) HOCpTpGpTpTpTpTpCpGpTpTpCpTpT-pGOH (K1)

(22) HOGpGpApGpApTpCpGpCpApApApGpApAp-COH (K2)

(23) HOCpGpApTpCpTpCpCpGpCpCpGpTpC-pTOH (L1)

(24) HOTpApCpApTpTpTpCpCpApGpApCpGpG-pCOH (L2)

(25) HOGpGpApApApApTpGpTpApCpTpGpTpGpC-pTOH (M1)

(26) HOTpTpCpApGpTpGpGpApGpCpApCpAp-GOH (M2)

(27) HOCpCpApCpTpGpApApApGpCpCpApGp-CpAOH (N1)

(28) HOGpCpGpGpApTpTpTpTpGpCpTpGpG-pCOH (N2)

(29) HOApApApTpCpCpGpCpGpTpGpApTpAp-GOH (O1)

(30) HOGpApTpCpCpTpApTpCpApCOH (O2)

Methods of preparing oligonucleotides from smaller units by successive coupling reactions The successive coupling reaction is shown in FIG. 1. Mono(or di, or tri)mer (I) can be prepared by using Hirose's method [T. Hirose, PROTEIN, NUCLEIC ACID AND ENZYME ISSN, 25, 225(1980), published in Japan]. Coupling can be carried out on cellulose by using the phosphotriester method [R. Crea et al, Nucleic Acid Research 8, 2331(1980) and M. L. Duckworth et al, Nucleic Acid Research, 9, 1691(1981)].

Figure 2A:
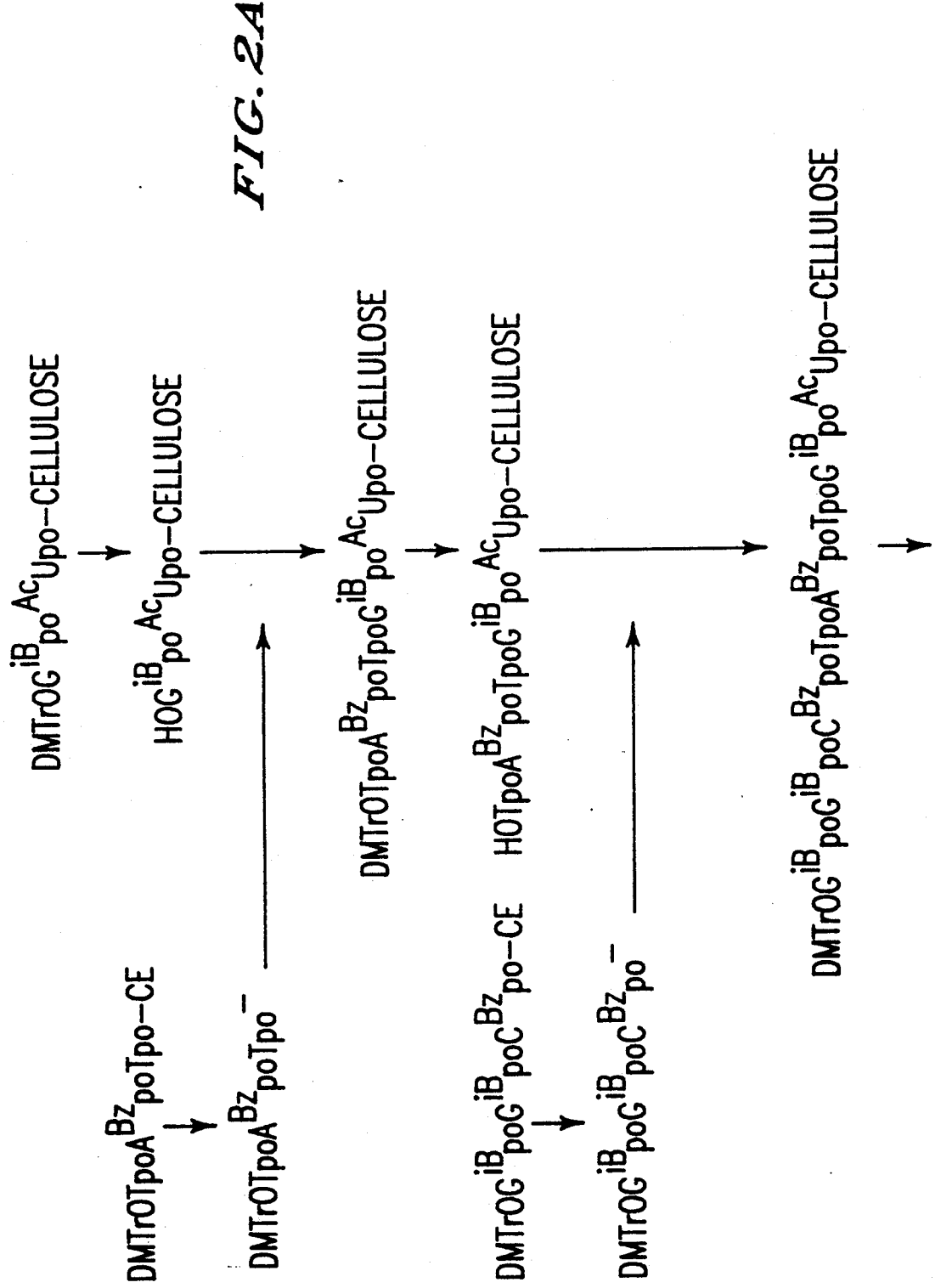
FIGS. 2A, B, & C are flow charts of the preparation of the hexadecanucleotide HOApApApCpCpGpApCpCpGpGpCpTpApTpGOH (G1).
Figure 2B:
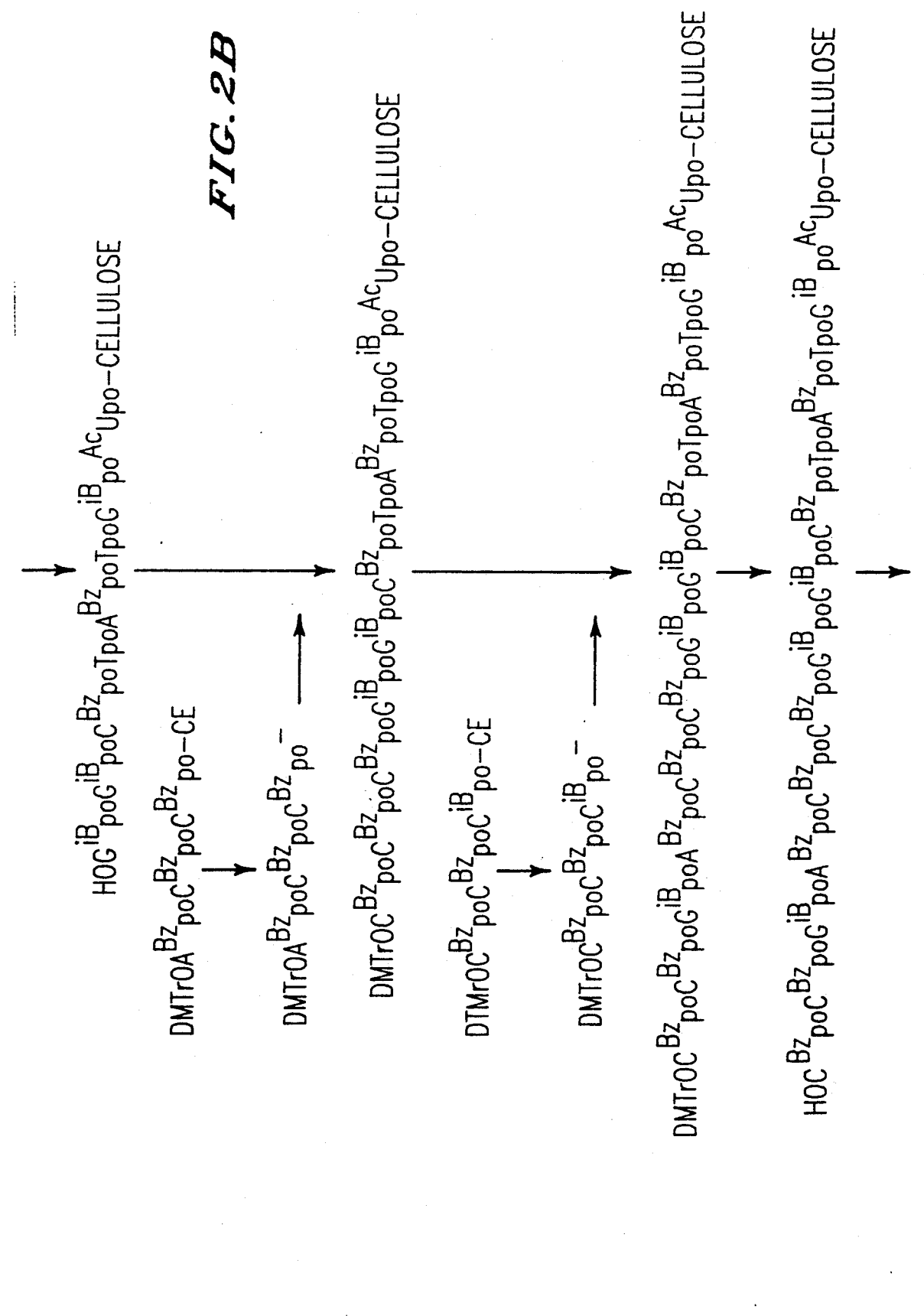

Particularly, the synthetic methods will now be illustrated with reference to the synthesis of the hexadecanucleotide HOApApApCpCpG-pApCpCpGpGpCpTpApTpGOH (G1) described in Example 1. The flow chart of the synthesis of the hexadecanucleotide G1 is shown in FIG. 2.

(ii) Annealing and ligation of chemically synthesized oligonucleotide

Figure 3:
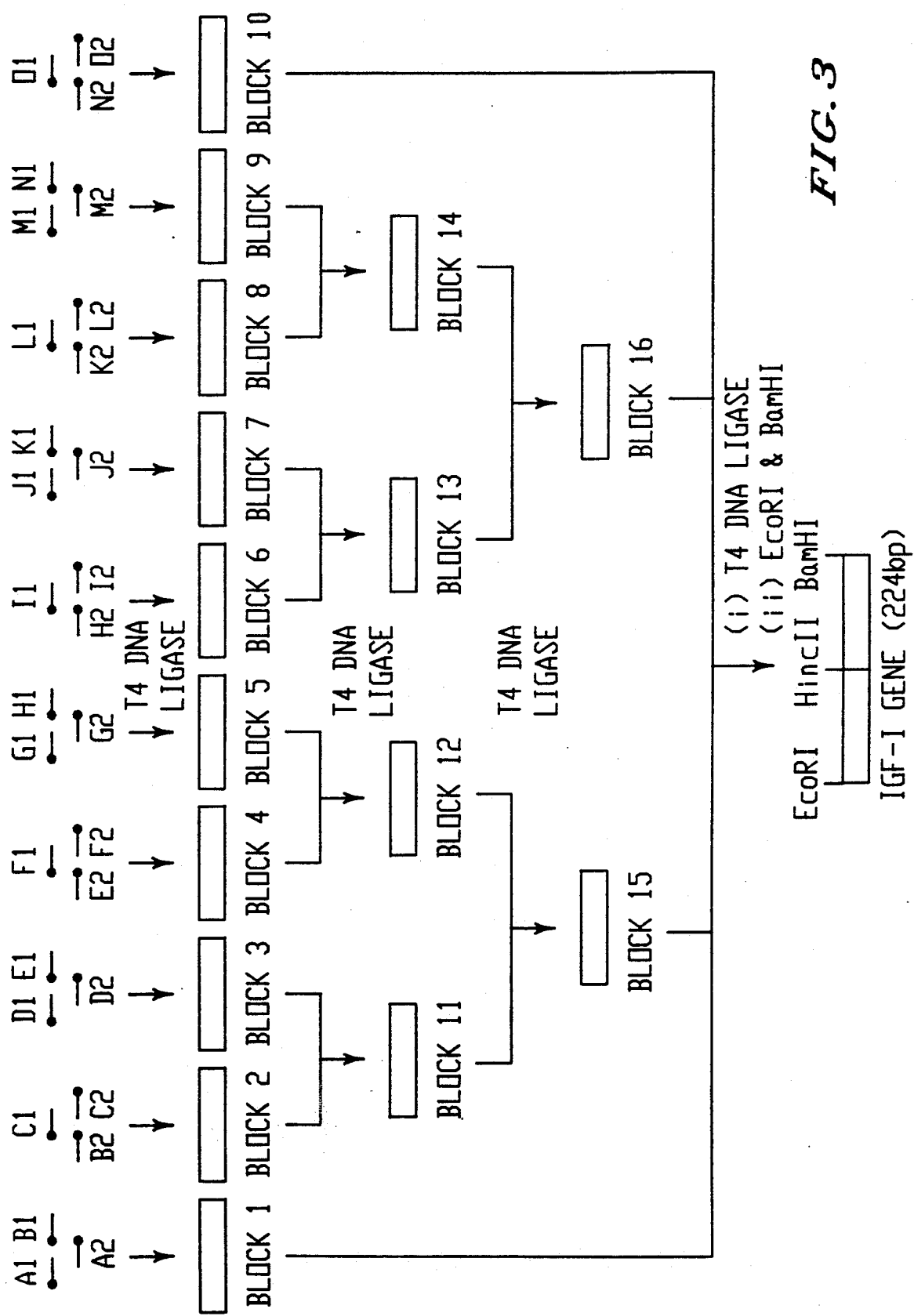
FIG. 3 illustrates the preparation of the IGF-I gene (224bp).

The oligonucleotides are annealed and ligated in a series of steps, in order to minimize the possibilities for undesirable interactions as shown in FIG. 3. In FIG. 3, an oligonucleotide is illustrated with ( means 5'-phosphorylated end). Ligation is conducted in the presence of T4 DNA ligase.

Oligonucleotides A1, B1 and A2; C1, B2 and C2; D1, E1 and D2; F1, E2, and F2; G1, H1, and G2; I1, H2 and I2; J1, K1 and J2; L1, K2 and L2; M1, N1 and M2 and O1, N2 and O2 were annealed and ligated to give Blocks 1 to 10, respectively. In this case Blocks 1 and 10 which were obtained from oligonucleotides A1, B1 and A2, and O1, N2 and O2, respectively, were annealed and ligated to each other to form dimers. Blocks 2 and 3; 4 and 5, 6 and 7, 8 and 9 were annealed and ligated to give Blocks 11, 12, 13 and 14, respectively. Blocks 11 and 12; 13 and 14 were annealed and ligated to form Blocks 15 and 16, respectively. Blocks 1, 15, 16 and 10 were annealed and ligated. The and thus obtained ligated mixture was cleaved by EcoRI and BamHI to give the IGF-I gene.

(2) Molecular cloning of the IGF-I gene

In order to clone the IGF-I gene, it is inserted into an appropriate plasmid, a cloning plasmid, having suitable enzyme recognition sites in which the IGF-I gene can be inserted.

in a preferred embodiment of this invention an IGF-I gene synthesized for the expression in $E.\ coli$ is inserted into a plasmid originated in $E.\ coli$ (e.g. pBR322, etc.) and cloning is conduced.

Figure 4:
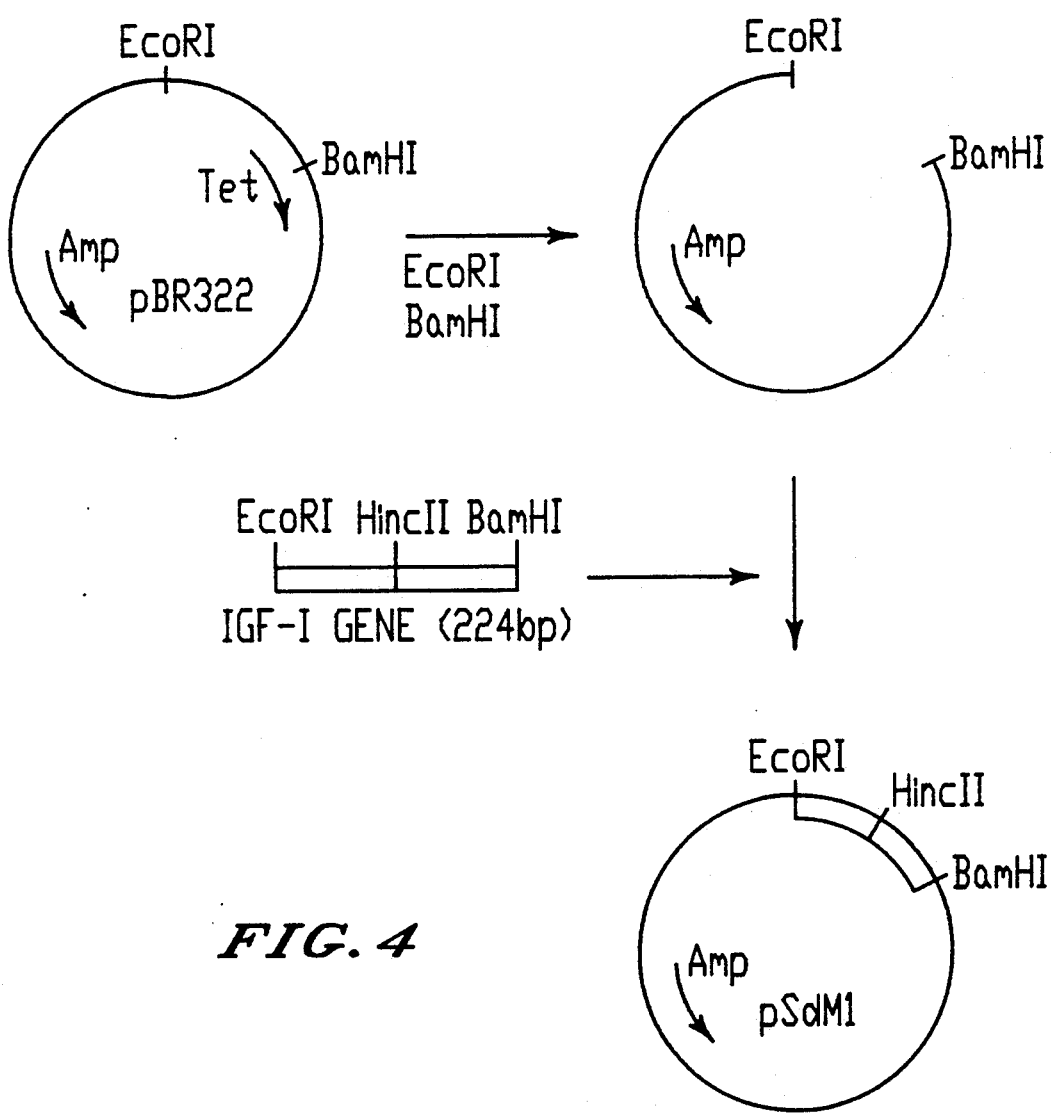
FIG. 4 illustrates the construction of plasmid pSdM1.

For example, in the case of using plasmid pBR322 (which is commercially available) which has EcoRI and BamHI sites, as shown in FIG. 4, the plasmid is cleaved by EcoRI and BamHI. In this case the plasmid codes for ampicillin resistance (indicated by Amp) on the longer fragment when cleaved by EcoRI and the coding for BamHI, and tetracycline resistance (indicated by Tet) vanishes as is consequence of cleavage of at the BamHI site. The longer fragment of EcoRI, BamHI-cleaved plasmid pBR322 was purified by electroelution, annealed and ligated with a large excess of the IGF-I gene using T4 DNA ligase. Thus obtained mixture was transformed into $E.\ coli$ HB101 (ATCC 33694). The plasmid was isolated from one of the obtained several ampicillin resistant and tetracycline sensitive transformants obtained and confirmed to contain the IGF-I gene by digestion with restriction enzyme and electrophoresis. This process is shown in FIG. 4. The thus obtained plasmid is named as plasmid pSdM1.

(3) Sequence of the IGF-I gene in plasmid pSdM1

The Maxam-Gilbert method can be used.

For sequencing the IGF-I gene, plasmid pSdM1 was digested with EcoRI and then treated with AMV reverse transcriptase in the presence of $\alpha\text{-}^{32}\text{P}$-ATP. The linear plasmid labeled with $^{32}P$ was digested with BamHI to give two fragments (224 bp, 4.0 kbp). The smaller fragment (224 bp) was sequenced by the Maxam-Gilbert method [A. Maxam and W. Gilbert, Proc. Natl. Acad. Sci. USA 74, 560 (1977)]. On the other hand, plasmid pSdM1 was digested with BamHI first, and then labeled with $^{32}P$ as described above. The linear plasmid was digested with EcoRI to give two fragments (224 bp, 4.0 kbp). The smaller fragment (224 bp) was sequence by the Maxam-Gilbert method. The sequencing results for both side of the IGF-I gene were agreed with the designed IGF-I gene.

[2] Preparation and Cloning of a Promoter Gene

A promoter gene was designed obtain IGF-I from a host organism.

The promoter gene obtained was inserted into a plasmid such that the promoter gene was located upstream of and adjacent to the IGF-I gene or the fused IGF-I gene.

In a preferred embodiment of this invention a synthetic trp promoter I gene a synthetic trp promoter II gene were designed.

(1) DNA sequence of a synthetic trp promoter I gene

The following DNA sequence was designed for the synthetic trp promoter I gene (107 bp).

```
          EcoRI*
      5'-AATTTGCCGACATCATAACGGTTCTGGCAAATATTCTGAAATGAGC—
      3'-    ACGGCTGTAGTATTGCCAAGACCGTTTATAAGACTTTACTCG—
```

```
    ———————— promoter region ————————>|

TGTTGACAATTAATCATCGAACTAGTTAACTAGTACGCAAGTTCACGTAAA—
      ACAACTGTTAATTAGTAGCTTGATCAATTGATCATGCGTTCAAGTGCATTT—

|SD sequence|
      |<—>|    EcoRI
         AAGGGTATCG-3'
         TTCCCATAGCTTAA-5'
```

The region for "promoter region" and "SD seqeunce" are shown in the above sequence.

(2) Preparation of synthetic trp promoter II gene

To insert the synthetic trp promoter I described above in a correct direction into a plasmid, a synthetic promoter, synthetic trp promoter II, having a certain length of base pair chain following the EcoRI site of synthetic trp promoter I and BamHI site at 3'-end was prepared.

A molecule having 163 bp was synthesized by making 22 synthetic oligonucleotide blocks, which to were assembled by single-strand overlaps to give the complete double-stranded nucleotide sequence.

```
          EcoRI*
      5'-AATTTGCCGACATCATAACGGTTCTGGCAAATATTCTGAAATGAGC-
      3'-    ACGGCTGTAGTATTGCCAAGACCGTTTATAAGACTTTACTCG-

HpaI
      TGTTGACAATTAATCATCGAACTAGTTAACTAGTACGCAAGTTCACGTAAA-
      ACAACTGTTAATTAGTAGCTTGATCAATTGATCATGCGTTCAAGTGCATTT-

EcoRI
      AAGGGTATCGAATTCATGGCTGGTTGTAAGAACTTCTTTTGGAAGACTTTC-
      TTCCCATAGCTTAAGTACCGACCAACATTCTTGAAGAAAACCTTCTGAAAG-

BamHI
      ACTTCGTGTTGATAG-3'
      TGAAGCACAACTATCCTAG-5'
```

(i) Synthesis of oligonucleotides

The following twenty-two oligonucleotides were synthesized.

(1) HOApApTpTpTpGpCpCpGpApCpAOH (A)
(2) HOCpGpTpApTpGpApTpGpTpCpGpGpCpAOH (B)
(3) HOTpCpApTpApApCpGpGpTpTpCpTpGpGpCOH (C)
(4) HOGpApApTpApTpTpTpGpCpCpApGpApApAp-COH (D)
(5) HOApApApTpApTpTpCpTpGpApApApTpGpAOH (E)
(6) HOTpCpApApCpApGpCpTpCpApTpTpTpCpAOH (F)
(7) HOGpCpTpGpTpTpGpApCpApApTpTpApApAp-TOH (G)
(8) HOGpTpTpCpGpApTpGpApTpTpApApTpTpGpGOH (H)
(9) HOCpApTpCpGpApApCpTpApGpTpTpApApAp-COH (I)
(10) HOGpCpGpTpApCpTpApGpTpTpApApCpTpAOH (J)
(11) HOTpApGpTpApCpGpCpApApApGpTpTpCpAp-COH (K)
(12) HOCpTpTpTpTpTpApCpGpTpGpApApCpTpTpTOH (L)
(13) HOGpTpApApApApApApGpGpGpTpApTpCp-GOH (M)
(14) HOApApTpTpCpGpApTpApCpCOH (N)
(15) HOApApTpTpCpApTpGpGpCpTOH (SA)
(16) HOGpGpTpTpGpTpApApGpApApCpTpTpCp-pTOH (SB)
(17) HOTpTpTpGpGpApApGpApCpTpTpTOH (SC)
(18) HOCpApCpTpTpCpGpTpGpTpTpGpApTpAp-GOH (SD)
(19) HOTpTpApCpApApCpApCpGpCpCpApTp-pGOH (SE)
(20) HOCpCpApApApApApGpApApGpTpTpCOH (SF)
(21) HOCpGpApApGpTpGpApApApApGpTpCpTp-pTOH (SG)

(22) HOGpApTpCpCpTpApTpCpApApCpAOH (SH)

The synthetic method will now be illustrated with reference to the synthesis of the hexadecanucleotide HOApApApCpCpGpApCpCpGpGpCpTpApT-pGOH (G1) mentioned above.

(ii) Annealing and ligation of chemically synthesized oligonucleotides

Figure 5:
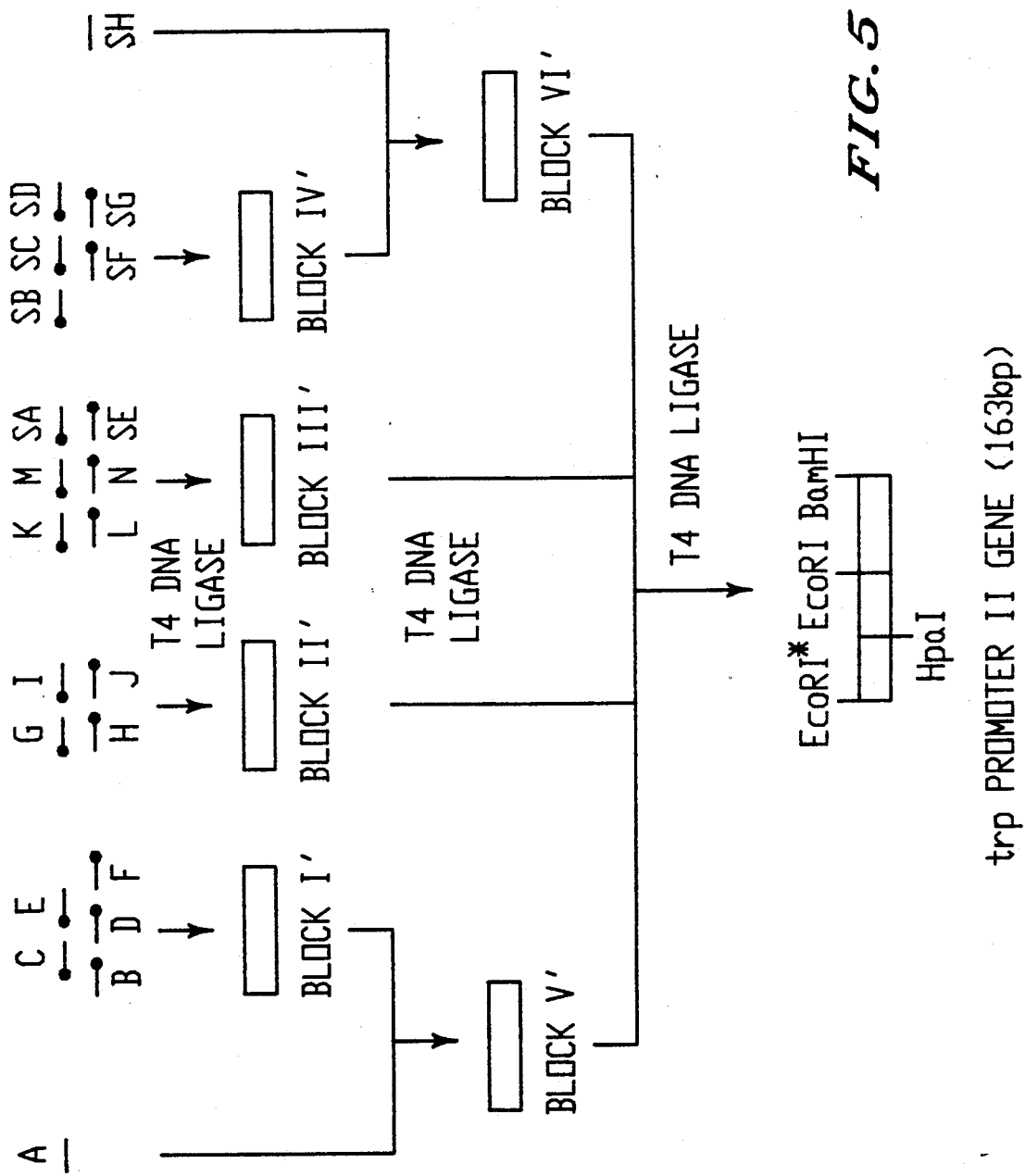
FIG. 5 illustrates the construction of a synthetic trp promoter II gene.

The oligonucleotide A to N and SA to SH were annealed and ligated as shown in FIG. 5 following a protocol a similar to that used for the IGF-I gene.

(3) Molecular cloning of synthetic trp promoter II gene

Figure 6:
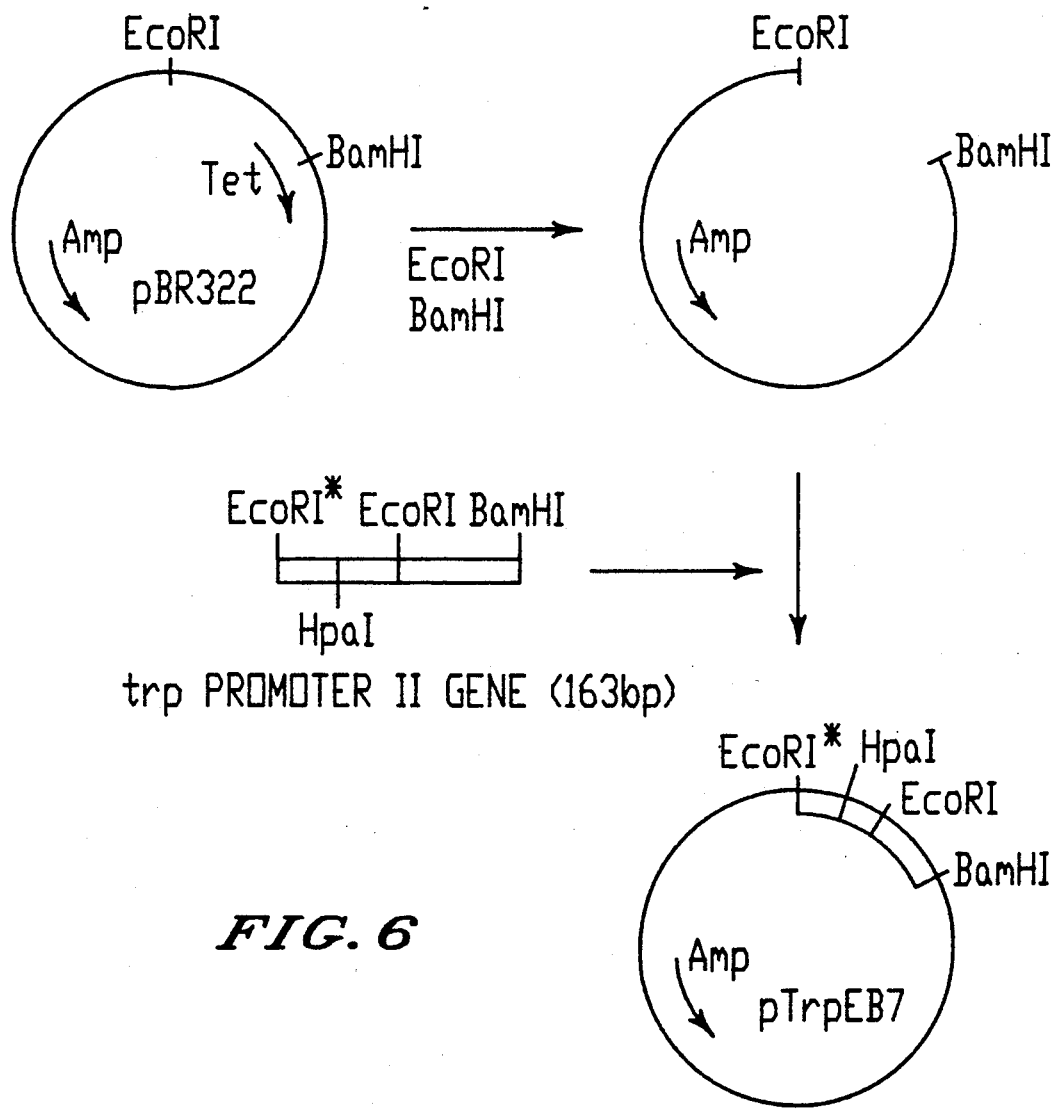
FIG. 6 illustrates the construction of plasmid pTrpEB7.

The synthetic trp promoter II gene was inserted into a plasmid. In a suitable embodiment of this invention, the synthetic trp promoter II was inserted into plasmid pBR322 by cleaving the plasmid with EcoRI and BamHI as shown in FIG. 6. The thus obtained plasmid was named plasmid pTrpEB7.

[3] Preparation and Cloning of the Protein/Peptide LH Gene

As a suitable example of a protective peptide which can be fused with IGF-I, a gene coding for protein/peptide LH (hereinafter referred to as protein/peptide LH gene) has been prepared. ("LH" is used in this text to define a protein/peptide derived from the left hand of γ-interferon.)

(1) Preparation of the protein/peptide LH gene

A molecule having 236 bp by making 32 synthetic oligonucleotide blocks, which were assembled by single-strand overlaps to give the complete double stranded nucleotide sequence.

```
                    1
             EcoRI  Met  Cys  Tyr  Cys  Gln  Asp  Pro  Tyr
    Coding:  5'-AATTC—ATG—TGT—TAC—TGC—CAG—GAC—CCA—TAT—
    Noncoding:   3'-G—TAC—ACA—ATG—ACG—GTC—CTG—GGT—ATA—

10                                              20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                              HindIII     60
Ser  Gln  Ile  Val  Ser  Phe  Tyr  Phe  Lys  Leu  Phe  Lys  Asn  Phe
AGC—CAA—ATT—GTC—TCC—TTT—TAC—TTC—AAG—CTT—TTC—AAA—AAC—TTT—
TCG—GTT—TAA—CAG—AGG—AAA—ATG—AAG—TTC—GAA—AAG—TTT—TTG—AAA—

70
Lys  Asp  Asp  Gln  Ser  Ile  Gln  Lys  Ser  Val  Stop  Stop  BamHI
AAG—GAT—GAC—CAG—AGC—ATC—CAA—AAG—AGT—GTG—TAA—TGA—TAG
TTC—CTA—CTG—GTC—TCG—TAG—GTT—TTC—TCA—CAC—ATT—ACT—ATCCTAG
```

(i) Synthesis of oligonucleotides

The following oligonucleotide blocks were synthesized:

(1) HOApApTpTpCpApTpGpTpGpTpTOH (a1)
(2) HOApCpTpGpCpCpApGpGpApCpCpCpAp-TOH (a2)
(3) HOApTpGpTpApApApApGpApApGpCpAp-GOH (a3)
(4) HOTpGpGpCpApGpTpApApCpApCpApT-pGOH (a4)
(5) HOTpTpTpApCpApTpApTpGpGpGpTpCpCOH (a5)
(6) HOApApGpGpTpTpTpTpCpTpGpCpTpTpC-pTOH (a6)
(7) HOApApApApCpCpTpTpApApGpApApApT-pAOH (b1)
(8) HOCpTpTpTpApApTpGpCpApGpGpTpCpAOH (b2)
(9) HOTpTpCpApGpApTpGpTpApGpCpGpG-pAOH (b3)
(10) HOApTpTpApApApGpTpApTpTpTpCpT-pTOH (b4)
(11) HOApTpCpTpGpApApTpGpApCpCpTpG-pCOH (b5)
(12) HOTpTpCpCpApTpTpApTpCpCpGpCpTpAp-COH (b6)
(13) HOTpApApTpGpGpApApCpTpCpTpTpTpT-pCOH (c1)
(14) HOTpTpApGpGpCpApTpTpTpTpGpApAp-GOH (c2)
(15) HOApApTpTpGpGpApApApGpApGpGpAp-GOH (c3)
(16) HOTpGpCpCpTpApApGpApApApApGpAp-GOH (c4)
(17) HOTpCpCpApApTpTpCpTpTp-CpApApApAOH (c5)
(18) HOCpTpGpTpCpApCpTpCpTpCpTpCpT-pTOH (c6)
(19) HOApGpTpGpApCpApGpApApApApApT-pAOH (d1)
(20) HOApTpGpCpApGpApGpCpCpApApApT-pTOH (d2)
(21) HOGpTpCpTpCpCpTpTpTpApCpTpTOH (d3)
(22) HOCpTpCpTpGpCpApTpApTpTpTpT-pTOH (d4)
(23) HOApGpGpApGpApCpApApTpTpGpGOH (d5)

(24) HOApApApGpCpTpTpGpApApGpTpApApAOH (d6)
(25) HOCpApApGpCpTpTpTpTpCpApApApApAOH (e1)
(26) HOCpTpTpTpApApGpGpApTpGpApCpCpAOH (e2)
(27) HOGpApGpCpApTpCpCpApApApApGpApGOH (e3)
(28) HOCpCpTpTpApApApGpTpTpTpTpGpAOH (e4)
(29) HOGpGpApTpGpCpTpCpTpGpGpTpCpApTOH (e5)
(30) HOTpGpTpGpTpApApTpGpApTpApGOH (11)
(31) HOTpApCpApCpApCpTpCpTpTpTpTOH (12)
(32) HOGpApTpCpCpTpApTpCpApTOH (13)

(ii) Annealing and ligation of chemically synthesized oligonucleotides

Figure 7:
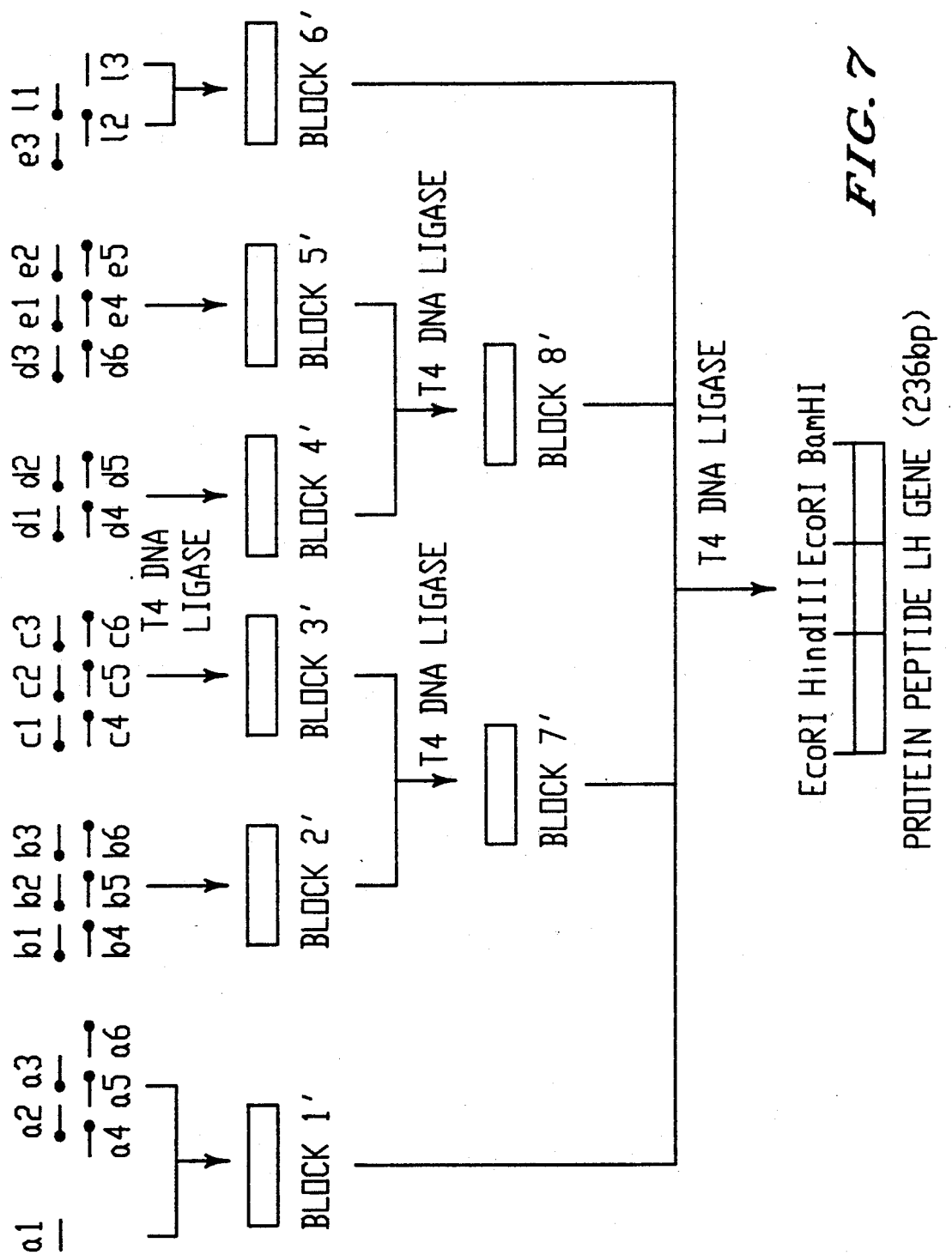
FIG. 7 illustrates the construction of a protein/peptide LH gene (236bp).

The oligonucleotides a1 to 13 were annealed and ligated as shown in FIG. 7 following a protocol similar to that used for the IGF-I gene.

(2) Molecular cloning of protein/peptide LH gene

Figure 8:
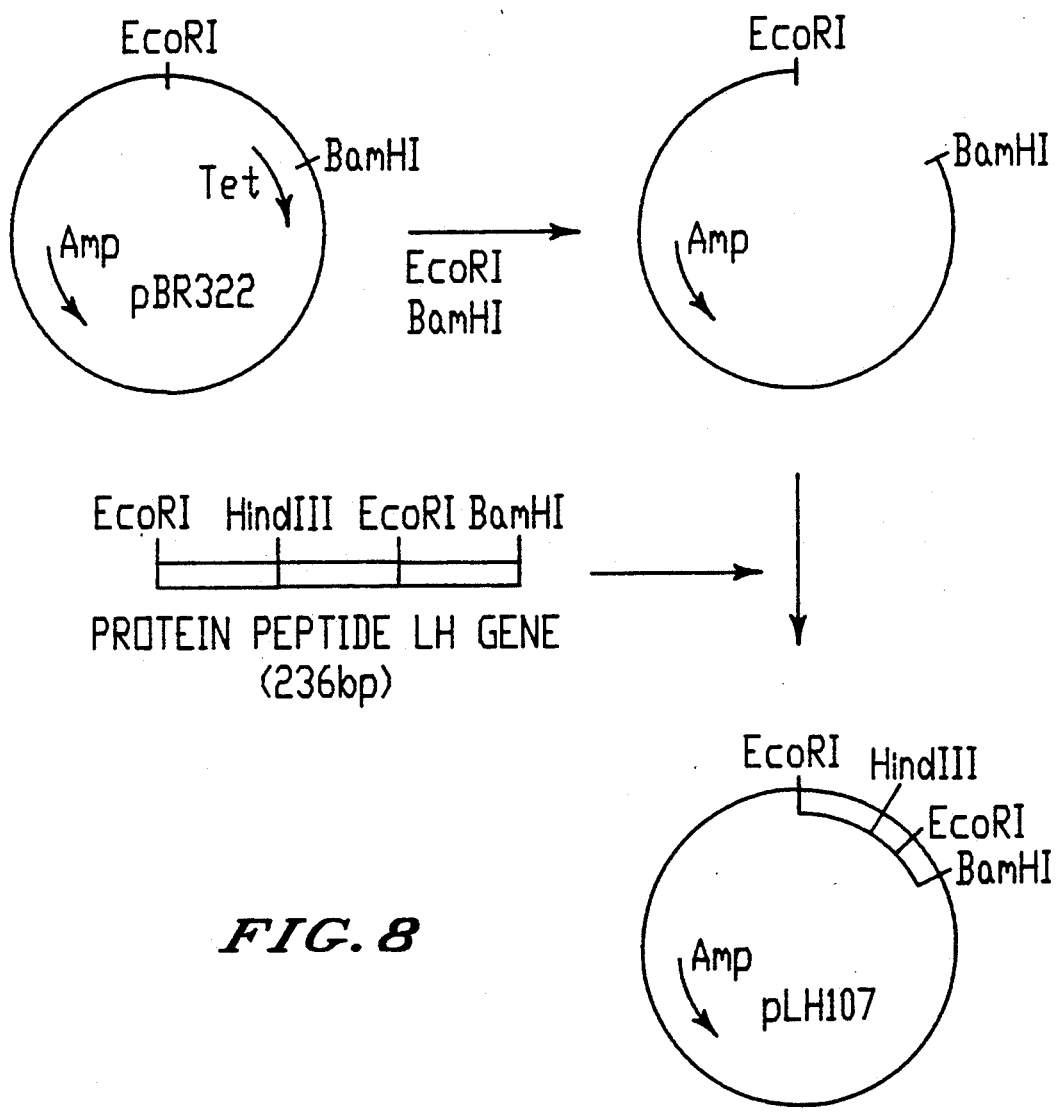
FIG. 8 illustrates the construction of plasmid pLH107.

Protein/peptide LH gene was inserted into a plasmid. For a suitable embodiment of this invention, protein/peptide LH gene was inserted into plasmid pBR322 by cleaving the plasmid with EcoRI and BamHI as shown in FIG. 8. The thus obtained plasmid was named plasmid pLH107.

[4] Construction of Expression Plasmid of IGF-I

The IGF-I gene was inserted into a plasmid containing a promoter gene, and the IGF-I gene was transformed into a host organism.

In a suitable embodiment of this invention, the following recombinant plasmids were established as being able to express the IGF-I gene in *E. coli*.

(1) Construction of recombinant plasmid pSdM1-322trp

Figure 9:
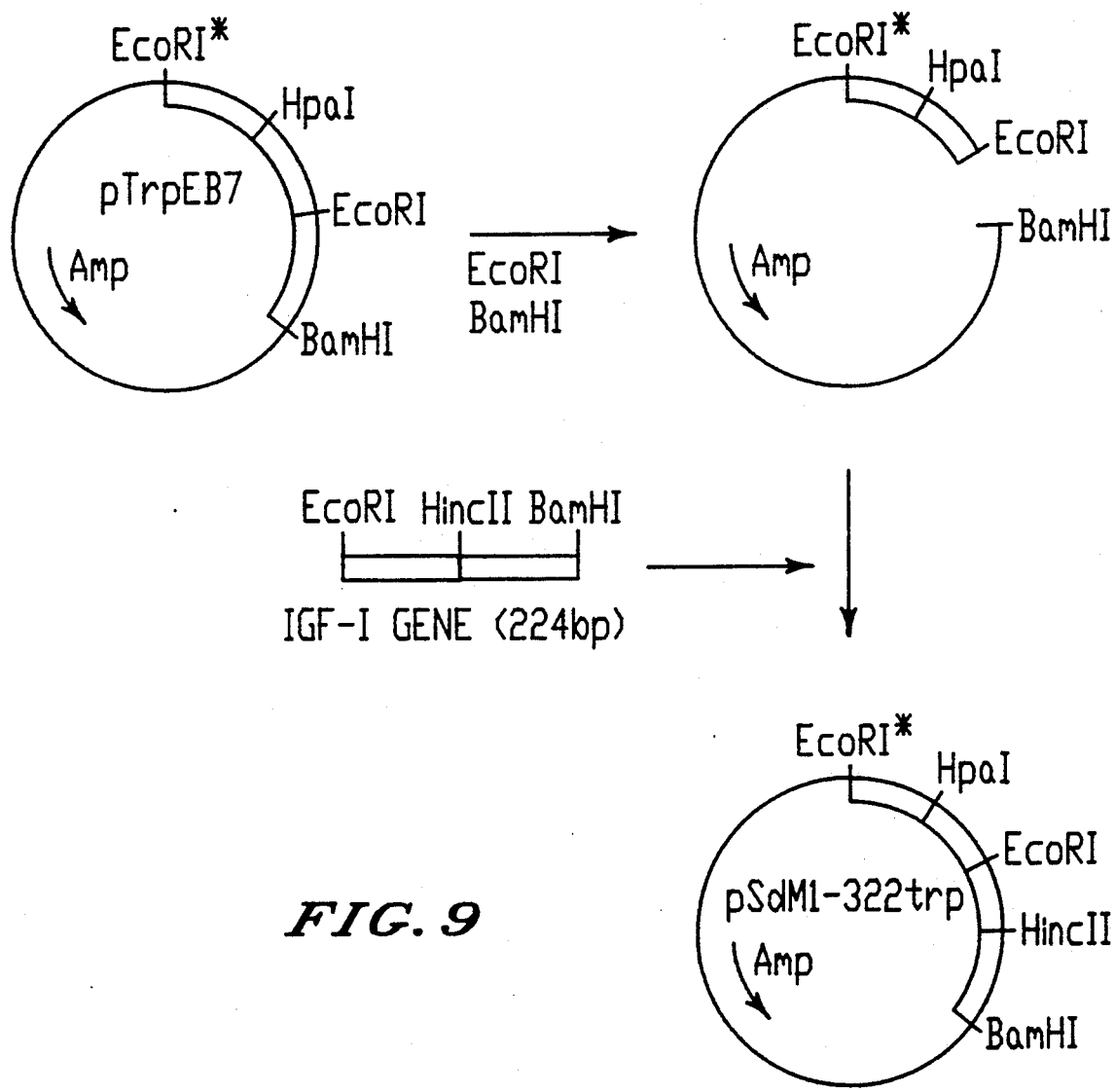
FIG. 9 illustrates the construction of recombinant plasmid pSdM1-332trp.

Trp promoter plasmid pTrpEB7 was digested with EcoRI and BamHI. The resulting large fragment (4.1 kbp) was separated by agarose gel electrophoresis. On the other hand, the IGF-I gene was isolated from plasmid pSdM1, and ligated with the above large fragment (4.1 kbp). The mixture was transformed into *E. coli* HB101. The plasmid was isolated from one of the ampicillin resistant transformants obtained, and confirmed to contain IGF-I gene by digestion with restriction enzyme and electrophoresis. The thus obtained plasmid was named plasmid pSdM1-322trp and the *E. coli* containing the plasmid was named as *E. coli* F-3. This process is shown in FIG. 9.

(2) Sequence of IGF-I gene and the synthetic trp promoter I gene in plasmid pSdM1-322trp For sequencing of IGF-I and the synthetic trp promoter I gene, plasmid pSdM1-322trp was digested with EcoRI and treated with BAP (bacteria alkaline phosphatase), and then treated with T4 polynucleotide kinase in the presence of $\gamma$-$^{32}$P-ATP The labeled DNA was digested with HinfI to give two fragments (1100 bp and 480 bp). These fragments were sequences by the Maxam-Gilbert method. The resulting sequence coincided with both the designed sequence of IGF-I gene and the synthetic promoter I gene.

[5] Construction of Expression Plasmid of Fused IGF-I

A fused IGF-I gene which comprised linking a gene coding for a protective peptide with IGF-I gene with or without a linker upstream of the IGF-I gene was prepared.

In this process, the following three types of protein peptides are fused with IGF-I.

Type I: a protein peptide having a methionine residue as the last amino acid.

Type II: a protein peptide having a tryptophan residue as the last amino acid.

Type III: a protein peptide having a -Gly-Pro-Ala- sequence as the last amino acids The two obtained three types of fused IGF-I are as follows.

Type I: IGF-I fused with the protein/peptide through a methionine residue of the protein/peptide Type II: IGF-I fused with the protein/peptide through a tryplophan residue of the protein/peptide Type III: IGF-I fused with the protein/peptide through a "-Gly-Pro-Ala-" sequence of the protein/peptide The present invention also relates to expression plasmids of a gene coding one of these three types of fused IGF-I.

In a suitable embodiment of this invention, the following types of expression plasmid of a gene coding for IGF-I fused with protein/peptide LH were prepared.

The present invention also relates to a process for the invention of such a gene which is constructed by linking a gene coding for a protective peptide with the IGF-I gene upstream of the IGF-I gene with or without a linker.

(1) Construction an of expression plasmid of a protein/peptide LH gene

Protein/peptide LH gene was inserted into a plasmid containing a promoter gene, and the protein/peptide LH gene was transformed into a host organism.

In a suitable embodiment of this invention, the following recombinant plasmid was established to express protein/peptide LH gene in *E. coli*.

Figure 10:
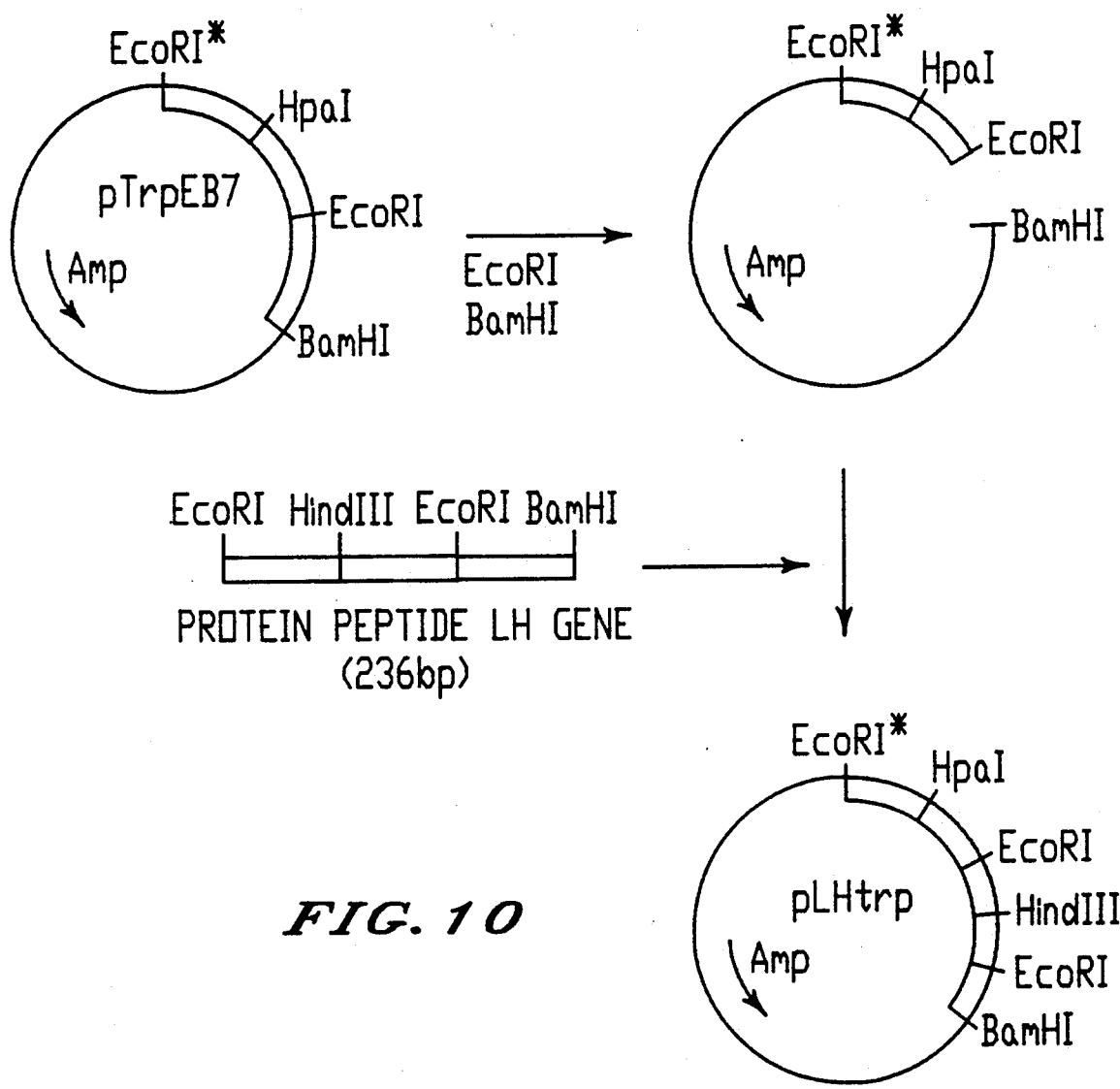
FIG. 10 illustrates the construction of plasmid pLHtrp.

The plasmid pTrpEB7 was digested with EcoRI and BamHI. The resulting large fragment (4.1 kbp) was separated by agarose gel electrophoresis. On the other hand, protein/peptide LH gene was isolated from plasmid pLH107, and ligated with the above large fragment (4.1 kbp). The mixture was transformed into *E. coli* HB101. The plasmid was isolated from one of the ampicillin resistant and tetracycline sensitive transformants obtained was, and confirmed to contain protein/peptide LH gene by digestion with restriction enzyme and electrophoresis. The thus obtained plasmid was named plasmid pLHtrp. This process is shown in FIG. 10.

(2) Construction of Expression Plasmid of IGF-I Fused with protein peptide LH

The IGF-I gene was inserted into a plasmid containing a protein/peptide LH gene downstream of and adjacent to a promoter gene.

In a suitable embodiment of this invention, the following recombinant plasmid was established to express IGF-I fused with protein/peptide LH gene in *E. coli*. In this stage, three types of linkers were inserted upstream of and adjacent to the IGF-I gene.

(a) Construction of Expression Plasmid of a Gene Coding for IGF-I fused with protein/peptide LH (Type I)

A plasmid pLHtrp prepared above was digested with HindIII and BamHI. The resultant large fragment was separated by preparative agarose gel electrophoresis.

Figure 11:
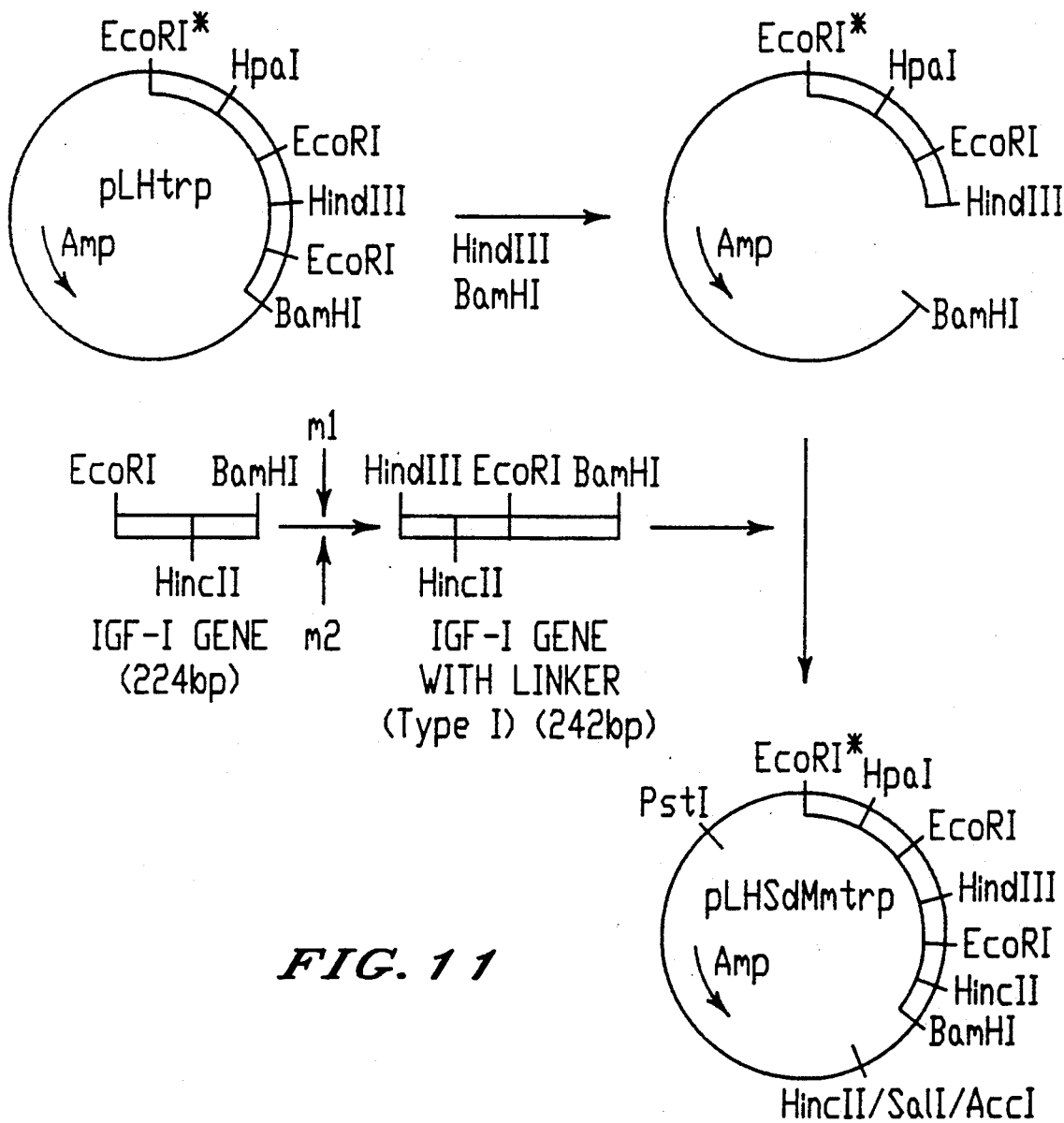
FIG. 11 illustrates the construction of plasmid pLHSdMmtrp.

On the other hand, the IGF-I gene was isolated from plasmid pSdM1 prepared above by EcoRI and BamHI digestion and oligonucleotides ml and m2 were ligated upstream of and adjacent to it as a linker. The thus obtained IGF-I gene with linker was ligated with the above large fragment of plasmid pLHtrp. The mixture coding for IGF-I fused with protein/peptide LH (Type I) by digestion with restriction enzyme and electrophoresis. The thus obtained plasmid was named plasmid pLHSdMmtrp. This process is shown in FIG. 11.

The thus obtained gene coding for IGF-I fused with protein/peptide LH (Type I) is as follows:

```
                         1
              EcoRI    Met   Cys   Tyr   Cys   Gln   Asp   Pro   Tyr
    Coding:   5'-AATTC—ATG—TGT—TAC—TGC—CAG—GAC—CCA—TAT—
    Noncoding:   3'-G—TAC—ACA—ATG—ACG—GTC—CTG—GGT—ATA—

10                                         20
Val   Lys   Glu   Ala   Glu   Asn   Leu   Lys   Lys   Tyr   Phe   Asn   Ala   Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His   Ser   Asp   Val   Ala   Asp   Asn   Gly   Thr   Leu   Phe   Leu   Gly   Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu   Lys   Asn   Trp   Lys   Glu   Glu   Ser   Asp   Arg   Lys   Ile   Met   gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                 HindIII       60
Ser   Gln   Ile   Val   Ser   Phe   Tyr   Phe   Lys   Leu   Glu   Val   Lys   His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

Glu   Phe   Met   Gly   Pro   Glu   Thr   Leu   Cys   Gly   Ala   Glu   Leu   Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—

80                                        90
Asp   Ala   Leu   Gln   Phe   Val   Cys   Gly   Asp   Arg   Gly   Phe   Tyr   Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn   Lys   Pro   Thr   Gly   Tyr   Gly   Ser   Ser   Ser   Arg   Arg   Ala   Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln   Thr   Gly   Ile   Val   Asp   Glu   Cys   Cys   Phe   Arg   Ser   Cys   Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

120                                              130
Leu   Arg   Arg   Leu   Glu   Met   Tyr   Cys   Ala   Pro   Leu   Lys   Pro   Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

Lys   Ser   Ala   Stop   stop   BamHI
AAA—TCC—GCG—TGA—TAG-3'
TTT—AGG—CGC—ACT—ATC—CTAG-5',
``` was transformed into *E. coli* HB101. The plasmid was isolated from one of the ampicillin resistant transformants obtained, and was confirmed to contain a gene and a gene coding for IGF-I fused with protein/peptide LH (Type I) is as follows:

```
                               1
                            Cys   Tyr   Cys   Gln   Asp   Pro   Tyr
    Coding:                 TGT—TAC—TGC—CAG—GAC—CCA—TAT—
    Noncoding:              ACA—ATG—ACG—GTC—CTG—GGT—ATA—

10                                         20
Val   Lys   Glu   Ala   Glu   Asn   Leu   Lys   Lys   Tyr   Phe   Asn   Ala   Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His   Ser   Asp   Val   Ala   Asp   Asn   Gly   Thr   Leu   Phe   Leu   Gly   Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—
```

-continued

```
                            40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                      HindIII      60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

70
Glu  Phe  Met  Gly  Pro  Glu  Thr  Leu  Cys  Gly  Ala  Glu  Leu  Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—

80                                      90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

120                                           130
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

Lys  Ser  Ala
AAA—TCC—GCG-3'
TTT—AGG—CGC-5'
```

(b) Construction of expression plasmid of a gene coding for IGF-I fused with protein/peptide LH (Type II)

Figure 12C:
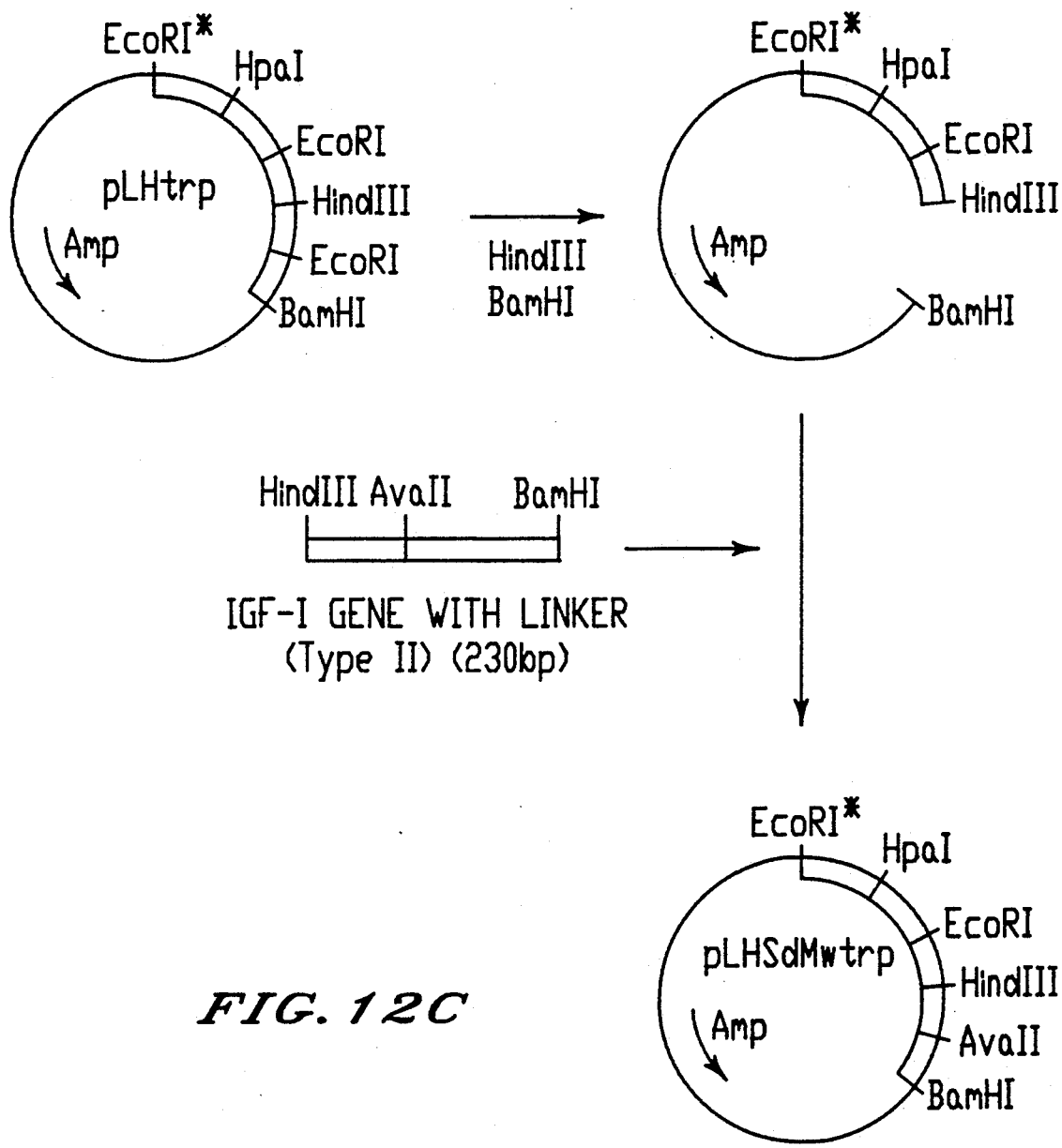
FIG. 12A, B, & C illustrate the construction of recombinant plasmid pLHSdMwtrp.

Plasmid pLHtrp prepared above was digested with HindIII and BamHI. The resultant large fragment was separated by preparative agarose gel electrophoresis. On the other hand, the IGF-I gene was isolated from plasmid pSdM1 prepared above with AvaII and BamHI, and oligonucleotides LA and LB were ligated upstream of and adjacent to it as a linker. The thus obtained IGF-I gene with linker was ligated with the above large fragment of plasmid pLHtrp. The mixture was transformed into *E. coli* HB101. The plasmid was isolated from one of the ampicillin resistant transformants obtained, and was confirmed to contain a gene coding for IGF-I fused with protein/peptide LH (Type II) by digestion with restriction enzyme and electrophoresis. The thus obtained plasmid was named plasmid pLHSdMwtrp. This process is shown in FIGS. 12(a), 12(b) and 12(c).

The thus obtained gene coding for IGF-I fused with protein/peptide LH (Type II) is as follows;

```
                    1
              EcoRI  Met  Cys  Tyr  Cys  Gln  Asp  Pro  Tyr
Coding:    5'-AATTC—ATG—TGT—TAC—TGC—CAG—GAC—CCA—TAT—
Noncoding:     3'-G—TAC—ACA—ATG—ACG—GTC—CTG—GGT—ATA—

10                                      20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                      HindIII      60
Ser  Gln  Ile  Val  Ser  Phe  Tyr  Phe  Lys  Leu  Glu  Val
AGC—CAA—ATT—GTC—TCC—TTT—TAC—TTC—AAG—CTT—GAA—GTA—
TCG—GTT—TAA—CAG—AGG—AAA—ATG—AAG—TTC—GAA—CTT—CAT—
```

-continued

```
                                            70
Trp  Gly  Pro  Glu  Thr  Leu  Cys  Gly  Ala  Glu  Leu  Val
TGG—GGT—CCT—GAA—ACT—CTG—TGC—GGC—GCT—GAA—CTG—GTT—
ACC—CCA—GGA—CTT—TGA—GAC—ACG—CCG—CGA—CTT—GAC—CAA—

80
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

90                                              100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

120
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

130
Lys  Ser  Ala  Stop  stop  BamHI
AAA—TCC—GCG—TGA—TAG-3'
TTT—AGG—CGC—ACT—ATC—CTAG-5',
``` and a gene coding for IGF-I fused with protein/peptide LH (Type II) is as follows:

```
                                  1
                                  Cys  Tyr  Cys  Gln  Asp  Pro  Tyr
           Coding:                5'-TGT—TAC—TGC—CAG—GAC—CCA—TAT—
           Noncoding:             3'-ACA—ATG—ACG—GTC—CTG—GGT—ATA—

10                                              20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                       HindIII    60
Ser  Gln  Ile  Val  Ser  Phe  Tyr  Phe  Lys  Leu  Glu  Val
AGC—CAA—ATT—GTC—TCC—TTT—TAC—TTC—AAG—CTT—GAA—GTA—
TCG—GTT—TAA—CAG—AGG—AAA—ATG—AAG—TTC—GAA—CTT—CAT—

70
Trp  Gly  Pro  Glu  Thr  Leu  Cys  Gly  Ala  Glu  Leu  Val
TGG—GGT—CCT—GAA—ACT—CTG—TGC—GGC—GCT—GAA—CTG—GTT—
ACC—CCA—GGA—CTT—TGA—GAC—ACG—CCG—CGA—CTT—GAC—CAA—

80
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

90                                              100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—
```

```
                    120
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

130
Lys  Ser  Ala
AAA—TCC—GCG
TTT—AGG—CGC
```

(c) Construction of an expression plasmid of a gene coding for IGF-I fused with protein/peptide LH (Type III)

Figure 13A:
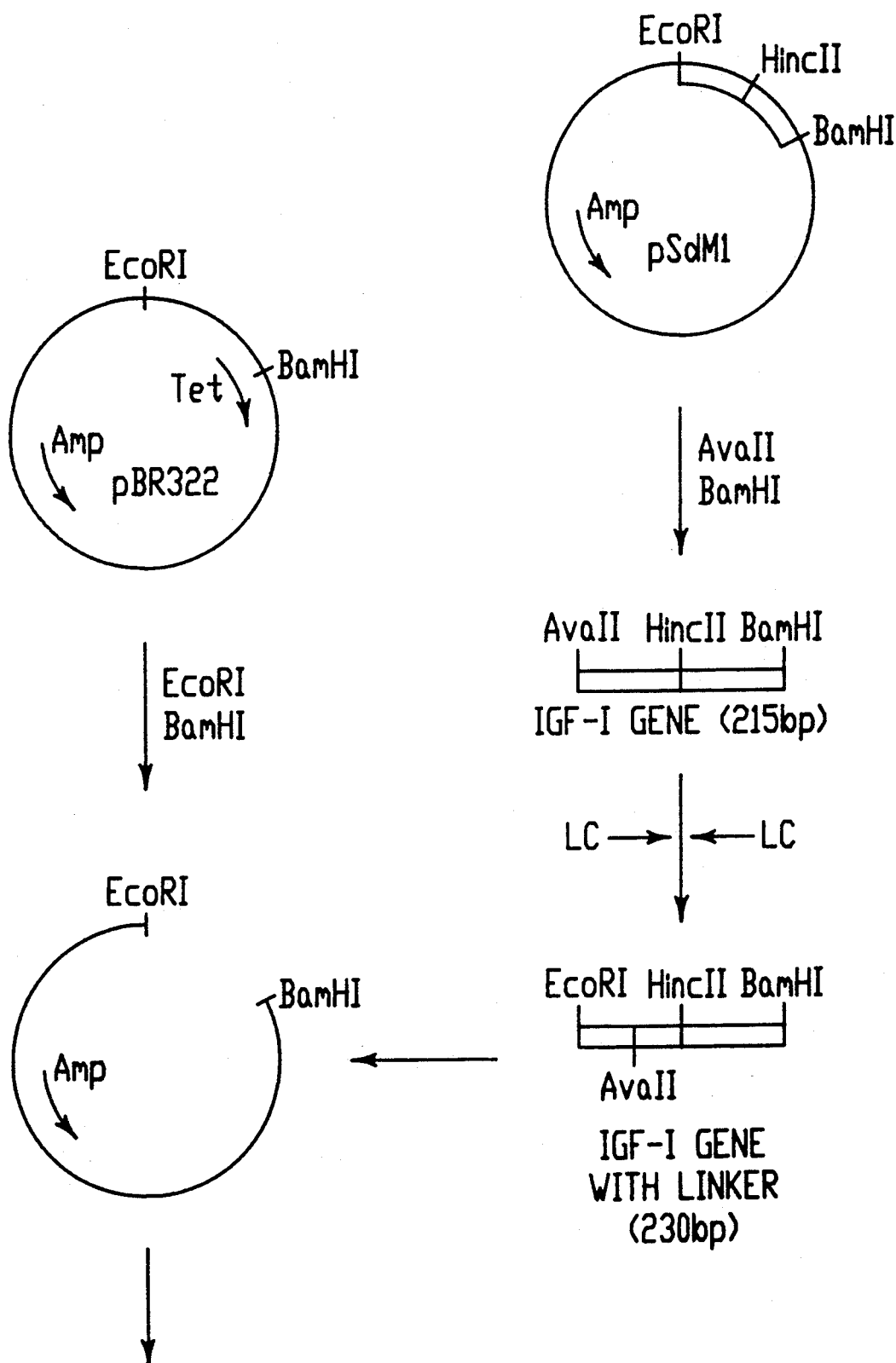
FIGS. 13A, B, & C illustrate the construction of recombinant plasmid pLHSdMctrp.
Figure 13C:
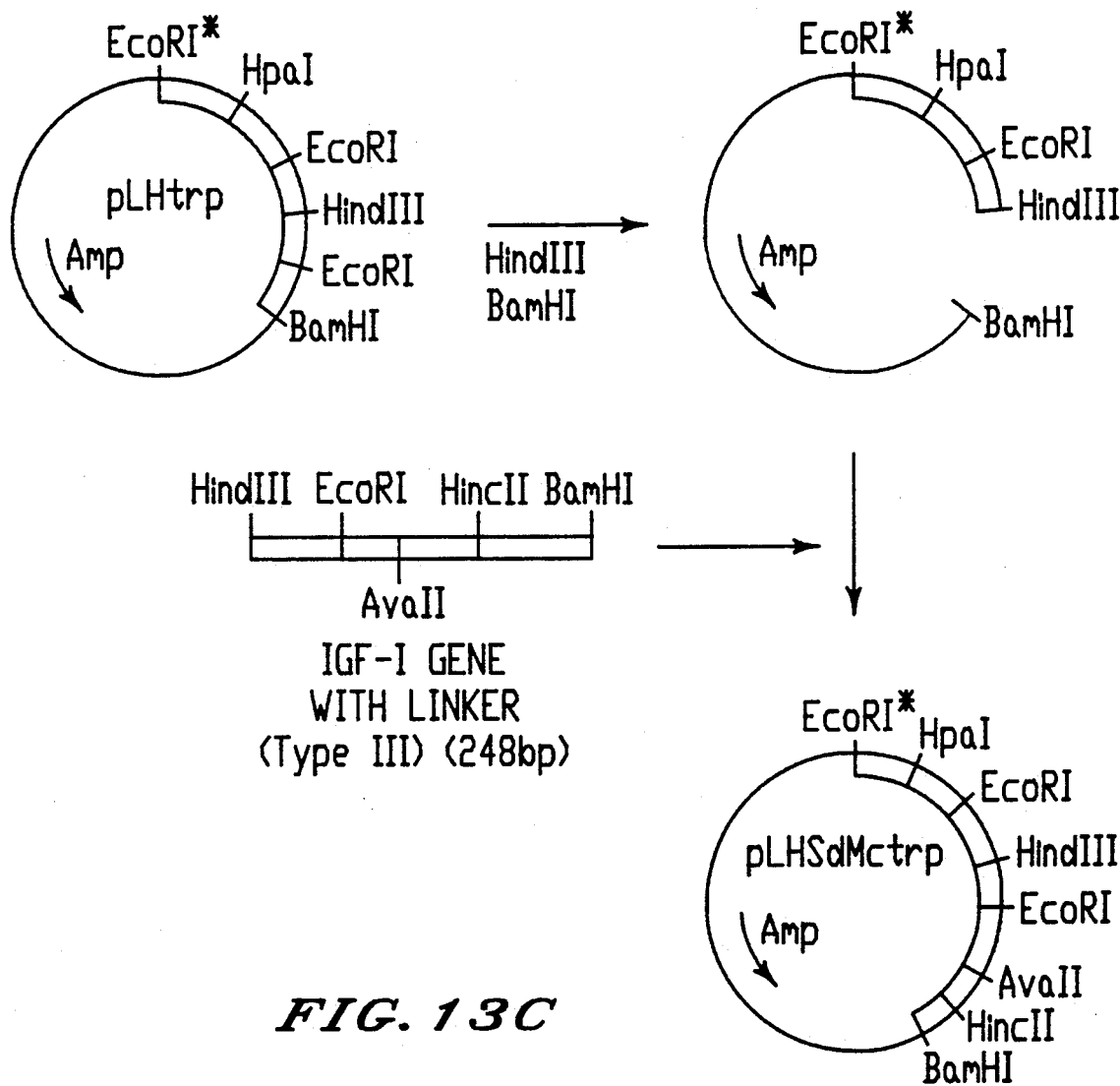

A plasmid pLHtrp prepared above was digested with HindIII and BamHI. The resultant large fragment was separated by preparative agarose gel electrophoresis. On the other hand, the IGF-I gene was isolated from plasmid pSdM1 prepared above with AvaII and BamHI, and oligonucleotides LC and LD were ligated upstream of and adjacent to it as a linker. The thus obtained IGF-I gene with linker was ligated with the large fragment of plasmid pBR322 digested with EcoRI and BamHi. The thus obtained plasmid pSdMc was digested again with EcoRI and BamHI. The thus obtained IGF-I gene with linker was ligated with the linker (m1 and m2 using a similar protocol to that used for the expression plasmid of Type I). Finally the obtained IGF-I gene obtained with two linkers was ligated to the above large fragment of plasmid pLHtrp. The mixtures was transformed into *E. coli* HB101. The plasmid was isolated from one of the ampicillin resistant and tetracycline sensitive transformants obtained and was confirmed to contain a gene coding for IGF-I fused with protein/peptide LH (Type III) by digestion with restriction enzyme and electrophoresis. The thus obtained plasmid was named plasmid pLHSdMctrp. This process is shown in FIGS. 13(a), 13(b) and 13(c).

The thus obtained gene coding for IGF-I fused with protein/peptide LH (Type III) is as follows:

```
                           1
                EcoRI   Met  Cys  Tyr  Cys  Gln  Asp  Pro  Tyr
      Coding:    5'-AATTC—ATG—TGT—TAC—TGC—CAG—GAC—CCA—TAT—
      Noncoding:       3'-G—TAC—ACA—ATG—ACG—GTC—CTG—GGT—ATA—

10                                              20
Val   Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                 HindIII    60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

Glu  Phe  Gly  Pro  Ala
GAA—TTC—GGC—CCC—GCG—
CTT—AAG—CCG—GGG—CGC—

70
Gly  Pro  Glu  Thr  Leu  Cys  Gly  Ala  Glu  Leu  Val
GGT—CCT—GAA—ACT—CTG—TGC—GGC—GCT—GAA—CTG—GTT—
CCA—GGA—CTT—TGA—GAC—ACG—CCG—CGA—CTT—GAC—CAA—

80                                        90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110                                         120
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—
```

-continued

```
                            130
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

Lys  Ser  Ala  Stop stop BamHI
AAA—TCC—GCG—TGA—TAG-3'
TTT—AGG—CGC—ACT—ATC—CTAG-5',
``` and a gene coding for IGF-I fused with protein/peptide LH (Type III) is as follows:

In a suitable embodiment of this invention, the following DNA fragment which had the SD sequence of a

```
                        1
                        Cys  Tyr  Cys  Gln  Asp  Pro  Tyr
           Coding:      5'-TGT—TAC—TGC—CAG—GAC—CCA—TAT—
           Noncoding:   3'-ACA—ATG—ACG—GTC—CTG—GGT—ATA—

10                                              20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                HindIII   60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

Glu  Phe  Gly  Pro  Ala
GAA—TTC—GGC—CCC—GCG—
CTT—AAG—CCG—GGG—CGC—

70
Gly  Pro  Glu  Thr  Leu  Cys  Gly  Ala  Glu  Leu  Val
GGT—CCT—GAA—ACT—CTG—TGC—GGC—GCT—GAA—CTG—GTT—
CCA—GGA—CTT—TGA—GAC—ACG—CCG—CGA—CTT—GAC—CAA—

80                                       90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110                                         120
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

130
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

Lys  Ser  Ala
AAA—TCC—GCG
TTT—AGG—CGC
```

(d) Construction having an expression plasmid of a polycistronic gene coding for fused IGF-I (i) Preparation of DNA fragment having SD sequence of a promoter upstream of a fused IGF-I gene To construct an expression plasmid of a polycistronic gene coding for fused IGF-I, a fragment having the sequence upstream of a fused IGF-I gene was prepared. synthetic trp promoter I gene upstream of a gene coding for the IGF-I gene with protein/peptide LH gene and to which BamHI sites were introduced at the 5' end and 3' end, was selected.

Further, a methionine codon (ATG) was inserted upstream of and adjacent to N-terminal amino acid codon of protein/peptide LH and two stop condons (TGA and TAG) was inserted downstream of and adjacent to the c-terminal codon of IFG-I.

The sequence of the DNA fragment (464 bp) is as follows:

```
5'GATCCGTC—AACTAGTACGCAAGTTCACGTAAA—
3'CTAGGCAG—TTGATCATGCGTTCAAGTGCATTT—

EcoRI
             Met  Cys  Tyr  Cys  Gln  Asp  Pro  Tyr
AAGGGTATCGAATTC—ATG—TGT—TAC—TGC—CAG—GAC—CCA—TAT—
TTCCCATAGCTTAAG—TAC—ACA—ATG—ACG—GTC—CTG—GGT—ATA—

Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

Leu  Lys  Asn  Trp  Lys  Glu  Glu  Ser  Asp  Arg  Lys  Ile  Met  gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

HindIII    60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

Glu  Phe  Met  Gly  Pro  Glu  Thr  Leu  Cys  Gly  Ala  Glu  Leu  Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—

Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT—

BamHI
Lys  Ser  Ala  Stop  stop
AAA—TCC—GCG—TGA—TAG-3'
TTT—AGG—CGC—ACT—ATC—CTAG-5'
```

(ii) Construction of an expression plasmid of a polycistronic gene coding for a fused IGF-I Plasmid pLHSdMmtrp was digested with BamHI. The DNA fragment of a plasmid pLHSdMmtrp was obtained to give an expression plasmid of a polycistronic gene coding for fused IGF-I. This process is shown in FIGS. 14(a), 14(b), 15(a), 15(b) and 15(c).

[6] Expression of the IGF-I Gene in a Host Organism

For the expression of the IGF-I gene(s), the thus obtained plasmid having a promoter gene and IGF-I gene was transformed into a host organism. Then the host organism having the plasmid was cultured in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, sucrose, glycerin, starch and the like. Other sources, which may be included are xylose, galactose, maltose, dextrin, lactose and the like.

The preferred sources of nitrogen are yeast extract, peptone, gluten meal, cottonseed flour, soybean meal, corn steep liquor, dried yeast, wheat germ, etc., as well as inorganic and organic nitrogen compounds such as ammonium nitrate, ammonium sulfate, ammonium phosphate, etc.), urea, amino acid and the like.

The carbon and nitrogen sources, though advantageously employed in combination, need not be used in their pure form, because less pure materials which contain traces of growth factors and considerable quantities cf mineral nutrients, are also suitable for use. When desired, there may be added to the medium mineral salts such as calcium carbonate, sodium or potassium phosphate, sodium or potassium chloride, magnesium salts, copper salts and the like.

Agitation and aeration of the culture mixture may be accomplished in a variety of ways. Agitation may be provided by a propeller or similar mechanical agitation equipment, by revolving or shaking the fermentor, by various passing equipment or by the passage of sterile air through the medium. Agitation may be effected by passing sterile air through the fermentation mixture.

The fermentation is usually conducted at a temperature between about 20° C. and 42° C., preferably 35°-38° C., for a period of several hours to 50 hours.

The thus produced IGF-I or fused IGF-I can be recovered from the cultured medium by conventional means which are commonly used for the recovery of other known biologically active substances. In general, the IGF-I or fused IGF-I produced is found in the cells of the host organisms. Accordingly the IGF-I or fused IGF-I can be separated from the cells, by filtering or centrifuging the cultured broth, or by another conventional method such as concentration under reduced pressure, lysis such as sonication, HPLC, lyophilization, pH adjustment, treatment with a resin (e.g. anion or cation exchange resin, non-ionic adsorption resin), treatment with a conventional adsorbent (e.g. activated carbon, silicic acid, silica gel, cellulose, almina), gel filtration, crystallization, and the like.

(1) Expression of the IGF-I gene in *E. coli* using plasmid pSdM1-322trp

An overnight culture of *E coli* HB101 containing plasmid pSdM1-322trp in L broth was diluted in M9 medium lacking tryptophan, and the cells were incubated at 37° C. for 3 hours under β-indoleacrylic acid induction conditions. Detection of IGF-I production was carried out using a radioimmunoassay (hereinafter referred to as RIA) with the antibody of IGF-I fragment (26-46) using N. Yanaihara's method [N.

medium. IGF-I fused with protein/peptide LH (Type I) was isolated from the resulting culture broth.

(i) Expression of a gene coding for IGF-I fused with protein/peptide LH (Type I) in *E. coli* using plasmid pLHSdMmtrp An overnight culture of *E. coli* HB101 containing pLHSdMmtrp in L broth was diluted in M9 medium lacking tryptophan, and the cells were incubated at 37° C. for 3 hours under the condition of β-indoleacrylic acid induction. Detection of the fused IGF-I production was carried out using a RIA with the antibody of IFG-I fragment (26-46) using N. Yanaihara's method.

(ii) Isolation of IGF-I fused with protein/peptide LH (Type I)

The culture fluid was centrifuged to give a wet cell paste, and the culture cells were lysed by sonication. The pellet was collected by centrifugation and the dissolved in 8M urea solution containing 0.1 M dithiothreitol (hereinafter referred to as DTT). After centrifugation the solution was purified by Sephacryl 300 column chromatography. Active fractions detected by RIA were collected and dialysed to give a protein which contained the desired component. The fused IGF-I was detected at its normal position (15500) on polyacrylamide gel electrophoresis.

The thus obtained IGF-I fused with protein/peptide LH (Type I) had the following sequence

```
  1                                                                10
Cys—Tyr—Cys—Gln—Asp—Pro—Tyr—Val—Lys—Glu—Ala—Glu—Asn—Leu—

20
Lys—Lys—Tyr—Phe—Asn—Ala—Gly—His—Ser—Asp—Val—Ala—Asp—Asn—

30                                    40
Gly—Thr—Leu—Phe—Leu—Gly—Ile—Leu—Lys—Asn—Trp—Lys—Glu—Glu—

50
Ser—Asp—Arg—Lys—Ile—Met—Gln—Ser—Gln—Ile—Val—Ser—Phe—Tyr—

60                                        70
Phe—Lys—Leu—Glu—Val—Lys—His—Glu—Phe—Met—Gly—Pro—Glu—Thr—

80
Leu—Cys—Gly—Ala—Glu—Leu—Val—Asp—Ala—Leu—Gln—Phe—Val—Cys—

90
Gly—Asp—Arg—Gly—Phe—Tyr—Phe—Asn—Lys—Pro—Thr—Gly—Tyr—Gly—

100                                      110
Ser—Ser—Ser—Arg—Arg—Ala—Pro—Gln—Thr—Gly—Ile—Val—Asp—Glu—

120
Cys—Cys—Phe—Arg—Ser—Cys—Asp—Leu—Arg—Arg—Leu—Glu—Met—Tyr—

130
Cys—Ala—Pro—Leu—Lys—Pro—Ala—Lys—Ser—Ala
```

Yanaihara et al, Peptide Hormones in Pancreas 3, 28(1983)]..

[7] Expression of a Fused IGF-I Gene in a Host Organism: (1) Expression of a gene coding for IGF-I gene fused with protein/peptide LH (Type I) in a host organism For the expression of a gene coding for IGF-I fused with protein/peptide LH (Type I), the thus obtained plasmid having a promoter gene and a gene coding for IGF-I fused with protein/peptide LH (Type I) was transformed into a host organism, and then the host organism having the plasmid was cultured in a suitable (2) Expression of a gene coding for IGF-I fused with protein/peptide LH (Type II) in a host organism (i) Expression of a gene coding for IGF-I fused with protein/peptide LH (Type II) in *E. coli* using plasmid pLHSdMwtrp This process can be conducted according to a manner similar to that outlined above for the expression of a gene coding for IGF-I fused with protein/peptide LH (Type I).

(ii) Isolation of IGF-I fused with protein peptide LH (Type II)

This process can be conducted according using a similar to that used for the isolation of IGF-I fused with protein/peptide LH (Type I).

The thus obtained IGF-I fused with protein/peptide LH (Type II) had the following sequence:

```
1                                                           10
Cys—Tyr—Cys—Gln—Asp—Pro—Tyr—Val—Lys—Glu—Ala—Glu—Asn—Leu—
                         20
Lys—Lys—Tyr—Phe—Asn—Ala—Gly—His—Ser—Asp—Val—Ala—Asp—Asn—
     30                                      40
Gly—Thr—Leu—Phe—Leu—Gly—Ile—Leu—Lys—Asn—Trp—Lys—Glu—Glu—
                              50
Ser—Asp—Arg—Lys—Ile—Met—Gln—Ser—Gln—Ile—Val—Ser—Phe—Tyr—
              60
Phe—Lys—Leu—Glu—Val—Trp—Gly—Pro—Glu—Thr—
              70                                       80
Leu—Cys—Gly—Ala—Glu—Leu—Val—Asp—Ala—Leu—Gln—Phe—Val—Cys—
                                   90
Gly—Asp—Arg—Gly—Phe—Tyr—Phe—Asn—Lys—Pro—Thr—Gly—Tyr—Gly—
                       100
Ser—Ser—Ser—Arg—Arg—Ala—Pro—Gln—Thr—Gly—Ile—Val—Asp—Glu—
110                                  120
Cys—Cys—Phe—Arg—Ser—Cys—Asp—Leu—Arg—Arg—Leu—Glu—Met—Tyr—
                   130
Cys—Ala—Pro—Leu—Lys—Pro—Ala—Lys—Ser—Ala
```

(3) Expression of a gene coding for IGF-I fused with protein/peptide LH (Type III) in a host organism (i) Expression of a gene coding for IGF-I fused with protein/peptide LH (Type III) in *E. coli* using plasmid pLHSdMctrp This process can be conducted using a manner similar to that used for the expression of a gene coding for IGF-I fused with protein/peptide LH (Type I).

(ii) Isolation of IGF-I fused with protein/peptide LH (Type III)

This process can be conducted using a manner similar to that used for the isolation of IGF-I fused with protein/peptide LH (Type I).

The thus obtained IGF-I fused with protein/peptide LH (Type III) had the following sequence

```
1                                                           10
Cys—Tyr—Cys—Gln—Asp—Pro—Tyr—Val—Lys—Glu—Ala—Glu—Asn—Leu—
                         20
Lys—Lys—Tyr—Phe—Asn—Ala—Gly—His—Ser—Asp—Val—Ala—Asp—Asn—
     30                                      40
Gly—Thr—Leu—Phe—Leu—Gly—Ile—Leu—Lys—Asn—Trp—Lys—Glu—Glu—
                              50
Ser—Asp—Arg—Lys—Ile—Met—Gln—Ser—Gln—Ile—Val—Ser—Phe—Tyr—
              60
Phe—Lys—Leu—Glu—Val—Lys—His—Glu—Phe—
         70
Gly—Pro—Ala—Gly—Pro—Glu—Thr—
                                                 80
Leu—Cys—Gly—Ala—Glu—Leu—Val—Asp—Ala—Leu—Gln—Phe—Val—Cys—
              90                                      100
Gly—Asp—Arg—Gly—Phe—Tyr—Phe—Asn—Lys—Pro—Thr—Gly—Tyr—Gly—
                                 110
Ser—Ser—Ser—Arg—Arg—Ala—Pro—Gln—Thr—Gly—Ile—Val—Asp—Glu—
                   120
Cys—Cys—Phe—Arg—Ser—Cys—Asp—Leu—Arg—Arg—Leu—Glu—Met—Tyr—
```

130
Cys—Ala—Pro—Leu—Lys—Pro—Ala—Lys—Ser—Ala (4) Expression of a polycistronic gene coding for a fused IGF-I in a host organism (i) Expression of a polycistronic gene coding for fused IGF-I in *E. coli* using plasmid pLS-T2 or pLS-T3

This process can be conducted using a manner similar to that used for the expression of a gene coding for IGF-I fused with protein/peptide LH (Type I).

(ii) Isolation of IGF-I fused with protein/peptide LH

The thus obtained IGF-I fused with protein/peptide LH is the same to the IGF-I fused with protein/peptide LH (Type I).

[8] Conversion of Fused IGF-I to IGF-I and Isolation of IGF-I

The thus obtained fused IGF-I can be converted to IGF-I by cleavage reaction of the fused IGF-I to separate IGF-I from the protective peptide.

This cleavage reaction can be conducted in accordance with conventional methods used in the field of peptide chemistry. Suitable cleavage reaction conditions can be selected according to the type of fused IGF-I.

Suitable agent used in this cleavage reaction may include cyanogen bromide; BNPS-skatole or NCS; collagenase and the like.

This cleavage reaction is usually carried out under mild conditions in a conventional solvent which does not adversely affect the reaction.

The reaction temperature is not critical and the reaction is usually conducted from cooling to warming.

The cleavage reactions which can be applied to the most preferable three types of fused IGF-I are hereinafter described in detail.

(1) Cleavage of the protein/peptide from IGF-I fused with the protein/peptide through methionine residue of the protein/peptide IGF-I fused with a protein/peptide through methionine residue of the protein/peptide can be converted to IGF-I by cleavage reaction with cyanogen bromide.

In this case, although IGF-I has methionine residue in the 59th position of its amino acid sequence, cleavage at the amide bond linking the 59th methionine and the 60th tyrosine of IGF-I follows cleavage at the amide bond linking the methionine in front of the 1st amino acid of IGF-I and the 1st amino acid of IGF-I, glycine. This phenomena, the order of cleavage at the bond neighboring methionine residue has been discovered by the inventors for the first time. According to this phenomena, protein/peptide can be removed easily by cyanogen bromide mediated cleavage reaction of the fused IGF-I if suitable conditions are selected.

This reaction is usually carried out under mild conditions in a conventional solvent which does not adversely affect the reaction.

The reaction temperature is not critical and the reaction is usually carried out from cooling to warming.

Cleavage of protein/peptide LH from fused IGF-I with protein/peptide LH through methionine residue of protein/peptide LH (Type I)

The fused IGF-I was treated with cyanogen bromide in 60% formic acid at 25° C. for 3 hours. After lyophilization the residue was dissolved in an 8 M urea solution containing 50 mM 2-mercaptoethanol and dialyzed to give a crude mixture of reduced IGF-I. The mixture was purified by cationic ion exchange chromatography (CM52). Active fractions detected by RIA were collected and dialysed. The dialysed fractions were subjected to high performance liquid chromatography to give a pure reduced IGF-I. The reduced IGF-I was converted to oxidized IGF-I by the usual manner of refolding. The purified IGF-I showed a single bard on polyacrylamide gel electrophoresis (PAGE), and the IGF-I was identical with authentic IGF-I gift of Dr. Humbel) on HPLC. The amino acid sequence the IGF-I was determined by a combination of Edman's method and the carboxypeptidase method. The IGF-I showed biological activity in [$^3$H]-thymidine incorporation assay of mouse BALB/c 3T3 cells.

(2) Elimination of the protein/peptide from IGF-I fused with the protein/peptide through tryptophan of the protein/peptide IGF-I fused with a protein/peptide through tryptophan of the protein/peptide can be converted to IGF-I by elimination reaction with BNPS-skatole or NCS.

This reaction is usually carried out under mild conditions in a conventional solvent which does not adversely affect the reaction.

The reaction temperature is not critical and the reaction is usually carried out from cooling to warming.

Cleavage of protein/peptide LH from the IGF-I fused with protein/peptide LH through a tryptophan residue of protein/peptide LH (Type II)

The fused IGF-I was treated with BNPS-skatole in 70% acetic acid or NCS in urea. After the reaction, the mixture was treated with 2-mercaptoethanol and then purified by reverse phase HPLC (RPSC column) to give a IGF-I sulfoxide. The IGF-I sulfoxide was treated with 5 M thioglycolic acid at 50° C. After addition of 6 M guanidine and 2-mercaptoethanol, the mixture was purified by reverse phase HPLC (RPSC column) to give a pure reduced IGF-I. The reduced IGF-I was identified with that obtained by cleavage reaction of IGF-I fused with protein/peptide LH (Type I).

(3) Cleavage of the protein/peptide from IGF-I fused with the protein/peptide through "-Gly-Pro-Ala-" of the protein/peptide IGF-I fused with the protein/peptide through "-Gly-Pro-Ala-" of the protein/peptide can be converted to IGF-I by cleavage reaction with collagenase.

The reaction is usually carried out under mild conditions in a conventional solvent which does not adversely affect the reaction.

The reaction temperature is not critical and the reaction is usually carried out from cooling to warming.

Cleavage of protein/peptide LH from IGF-I fused with protein/peptide LH through "-Gly-Pro-Ala-" of protein/peptide LH (Type III)

The fused IGF-I was treated with collagenase in 2.4 M urea or 2 M guanidine HCl at 30° C. for 18 hours. After addition of DTT to the reaction mixture, it was analyzed by HPLC (RPSC column) to detect a peak corresponding to reduced IGF-I.

[9] RIA of IGF-I

RIA of IGF-I was followed by the method established by N. Yanaihara. With 0.1 ml of the above sample or standard sample (IGF-I fragment (26–46)) sample buffer [0.5% bovine serum albumin (hereinafter referred to as BSA) in 0.01 M phosphate buffer saline (hereinafter referred to as PBS), 0.025 M EDTA (pH 7.4) (0.4 ml)], rabbit antiserum (0.1 ml) of IGF-I (26–46) and $^{125}$I-IGF-I (26–46) (0.1 ml) were mixed. The mixture was allowed to stand for 48 hours at 4° C., and then added with rabbit serum (0.1 ml), rabbit γ-globulin antiserum (0.1 ml) and 5% PEG6000 (0.9 ml). After standing for additional 2 hours at 4° C. the pellet was collected by centrifugation (3 krpm, 4° C., 30 minutes). Radioactivity was measured by γ-counter. The content of IGF-I was calculated from this radioactivity.

[10] Biological Assay of IGF-I

Mouse BALB/c 3T3 embryofibroblasts (clone A31) were trypsinized and resuspended at a concentration of $10^5$ cells/ml in Dulbecco-Vogt Modified Eagle's medium containing 10% New Born Calf Serum and 25 mM N-(2-hydroxyethyl)piperazine-N'-2-ethanesulfonic acid (HEPES). Aliquots of 100 μl were plated into 0.3 cm$^2$ wells(96 well-microtiter plate, Costor). Three to four days after the cells reached confluence (5–7 days after initial plating) the spent medium was removed and the culture was washed three times and then 0.2 μCi/well [$^3$H]thymidine (0.67 Ci/mmole) plus test samples were added. After incubation for 24 hours, the medium was removed and the cells were washed with PBS and trypsinized for determination of radioactivity. Cells were trapped in glass filters by use of semi automatic multiple cell harvester (LAVO MASH, LABO SCIENCE). Incorporated [$^3$H]thymidine was counted in 8 ml of Aquazol 2 (New England Nuclear) using a Packard Tri-Carb Liquid Scintillation Counter.

The following examples are given for the purpose of illustrating the present invention.

EXAMPLE 1

Synthesis of
HOApApApCpCpGpApCpCpGpGpCpTpApTpGOH (G1).

(1) Synthesis of
DMTrOTpoA$^{Bz}$poTpoG$^{iB}$po$^{Ac}$Upo-cellulose i) Preparation of HOG$^{iB}$po$^{Ac}$Upo-cellulose To a suspension of DMTrOG$^{iB}$po$^{Ac}$Upo-cellulose (130.4 mg, 4.59 μmole*) (prepared by R. Crea's method[1])) in methanol/CHCl$_3$ (1:9 v/v, 5.0 ml), TCA/CHCl$_3$ (2:8 w/v, 5.0 ml) was added under ice cooling, and the mixture was stirred at 0° C. for 10 min. After being washed with CHCl$_3$ (2 ml) and methanol (6.0 ml), successively, on the filter, the cellulose adduct (HOG$^{iB}$po$^{Ac}$Upo-cellulose) was dried, water being separated as the pyridine (2 ml) azeotrope.

* This value was calculated by monitoring the absorbance of a washing solution with CHCl$_3$ at 507 nm.
1) R. Crea et al, Nucleic Acid Res. 8, 2331(1980)

ii) Preparation of DMTrOTpoA$^{Bz}$poTpo$^-$

DMTrOTpoA$^{Bz}$poTpo-CE (39.9 mg, 23.0 μmole) was treated with Et$_3$N-CH$_3$CN (1:1 v/v, 5 ml) at room temperature for 1 hr. The phosphodiester trimer (DMTrOTpoA$^{Bz}$poTpo$^-$) so obtained was dried, water being separated as the pyridine azeotrope (0.5 ml, 2×1 ml).

iii) Coupling

The trimer (DMTrOTpoA$^{Bz}$poTpo$^-$) was mixed with the cellulose adduct (HOG$^{iB}$po$^{Ac}$Upo-cellulose) in a 10 ml round-bottom flask. The mixture was dried, water being separated as the pyridine azeotrope (2×1 ml) and finally resuspended in anhydrous pyridine (1 ml). Mesitylen sulfonyl nitrotriazolide (MSNT) (68.0 mg, 230 μmole) was added to the suspension and the mixture was stirred at room temperature for 1 hr. And then pyridine was added to the reaction vessel and cellulose adduct was recovered by centrifugation (3,000 rpm, 2 min).

iv) Acetylation of unreacted 5'hydroxy groups

The cellulose adduct obtained as above was suspended in a solution of pyridine-acetic anhydride (10:1 v/v, 5.5 ml) and stirred at room temperature for 30 min. The cellulose-product (113.9 mg) was obtained by repeated centrifugation (3,000 rpm, 2 min) in pyridine (5 ml), washing with methanol (15 ml) and drying in vacuo at room temperature for 30 minutes. The cellulose adduct (DMTrOTpoA$^{Bz}$poTpoG$^{iB}$po$^{Ac}$Upo-Cellulose) can be used for the next coupling step.

(2) Synthesis of
DMTrOG$^{iB}$poG$^{iB}$poC$^{Bz}$poTpoA$^{Bz}$poTpoG$^{iB}$po-$^{Ac}$Upo-cellulose DMTrOG$^{iB}$poG$^{iB}$poC$^{Bz}$poTpoA$^{Bz}$poTpoG$^{iB}$po$^{Ac}$Upo-cellulose was synthesized from DMTrOTpoA$^{Bz}$poTpoG$^{iB}$po$^{Ac}$Upo-cellulose (113.9 mg) and DMTrOG$^{iB}$poG$^{iB}$poC$^{Bz}$po-CE (43.7 mg) according to similar conditions similar to those set out above.

(3) Synthesis of
DMTrOA$^{Bz}$poC$^{Bz}$poC$^{Bz}$poG$^{iB}$poG$^{iB}$poC$^{Bz}$poTpoA$^{Bz}$poTpoG$^{iB}$po$^{Ac}$Upo-Cellulose DMTrOA$^{Bz}$poC$^{Bz}$poC$^{Bz}$poG$^{iB}$poG$^{iB}$poC$^{Bz}$poTpoA$^{Bz}$poTpoG$^{iB}$po$^{Ac}$Upo-cellulose (105.8 mg) was synthesized from DMTrOG$^{iB}$poG$^{iB}$poC$^{Bz}$poTpoA$^{Bz}$poTpoG$^{iB}$po$^{Ac}$Upo-cellulose (109.5 mg) and DMTrOA$^{Bz}$poC$^{Bz}$poC$^{Bz}$po-CE (44.0 mg) according to similar conditions.

(4) Synthesis of
DMTrOC$^{Bz}$poC$^{Bz}$poG$^{iB}$poA$^{Bz}$poC$^{Bz}$poC$^{Bz}$poG$^{iB}$po-G$^{iB}$poC$^{Bz}$poTpoA$^{Bz}$poTpoG$^{iB}$po$^{Ac}$Upo-cellulose DMTrOC$^{Bz}$poC$^{Bz}$poG$^{iB}$poA$^{Bz}$poC$^{Bz}$poC$^{Bz}$poG$^{iB}$poG$^{iB}$poC$^{Bz}$poTpoA$^{Bz}$poTpoG$^{iB}$po$^{Ac}$Upo-cellulose (94.5 mg) was synthesized from DMTrOA$^{Bz}$poC$^{Bz}$poC$^{Bz}$poG$^{iB}$poG$^{iB}$poC$^{Bz}$poTpoA$^{Bz}$poTpoG$^{iB}$po$^{Ac}$Upo-cellulose (105.8 mg) and DMTrOC$^{Bz}$poC$^{Bz}$poG$^{iB}$po-CE (43.5 mg) according to similar conditions.

(5) Synthesis of
DMTrOA$^{Bz}$poA$^{Bz}$poA$^{Bz}$poC$^{Bz}$poC$^{Bz}$poG$^{iB}$poA$^{Bz}$poC$^{Bz}$poC$^{Bz}$poG$^{iB}$poG$^{iB}$poC$^{Bz}$poTpoA$^{Bz}$poTpoG$^{iB}$po$^{Ac}$Upo-cellulose DMTrOA$^{Bz}$poA$^{Bz}$poA$^{Bz}$poC$^{Bz}$poC$^{Bz}$poG$^{iB}$poA$^{Bz}$poC$^{Bz}$poC$^{Bz}$poG $^{iB}$poG$^{iB}$poC$^{Bz}$poTpoA$^{Bz}$poTpoG$^{iB}$po$^{Ac}$Upo-cellulose (90.4 mg) was synthesized from DMTrOC$^{Bz}$poC$^{Bz}$poG$^{iB}$poA$^{Bz}$poC$^{Bz}$poC $^{Bz}$poG$^{iB}$poG$^{iB}$poC$^{Bz}$poTpoA$^{Bz}$poTpoG$^{iB}$po$^{Ac}$Upo-Cellulose (94.5 mg) and DMTrOA$^{Bz}$poA$^{Bz}$poA$^{Bz}$po-CE (45.1 mg) under similar conditions. At this final process, it was not necessary to protect the unreacted 5'-hydroxy group with an acetyl group.

(6) Synthesis of HOApApApCpCpGpApCpCpGpGpCpTpApTpGOH

DMTrOA$^{Bz}$poA$^{Bz}$poA$^{Bz}$poC$^{Bz}$poC$^{Bz}$poG$^{iB}$poA$^{Bz}$poC$^{Bz}$poC$^{Bz}$poG $^{iB}$poG$^{iB}$poC$^{Bz}$poTpoA$^{Bz}$poTpoG$^{iB}$po$^{Ac}$Upo-cellulose (90.4 mg) was treated with 0.5 M N,N,N',N'-tetramethylguanidinium pyridine 2-aldoximate (in dioxane-H$_2$O (1:1 v/v, 1 ml)) at 20° C. for 20 hrs in a sealed tube. To the reaction mixture 28% (w/w) aqueous ammonia (12 ml) was added, and the mixture was heated at 60° C. for 2 hrs. The solid cellulose was removed by filtration and washed with water (10 ml). The filtrate and washed solution were evaporated to dryness, and the residue was treated with 80% aqueous acetic acid (25 ml) at room temperature for 15 mins. After removal of the solvents, the residue was dissolved in 0.1 M triethylammonium carbonate buffer (pH 7.5, 25 ml) was washed with diethylether (3×25 ml). The aqueous layer was evaporated to dryness and the residue was dissolved in 0.1 M triethylammonium carbonate buffer (pH 7.5, 2 mins) to yield crude HOApApApCpCpGpApCpCpGpGpCpTpApTpGOH in the solution.

(7) Purification of HOApApApCpCpGpApCpCpGpGpCpTpApTpGOH i) First purification of the crude product was performed by column chromatography on Biogel P2 (24×2.6 cm ID). The fractions corresponding to the first eluted peak (50 mM NH$_4$OAc, 0.1 mM EDTA, 1 ml/min) were collected and freeze-dried to give the first purified product.

ii) Second purification of the first purified product was performed by HPLC on CDR-10 (25 cm×4.6 mm ID) using a linear gradient of 1M NH$_4$OAc-10% (v/v) aqueous ethanol to 4.5 M NH$_4$OAc-10% (v/v) aqueous ethanol (80 min, 1 ml/min, 60° C. to give the second purified product.

iii) Third purification of the second purified product was performed by reverse phase HPLC (RP-18-5μ(x77), 15 cm ×4 mm ID) using a linear gradient of 0.1 M NH$_4$OAc to 0.1 M NH$_4$OAc 15% (v/v) aqueous CH$_3$CN (40 min, 1.5 ml/min, room temperature) to give the final purified product (HOApApApCpCpGpApCpCpGpGpCpTpApTpGOH).

This process is shown in FIGS. 1 and 2.

(8) Analysis of oligonucleotide (HOApApApCpCpGpApCpCpGpGpCpTpApTpGOH)

i) Digestion by phosphodiesterase

The mixture of HOApApACpCpGpApCpCpGpGpCpTpApTpGOH (5 μg, 61.7 μl), 0.2 M MgCl$_2$ (10 μl), 0.2 M Tris-HCl (pH 8.5) (10 μl) and 0.1 mM EDTA in an aqueous solution (13.3 μl) was treated with phosphodiesterase (5 unit, 5 μl) at 37° C. for 20 min, and then heated at 100° C. for 2 min. ii) Analysis by HPLC The oligonucleotide in the reaction mixture was analyzed by HPLC (CDR-10, 25 cm×4.6 mm ID) using a linear gradient of water to 2.0 M NH$_4$OAc (pH 3.4) (40 min, 1.5 ml/min, 60° C.). From each peak area observed, its nucleotide composition was determined comparing with the peak area of a standard sample.

Calcd: pC$_{OH}$ 5,000, pA$_{OH}$ 4,000, pT$_{OH}$ 2,000, pG$_{OH}$ 4,000 Observed: pC$_{OH}$ 4,767, pA$_{OH}$ 4,127, pT$_{OH}$ 2,054, pG$_{OH}$ 4,052

EXAMPLE 2

Synthesis of oligonucleotides (A1, A2, B1, B2, C1, C2, D1, D2, E1, E2, F1, F2, G2, H1, H2, I1, I2, J1, J2, K1, K2, L1, L2, M1, M2, N1, N2, O1 and O2)

The following oligonucleotides were prepared using a procedure similar to that used for G1 described in Example 1.
(1) HOApApTpTpCpApTpGpGpGpTOH (A1)
(2) HOTpTpTpCpApGpGpApCpCpCpApTpGOH (A2)
(3) HOCpCpTpGpApApApCpTpCpTpGpTpGOH (B1)
(4) HOCpApGpCpGpCpCpGpCpApCpApGpApGOH (B2)
(5) HOCpGpGpCpGpCpTpGpApApCpTpGpGpTOH (C1)
(6) HOApGpApGpCpGpTpCpApApCpCpApGpTpTOH (C2)
(7) HOTpGpApCpGpCpTpCpTpGpCpApApApTpTpTOH (D1)
(8) HOCpCpApCpApTpApCpApApApApTpTpGpCOH (D2)
(9) HOGpTpApTpGpTpGpGpTpGpApTpCpGpTOH (E1)
(10) HOTpApGpApApApCpCpApCpGpApTpCpAOH (E2)
(11) HOGpGpTpTpTpCpTpApCpTpTpCpApApCOH (F1)
(12) HOGpGpTpCpGpGpTpTpTpGpTpTpGpApApGOH (F2)
(13) HOGpCpTpGpGpApGpCpCpApTpApGpCpCOH (G2)
(14) HOGpCpTpCpCpApGpCpTpCpTpCpGpTpCOH (H1)
(15) HOCpGpGpGpTpGpCpGpCpGpApCpGpApGOH (H2)
(16) HOGpCpGpCpApCpCpGpApGpApCpTpGOH (I1)
(17) HOCpTpApCpGpApTpApCpApCpApGpTpCpTpGOH (I2)
(18) HOGpTpApTpCpGpTpApGpGpApCpGpApApTpGOH (J1)
(19) HOGpApApApApCpApGpCpApTpTpCpGpTOH (J2)

(20) HOCpTpGpTpTpTpCpGpTpTpCpTpTpGOH (K1)
(21) HOGpGpApGpApTpCpGpCpApApGpApAp-COH (K2)
(22) HOCpGpApTpCpTpCpCpGpCpCpGpTpCpTOH (L1)
(23) HOTpApCpApTpTpTpCpCpApGpApCpGpGpCOH (L2)
(24) HOGpGpApApApTpGpTpApCpTpGpTpGpCpTOH (M1)
(25) HOTpTpCpApGpTpGpGpApGpCpApCpApGOH (M2)
(27) HOCpCpApCpTpGpApApGpCpCpApGpCpAOH (N1)
(28) HOGpCpGpGpApTpTpTpTpGpCpTpGpGpCOH (N2)
(29) HOApApApTpCpCpGpCpGpTpGpApTpApGOH (O1)
(30) HOGpApTpCpCpTpApTpCpApCOH (O2)

EXAMPLE 3

Synthesis of oligonucleotides (a1, a2, a3, a4, a5, a6, b1, b2, b3, b4, b5, b6, c1, c2, c3, c4, c5, c6, d1, d2, d3, d4, d5, d6, e1, e2, e3, e4, e5, 11, 12 and 13)

The following oligonucleotides were prepared using a procedure similar to that used for G1 described in Example 1.

(1) HOApApTpTpCpApTpGpTpGpTpTOH (a1)
(2) HOApCpTpGpCpCpApGpGpGpApCpCpCpApTOH (a2)
(3) HOApTpGpTpApApApApGpApApApGpCpApGOH (a3)
(4) HOTpGpGpCpApGpTpApApCpApCpApTpGOH (a4)
(5) HOTpTpTpApCpApTpApTpGpGpGpTpCpCOH (a5)
(6) HOApApGpGpTpTpTpTpCpTpGpCpTpTpCpTOH (a6)
(7) HOApApApApCpCpTpTpApApGpApApApTpAOH (b1)
(8) HOCpTpTpTpApApTpGpCpApGpGpTpCpAOH (b2)
(9) HOTpTpCpApGpApTpGpTpApGpCpGpGpAOH (b3)
(10) HOApTpTpApApApGpTpApTpTpTpCpTpTOH (b4)
(11) HOApTpCpTpGpApApTpGpApCpCpTpGpCOH (b5)
(12) HOTpTpCpCpApTpTpApTpCpCpGpCpTpApCOH (b6)
(13) HOTpApApTpGpGpApApCpTpCpTpTpTpCOH (c1)
(14) HOTpTpApGpGpCpApTpTpTpTpGpApApGOH (c2)
(15) HOApApTpTpGpGpApApApGpApGpGpApGOH (c3)
(16) HOTpGpCpCpTpApApGpApApApApGpApGOH (c4)
(17) HOTpCpCpApApTpTpCpTpTpCpApApApAOH (c5)
(18) HOCpTpGpTpCpApCpTpCpTpCpCpTpCpTpTOH (c6)
(19) HOApGpTpGpApCpApGpApApApApApTpAOH (d1)
(20) HOApTpGpCpApGpApGpCpCpApApApTpTOH (d2)
(21) HOGpTpCpTpCpCpTpTpTpApCpTpTOH (d3)
(22) HOCpTpCpTpGpCpApTpTpApTpTpTpTOH (d4)
(23) HOApGpGpApGpApCpApApTpTpTpGpGOH (d5)
(24) HOApApApGpCpTpTpGpApApGpTpApApAOH (d6)
(25) HOCpApApGpCpTpTpTpTpCpApApApApApAOH (e1)
(26) HOCpTpTpApApGpGpApTpGpApCpCpAOH (e2)
(27) HOGpApGpCpApTpCpCpApApApApGpApGOH (e3)
(28) HOCpTpTpApApApGpTpTpTpTpTpGpAOH (e4)
(29) HOGpGpApTpGpCpTpCpTpGpGpTpCpApTOH (e5)
(30) HOTpGpTpGpTpApApTpGpApTpApGOH (11)
(31) HOTpApCpApCpApCpTpCpTpTpTpTOH (12)
(32) HOGpApTpCpCpTpApTpCpApTOH (13)

EXAMPLE 4

Synthesis of oligonucleotides (m1, m2, LA, LB, LC and LD)

The following oligonucleotides (m1 and m2) were prepared using a procedure similar to that set out in Example 1.

(1) HOApGpCpTpTpGpApApGpTpApApApApCpApTpGOH (m1)
(2) HOApApTpTpCpApTpGpTpTpTpTpApCpTpTpCpAOH (m2)
(3) HOApGpCpTpTpGpApApGpTpApTpGpGOH (LA)
(4) HOGpApCpCpCpApTpApCpTpTpCpAOH (LB)
(5) HOApApTpTpCpGpGpGpCpCpCpGpCpGOH (LC)
(6) HOGpApCpCpCpGpCpGpGpGpCpCpGOH (LD)

EXAMPLE 5

Synthesis of oligonucleotides (A, B, C, D, E, F, G, H, I, J, K, L, M and N)

The following oligonucleotides were prepared using a procedure similar to that set out in Example 1.

(1) HOApApTpTpTpGpCpCpGpApCpAOH (A)
(2) HOCpGpTpTpApTpGpApTpGpTpCpGpGpCpAOH (B)
(3) HOTpCpApTpApApCpGpGpTpTpCpTpGpGpCOH (C)
(4) HOGpApApTpApTpTpTpGpCpCpApGpApApCOH (D)
(5) HOApApApTpApTpTpCpTpGpApApApTpGpAOH (E)
(6) HOTpCpApApCpApGpCpTpCpApTpTpTpCpAOH (F)
(7) HOGpCpTpGpTpTpGpApCpApApTpTpApApTpOH (G)
(8) HOGpTpTpCpGpApTpGpApTpTpApApTpTpGOH (H)
(9) HOCpApTpCpGpApApCpTpApGpTpTpApApCOH (I)
(10) HOGpCpGpTpApCpTpApGpTpTpApApCpTpAOH (J)
(11) HOTpApGpTpApCpGpCpApApApGpTpTpCpApCOH (K)

(12) HOCpTpTpTpTpTpApCpGpTpGpApApCpT-pTOH (L)
(13) HOGpTpApApApApApGpGpGpTpApTpC-pGOH (M)
(14) HOApApTpTpCpGpApTpApCpCOH (N)

EXAMPLE 6

Synthesis of oligonucleotides (SA, AB, SC, SD, SE, SF, SG, and SH)

(1) HOApApTpTpCpApTpGpGpCpTOH (SA)
(2) HOGpGpTpTpGpTpApApGpApApCpTpTpC-pTOH (SB)
(3) HOTpTpTpGpGpApApGpApCpTpTpTOH (SC)
(4) HOCpApCpTpTpCpGpTpGpTpTpGpApTpAp-GOH (SD)
(5) HOTpTpApCpApApCpCpApCpGpCpCpApTpGOH (SE)
(6) HOCpCpApApApApGpApApGpTpTpCOH (SF)
(7) HOCpGpApApGpTpGpApApApGpTpCpT-pTOH (SG)
(8) HOGpApTpCpCpTpApTpCpApApCpAOH (SH)

EXAMPLE 7

Preparation of the IGF-I gene

Aliquots of each oligonucleotides (A1-02) (0.4 nM) were phosphorylated with 4 units of T4 polynucleotide kinase (made by BRL) in 100 μl of a solution containing 74 mM Tris-HCl (pH 7.6), 10 mM DTT, 1.6 mM mercaptoethanol, 10 mM MgCl$_2$ and 0.5 mM ATP for 20 minutes at 37° C. After the reaction was completed, the enzyme in the reaction mixture was deactivated by incubation at 100° C. for 5 minutes. Ligation of the phosphorylated oligonucleotides was carried out as shown in FIG. 3 to give firstly ten fragments and ultimately the IGF-I gene for cloning. Ligations were carried out with T4 DNA ligase (7 units) in a solution containing 100 mM ATP (0. 5 μl) for 23 hours at 4° C. (standard conditions). The ligation products of oligonucleotides in each step were identified by staining with ethidium bromide following electroelution on a 2–16% gradient PAGE in Tris-EDTA buffer.

This process is shown in FIG. 3.

EXAMPLE 8

Molecular cloning of the IGF-I gene

Plasmid pBR322 was digested with BamHI and EcoRI restriction andonucleases. Reaction was terminated by heating at 65° C. for 5 minutes and the fragments separated by electrophoresis on a 0.8% agarose gel. The 3985 bp large fragment from pBR322 was recovered and ligated with 224bp IGF-I gene. The ligated mixture was transformed into E. coli HB101 by Kushner's method and ampicillin resistant transformants were selected on the plate containing tetracycline (25 μg/ml). Plasmid DNA isolated from one of five clones resistant to ampicillin and sensitive tetracycline was digested with EcoRI and BamHI and compared with appropriate size markers. The expected 224 bp IGF-I fragment was generated. This plasmid which was characterized by complete nucleotide sequencing cf the IGF-I gene was named pSdM1 and was used for the construction of expression plasmid.

This process is shown in FIG. 4.

EXAMPLE 9

Construction of the synthetic trp promoter II gene

Each oligonucleotides (B to SG) of block I', II', III' and IV' were phosphorylated with T4 polynucleotide kinase and then ligated with T4 DNA ligase as described above. These blocks (I' to IV') and unphosphorylated oligonucleotides (A and SH) were condensed successively. The last ligation product was purified by preparative 7.5% PAGE to give the 163 bp synthetic trp promoter II gene.

This process is shown in FIG. 5.

EXAMPLE 10

Cloning of the synthetic trp promoter II gene

The synthetic gene prepared in Example 11 was ligated with EcoRI, BamHI fragment of pBR322 and the ligation mixture was transformed into E. coli HB101. The plasmid obtained from the transformant of ampicillin resistant and tetracycline sensitive was digested with HpaI to confirm a band (4.1 kbp), and then digested with BamHI to confirm a band of 90 bp on PAGE. Moreover, the fragment of 56 bp by EcoRI-BamHI digestion was confirmed by comparison with size markers on PAGE. This plasmid was named pTrpEB7 and used for the construction of an expression plasmid.

This process is shown in FIG. 6.

EXAMPLE 11

Construction of IGF-I expression plasmid (pSdM1-322trp)

The plasmid pTrpEB7 was digested with EcoRI and BamHI to give a large fragment (4.1 kbp) by preparative agarose gel electrophoresis. This fragment was ligated with the IGF-I gene prepared from a plasmid pSdM1 prepared in Example 8. The ligated mixture was transformed into E. coli HB101 and ampicillin resistant transformants were selected. The obtained plasmid pSdM1-322trp was digested with EcoRI and BamHI to confirm the IGF-I gene (224bp) on 7.5% PAGE.

This process is shown in FIG. 9.

EXAMPLE 12

Sequencing of the IGF-I gene and of the synthetic trp promoter I gene

For the sequencing of the IGF-I gene and of the synthetic trp promoter I gene by the Maxam-Gilbert method, plasmid pSdM1-322trp was digested with EcoRI and treated with bacteria alkaline phosphatase at 37° C. for 1 hour. After phenol extraction and ethanol precipitation the plasmid was phosphorylated with T4 polynucleotide kinase in the presence of $\gamma$-$^{32}$P-ATP at 37° C. for 1 hour, and was finally digested with HinfI to afford two fragments (1100 bp, 480 bp). Each fragment was sequenced by the Maxam-Gilbert method. The resulting sequence of IGF-I and synthetic trp promoter I gene agreed with that designed.

EXAMPLE 13

Expression of the IGF-I gene

An overnight culture of E. coli F-3 (which is E. coli HB101 containing plasmid pSdM1-322trp) in L broth containing 20 μg/ml ampicillin was diluted 1 : 25 in M9 medium containing 0.2% glucose, 0.5% casamino acid (acid-hydrolyzed casein) and 50 μg/ml vitamin B1 . β-Indole acrylic acid was added to a final concentration of 10 μg/ml when A₆₀₀ was 0.4. Then the cells were incubated for 3 hours and collected by centrifugation (6 krpm, 4° C., 5 minutes). The cell were lysed by sonication and cleared of debris by centrifugation. The supernatants were mixed with 3M acetic acid. The precipitate was removed by centrifugation (20 krpm, 4° C., 10 minutes), and the supernatants were freeze-dried. For assay the sample was suspended in 4 ml of medium (0.01 M PBS, 0.025M EDTA, and 0.5% BSA) and adjusted at pH 7-8 with 0.1N NaOH. After removal of insoluble substance by centrifugation, the supernatants were stored at −20° C. until assay.

EXAMPLE 14

RIA of IGF-I:

The RIA of IGF-I was done by following the method established by N. Yanaihara. With 0.1 ml of the above sample or standard sample (IGF-I fragment (26-46)) sample buffer [0.5% BSA in 0.01M PBS, 0.025 M EDTA (pH 7.4) (0.4 ml)], rabbit antiserum (0.1 ml) of IGF-I (26-46) and $^{125}$I-IGF-I (26-46) (0.1 ml) were mixed. The mixture was allowed to stand for 48 hours at 4° C., and then added with rabbit serum (0.1 ml), rabbit γ-globulin antiserum (0.1 ml) and 5% PEG6000 (0.9 ml). After standing for additional 2 hours at 4° C. the pellet was collected by centrifugation (3 krpm, 4° C., 30 minutes). Radioactivity was measured by γ-counter. The content of IGF-I was calculated from this radioactivity.

EXAMPLE 15

Sequencing of the IGF-I gene in plasmid pSdM1

For the sequencing of IGF-I gene, plasmid pSdM1 was digested with EcoRI and then treated with AMV reverse transcriptase (purchased from Seikagaku Kogyo Co., Ltd.) in the presence of α-$^{32}$P-ATP at 37° C. for 30 minutes. The linear plasmid labeled with $^{32}$P was digested with BamHI to give two fragments (224 bp, 4.0 kbp). The smaller fragment (224 bp) was recovered by preparative polyacrylamide gel electrophoresis and sequenced by the Maxam-Gilbert method. On the other hand, plasmid pSdM1 was digested with BamHI firstly and then labeled with $^{32}$P as described above. The linear plasmid was digested with EcoRI to give two fragments (224 bp, 4.0 kbp). The smaller fragments (224 bp) was analyzed by the Maxam-Gilbert method as above. The results of sequencing from both side of the IGF-I gene agreed with the designed IGF-I gene.

EXAMPLE 16

Preparation of protein/peptide LH gene

Aliquots of each oligonucleotides (a2-12) (0.4 nM) were phosphorylated with 2.5 units of T4 polynucleotide kinase in 40 μl of a solution containing 50 mM Tris-HCl (pH 7.6), 20 mM DTT, 50 μg/ml BSA, 1 mM spermidine, 10 mM MgCl₂ and 2 mM ATP for 3 hours at 37° C. After the reaction was completed, the enzyme in the reaction mixture was deactivated by incubation at 100° C. for 5 minutes. Ligation of the phosphorylated oligonucleotides and two oligonucleotides (a1 and 13) was carried out as shown in FIG. 10 to give firstly six block fragments and ultimately protein/peptide LH gene (236 bp) for cloning. Ligation was carried out with T4 DNA ligase (5 units) in a solution containing 50 mM ATP (1 μl) for 5 hours at 16° C. The ligation products of the oligonucleotides in each step were identified by staining with ethidium bromide following electroelution on a 2-16% gradient PAGE in Tris-EDTA buffer.

This process is shown in FIG. 7.

EXAMPLE 17

Molecular cloning of protein/peptide LH gene

Protein/peptide LH gene (236 bp) which was synthesized as above was inserted into pBR322 using a procedure similar to that of Example 8. The plasmid (pLH107) obtained from E. coli HB101 transformant obtained was characterized by restriction enzyme analysis to have protein/peptide LH (236 bp).

This process is shown in FIG. 8.

EXAMPLE 18

Construction of protein/peptide LH expression plasmid (pLHtrp)

The plasmid pTrpEB7 prepared in Example 12 was digested with EcoRI and BamHI to give a large fragment (4.1 kbp) by preparative agarose gel electrophoresis. This fragment was ligated with protein/peptide LH gene prepared from a plasmid pLH107 by EcoRI and BamHI digestion. The ligated mixture was transformed into E. coli HB101 to give ampicillin resistant transformants. The plasmid (pLHtrp) obtained from the transformant was digested with EcoRI and BamHI to confirm protein/peptide LH gene (236 bp) on 7.5% PAGE.

This process is shown in FIG. 10.

EXAMPLE 19

Construction of the IGF-I expression plasmid pLHSdMmtrp

Plasmid pSdM1 was digested with EcoRI and BamHI to give IGF-I gene (224 bp). On the other hand, oligonucleotide (m2) prepared in Example 4 (2) was phosphorylated with T4 polynucleotide kinase as described in Example 7. The phosphorylated oligonucleotide, oligonucleotide m1 prepared in Example 4 (1) and IGF-I gene (224 bp) were mixed and treated with T4 ligase for 20 hours at 4° C. The ligation mixture was digested with BamHI and then purified by preparative PAGE to give the IGF-I gene with linker (242 bp). The gene (242 bp) was ligated with the fragment obtained from pLHtrp by HindIII-BamHI digestion, and then the ligation mixture was transformed into E. coli HB101. The E. coli HB101 containing plasmid pLHSdMmtrp was named E. coli F-6 and deposited with Fermentation Research Institute, Agency of Industrial Science and Technology (1-3, Higashi 1 chome Yatabe-machi Tsukuba-gun Ibaraki-ken 305, Japan) under deposit number of FERM P-7848 on September 17, 1984, and then converted to the Budapest Treaty with the same depository on February 28, 1985 under the new deposit number of FERM BP-729. The plasmid (pLHSdMmtrp) obtained from the transformant was digested with EcoRI and BamHI (198, 224 bp), HindIII and BamHI (242 bp), HpaI-BamHI (456 bp) to confirm the synthetic trp promoter I, protein/peptide LH and IGF-I gene on 7.5% PAGE.

This process is shown in FIG. 11.

EXAMPLE 20

Expression of a gene coding for IGF-I fused with protein/peptide LH (Type I) in E. coli F-6:

An overnight culture of E. coli F-6 (which is E. coli HB101 containing plasmid pLHSdMmtrp) (FERM BP-729) in L broth containing 50μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. β-Indole acrylic acid was added to a final concentration of 10μg/ml when $A_{600}$ was 0.5. Then the cells were incubated for 2 hours and collected by centrifugation (5 krpm, 4° C., 5 minutes).

EXAMPLE 21

Isolation and purification of IGF-I (1) Isolation and purification of fused IGF-I (Type I)

The wet cell paste (60 g) was suspended in 150 ml of 10 mM PBS-EDTA (pH 8.0) and cells were lysed by sonication. The cells debris was pelleted by centrifugation at 18,000 rpm for 30 minutes. The pellet was dissolved in 50 ml of 0.1 M Tris-HCl (pH 8.0)/8 M urea and 0.1 M dithiothreitol and centrifuged at 35,000 rpm for 30 minutes at 25° C. The supernatant was collected and applied to a Sephacryl S300 superfine column (5.0×86.6 cm; 1700 ml resin) equilibrated with 0.1 M Tris-HCl (pH 8.0)/8 M urea and 10 mM 2-mercaptoethanol. Elution was carried out at 4° C. with equilibration buffer, at a flow rate of 0.6 ml/min. Sephacryl S 300 chromatography was conducted and fractions of 17 ml were collected. Sephacryl S300 chromatography was conducted. Assays were performed immediately following fractionation for all chromatography steps. Active fractions were collected and the pooled fractions of 255 ml were dialyzed for 3 hours at room temperature against 8 liters of a 1 M acetic acid aqueous solution and then overnight against 8 liters of a fresh 1 M acetic acid aqueous solution. The fraction dialyzed was lyophilized to give fused IGF-I (Type I) (450) mg which contained the desired component. The fused IGF-I (Type I) shows a band at the position of molecular weight 15,500 on 15% SDS PAGE.

(2) Elimination of protein/peptide LH (Type I) from fused IGF-I (Type I) with cyanogen bromide The fused IGF-I (Type I) (225 mg) obtained by procedure (1) was dissolved in 36 ml of 60% formic acid. Cyanogen bromide (36 mg) was added and the mixture was allowed to react for 3 hours below 25° C. with stirring. After addition of 234 ml of distilled water, formic acid and cyanogen bromide were removed by lyophilization. The residue was dissolved in 36 ml of 1M Tris-HCl (pH 8.0)/8 M urea and 50 mM 2-mercaptoethanol. The resulting solution was dialyzed twice for 3 hours at room temperature against 400 ml of 0.01 M AcONH$_4$ (pH 4.6)/8 M urea and 50 mM 2-mercaptoethanol (Buffer A) and then overnight against 400 ml of fresh Buffer A. The dialyzed solution was applied to a cationic ion exchange resin CM 52 column (1.6×7.5 cm; 15 ml resin) equilibrated with Buffer A. The column was washed with Buffer A (60 ml) at room temperature at a flow rate of 0.25 ml/min and eluted with a linear gradient from Buffer A (120 ml) to 0.2 M AcONH$_4$/8 M urea and 50 mM 2-mercaptoethanol (120 ml). Fractions (from No. 57 to No. 100) of 2.9 ml were collected.

(3) High performance liquid chromatography

The pooled fraction obtained by procedure (2) was subjected to HPLC.
column: Beckman Ultrapore RPSC (4.6×75 mm)
flow rate: 1 ml/min
elution: linear gradient from 10% to 60 % acetonitrile in 0.01 M trifluoroacetic acid over 50 minutes.

Figure 16:
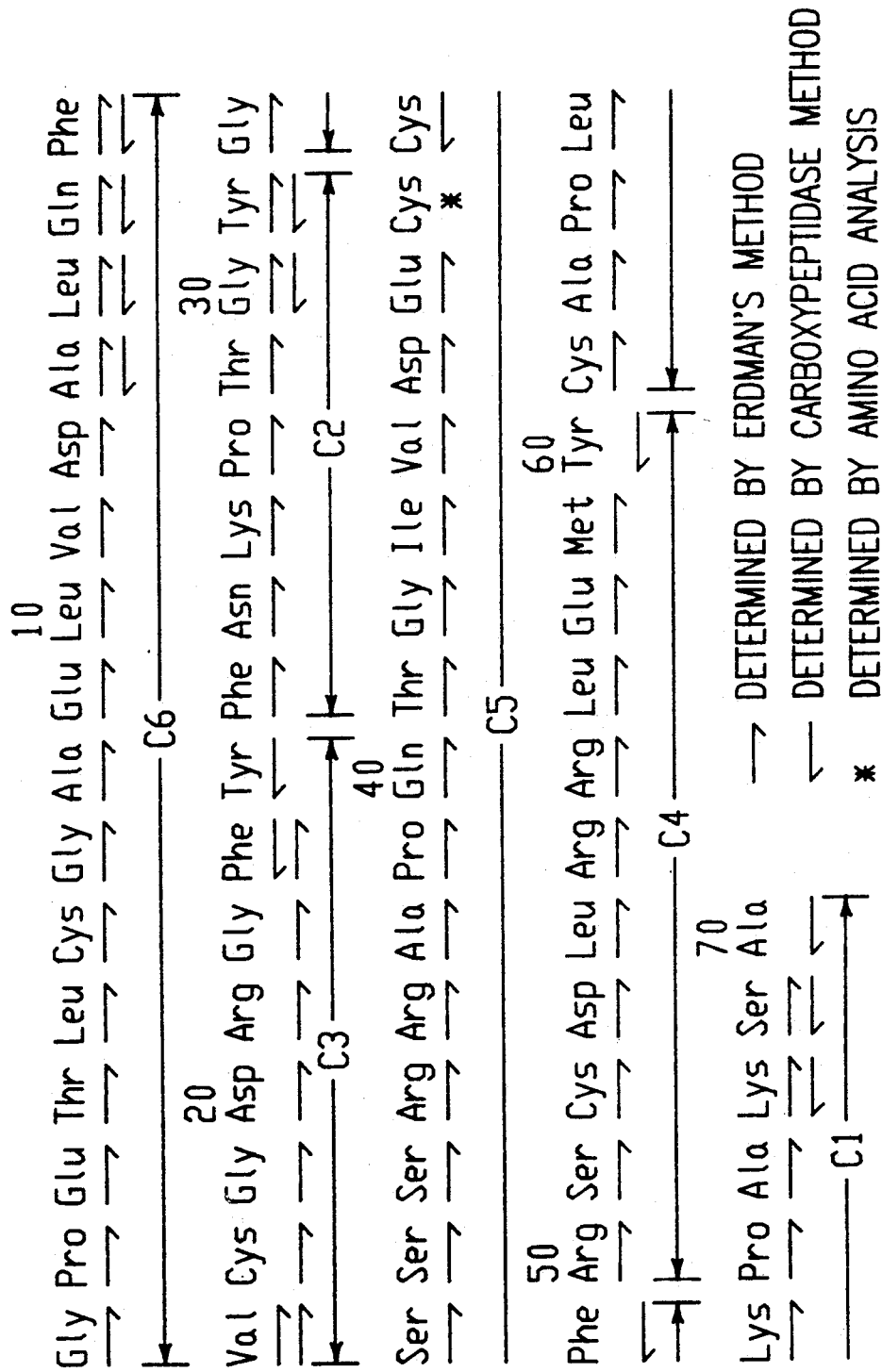
FIG. 16 sets forth the amino acid analysis and sequence analysis of IGF-I.

The chromatography was repeated 15 times and fractions containing reduced IGF-I were collected and the main peak with a retention time of 29.32 minutes corresponds to reduced IGF-I. The thus reduced IGF-I was obtained in an amount of about 2.4 mg by the procedure described above. The reduced IGF-I was converted to oxidized IGF-I by the usual manner of refolding. This IGF-I was identical with authentic IGF-I (gift of Dr. Humbel) on HPLC. (4) Amino acid analysis and sequence analysis of IGF-I:

The amino acid composition of IGF-I was obtained using a Walters amino acid analysis system. The amino acid sequence of IGF-I was determined by the combination of Edman's method (DIBITC method) [J. Y. Chang et al: Biochem. J., 153, 607(1976), Biochim. Biophys. Acta., 578, 188(1979)] and the carboxypeptidase method as shown in FIG. 16.

EXAMPLE 22

Construction of IGF-I expression plasmid pLHSdMwtrp

Plasmid pSdM1 was digested with EcoRI and BamHI to give IGF-I gene (224 bp), which was digested with AvaII. The larger fragment (215 bp) was recovered by preparative PAGE. On the other hand, oligonucleotide (LB) prepared in Example 4 (4) was phosphorylated with T4 polynucleotide kinase as described in Example 7. The phosphorylated oligonucleotide, oligonucleotide LA prepared in Example 4 (3) and the IGF-I fragment (215 bp) prepared as above were mixed and treated with T4 ligase for 20 hours at 4° C. The ligation mixture was digested with BamHI and then purified by preparative PAGE to give IGF-I gene with linker (230 bp). The IGF-I gene with linker (230 bp) was ligated with the fragment obtained from PLHtrp by HindIII and BamHI digestion, and then the ligation mixture was transformed into E. coli HB 101. The plasmid (pLHSdMwtrp) obtained from the transformant was digested with EcoRI and BamHI (416 bp), EcoRI and PstI (859 bp), HindIII and BamHI (230 bp) to confirm this plasmid gene on 7.5% PAGE. The E. coli HB101 containing plasmid pLHSdMwtrp was named E. coli F-7.

This process is shown in FIGS. 12(a), 12(b) and 12(c).

EXAMPLE 23

Expression of a gene coding for IGF-I fused with protein/peptide LH (Type II) in E. coli F-7

An overnight culture of E. coli F-7 (which is E. coli HB101 containing plasmid pLHSdMwtrp) in L broth containing 50 μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. β-Indole acrylic acid was added to a final concentration of 10 μg/ml when A600 was 0.5. Then the cells were incubated for 2 hours and collected by centrifugation (5 krpm, 4° C., 5 minutes).

EXAMPLE 24

Isolation and purification of IGF-I (1) Isolation and purification of IGF-I fused with protein/peptide LH (Type II)

The wet cell paste (60 g) was suspended in 150 ml of 10 mM PBS-EDTA (pH 8.0) and cells were lysed by sonication. The cell debris was pelleted by centrifugation at 18,000 rpm for 30 minutes. The pellet was dissolved in 50 ml of 0.1 M Tris HCl (pH 8.0)/8 M urea and 0.1 M dithiothreitol and centrifuged at 40,000 rpm for 30 minutes at 20° C. The supernatant was collected and applied to a Sephacryl S 300 superfine column (5.0×86.6 cm; 1,700 ml resin) equilibrated with 0.1 M Tris HCl (pH 8.0)/8 M urea and 10 mM 2-mercaptoethanol. Elution was carried out at 4° C. with an equilibration buffer at a flow rate of 0.6 ml/ml. Sephacryl S 300 chromatography was conducted and fractions of 17 ml were collected. Assays were performed immediately following fractionation for all chromatography steps. Active fractions were collected and the pooled fractions of 204 ml were dialyzed for 3 hours at room temperature against 8 liters of a 1 M acetic acid aqueous solution and then overnight against 8 liters of a fresh 1 M acetic acid aqueous solution. The fraction dialyzed was lyophilized to give fused IGF-I (Type II) (450mg) which contains the desired component. The crude fused IGF-I (Type II) was purified by reverse phase HPLC (ultrapore RPSC column) using a linear gradient of 10% $CH_3CN$ (0.01 M TFA) to 60% $CH_3CN$ (0.01 M TFA) to give the purified fused IGF-I (Type II).

(2) Elimination of protein/peptide LH (Type II) from the fused IGF-I (Type II)

(a) Elimination of protein/peptide LH (Type II) from fused IGF-I (Type II) with BNPS-skatole The fused IGF-I (Type II) (830 μg) was treated with BNPS-skatole (297 μg) in 70% acetic acid at 0° C. for 3 hours. To the reaction mixture 2-mercaptoethanol (120 μl) was added, and then the solvent was evaporated *in vacuo*. The residue was dissolved in 6 M guanidine, 50 mM Tris HCl buffer (2 ml) and washed $CHCl_3$ (2 ml). The aqueous layer was treated with 2-mercaptoethanol (200 μl) and then purified by reverse phase HPLC (RPSC column) to give a IGF-I sulfoxide (50 μg).

(b) Elimination of protein/peptide LH (Type II) from fused IGF-I (Type II) with NCS in urea The fused IGF-I (Type II) (71 μg) was treated with NCS (6.6 μg) in a mixture of acetic acid (1 ml), urea (1 g) and water (2 ml) at 0° C. for 24 hours. The reaction mixture was neutralized with Tris, treated with 2-mercaptoethanol (20 ml), and then purified by reverse phase HPLC (RPSC column) to give IGF-I sulfoxide (4.2 μg).

(3) Reduction of IGF-I sufoxide with thioglycolic acid

IGF-I sulfoxide (17 μg) in a solution (400 ml) of 5 M thioglycolic acid and 6 M urea was allowed at 50° C. for 3.5 hours. After addition of 6M guanidine (1 ml) and 2-mercaptoethanol (100 μl), the mixture was adjusted to a pH of 8.0 with Tris, and then purified by reverse phase HPLC (RPSC column) to give a pure reduced IGF-I (7 μg).

EXAMPLE 25

Construction of IGF-I expression plasmid pLHSdMctrp

The plasmid pSdM1 was digested with AvaII to give the gene (640 bp) containing IGF-I gene, which was digested with BamHI and the larger fragment (215 bp) was recovered by preparative PAGE. On the other hand, oligonucleotides (LC and LD) prepared in Examples 4(5) and 4(6), were phosphorylated with T4 polynucleotide kinase as described in Example 7. The phosphorylated oligonucleotides and the IGF-I fragment (215 bp) prepared as above were mixed and treated with T4 DNA ligase for 24 hours at 4° C. The ligation mixture was digested with EcoRI and BamHI, and then purified by preparative PAGE to give IGF-I gene (230 bp) with linker. The IGF-I gene (230 bp) was ligated with the fragment (4 kbp) obtained from pBR322 by EcoRI and BamHI digestion, and then the ligation mixture was transformed into *E. coli* DH1. The plasmid pSdMc obtained from the transformant was digested with EcoRI and BamHI (230 bp) to confirm this plasmid gene on 7.5% PAGE. The plasmid pSdMc was digested with EcoRI and BamHI, the smaller fragment (230 bp) was recovered by preparative PAGE. On the other hand, oligonucleotide (m2) prepared in Example 4 (2) was phosphorylated with T4 polynucleotide kinase as described in Example 7. The phosphorylated oligonucleotide, oligonucleotide m1 prepared in Example 4 (1) and IGF-I gene (230 bp) were mixed and treated with T4 ligase for 20 hours at 4° C. The ligation mixture was digested with BamHI and then purified by preparative PAGE to give IGF-I gene with linker (248 bp). The gene (248 bp) was ligated with the fragment obtained from pLHtrp by HindIII-BamHI digestion, and then the ligation mixture was transformed into *E. coli* HB101. The *E. coli* HB101 containing plasmid pLHSdMctrp was named *E. coli* F-8. The plasmid (pLHSdMctrp) obtained from the transformant was digested with EcoRI and BamHI (198, 230 bp), HindIII and BamHI (248 bp), HpaI-BamHI (456 bp) to confirm the synthetic trp promoter I, protein/peptide LH and IGF-I gene on 7.5% PAGE.

This process is shown in FIGS. 13(A), 13(B) and 13(C).

EXAMPLE 26

Expression of a gene coding for IGF-I fused with protein/peptide LH (Type III)

An overnight culture of *E. coli* F-8 (which is *E. coli* HB101 containing plasmid pLHSdMctrp) in L broth containing 50μg/ml ampicillin was diluted 1:20 in M9 medium containing 0.2% glucose, 0.5% casamino acid (acid-hydrolyzed casein), 50 μg/ml vitamin B1 and 25 μg/ml ampicillin. β-Indole acrylic acid was added to a final concentration of 10μg/ml when $A_{600}$ was 0.5. Then the cells were incubated for 2 hours and collected by centrifugation (5 krpm, 4° C., 5 minutes).

EXAMPLE 27

Isolation and purification of IGF-I (1) Isolation and purification of IGF-I fused with protein/peptide LH (Type III)

The wet cell paste (60 g) was suspended in 150 ml of 10 mM PBS-EDTA (pH 8.0) and cells were lysed by sonication. The cell debris was pelleted by centrifugation at 18,000 rpm for 30 minutes. The pellet was dissolved in 50 ml of 0.1 M Tris HCl (pH 8.0)/8 M urea and 0.1 M dithiothreitol and centrifuged at 40,000 rpm for 30 minutes at 20° C. The supernatant was collected and applied to a Sephacryl S 300 superfine column (5.0×86.6 cm; 1,700 ml resin) equilibrated with 0.1 M Tris HCl (pH 8.0)/8 M urea and 10 mM 2-mercaptoethanol. Elution was carried out at 4° C. with equilibration buffer at a flow rate of 0.6 ml/ml. Sephacryl S 300 chromatography was conducted and fractions of 17 ml were collected. Assays were perform immediately following fractionation for all chromatography steps. Active fractions were collected and the pooled fractions of 204 ml were dialyzed for 3 hours at room temperature against 8 liters of a 1 M acetic acid aqueous solution and then overnight against 8 liters of fresh 1 M acetic acid aqueous solution. The fraction dialyzed was lyophilized to give fused IGF-I (Type III) of (450mg) which contained the desired component. The crude fused IGF-I (Type III) was purified by reverse phase HPLC (ultrapore RPSC column) using a linear gradient of 10% $CH_3CN$ (0.01 M TFA) to 60% $CH_3CN$ (0.01 M TFA) to give a purified fused IGF-I (Type III).

(2) Elimination of protein/peptide LH (Type III) from the fused IGF-I (Type III) with collagenase The solution of fused IGF-I (Type III) (25 µg) in 8 M urea or 8 M guanidine HCl was diluted with water until 2.4 M (urea) or 2 M (Guanidine HCl). To the solution 500 mM Tris-HCl, 100 mM $CaCl_2$ and 200 mM acetic acid were added and the solution was adjusted at pH 7.2 with 1N HCl, and then 0.1 mM diisopropyl fluorophosphate and collagenase (10 mg) were added. The mixture was gently stirred at 30° C. for 18 hours. The reaction was stopped by addition of guanidine HCl until final concentration of 8M. After addition of DTT (100 mM/ml), the mixture was analyzed by HPLC. (Column: Beckman Ultrapor RPSC; Flow rate: 1 ml/ min; Elution: linear gradient from 10% to 60% acetonitrile in 0.01 M TFA over 50 minutes) to detect a peak corresponding to reduced IGF-I.

EXAMPLE 28

Construction of plasmid pUC-SS1

The expression plasmid of IGF-I fused with protein/peptide LH (pLHSdMmtrp) (100 µg) was digested with HpaI (180 units) at 37° C. for 1 hour in HpaI digestion buffer. After a detection of the complete digestion on 0.8% agarose gel, 1M NaCl and PstI (180 units) were added to the mixture, and the mixture was incubated at 37° C. for 1 hour to give two fragments (3.7 kbp and 0.8 kbp). The large fragment (3.7 kbp) was separated on 0.8% agarose gel, purified by DEAE-TOYOPEARL 650M (anion exchange resin having diethylaminoethyl groups, made by Toyo Soda Manufacturing Co., Ltd.) column chromatography, followed by ethanol precipitation to give a HpaI-PstI digested fragment (3.7 kbp) (40 µg). The fragment (35 µg) was partially digested with HincII (63 units) in HincII buffer at 37° C. for 18 minutes to give six fragments (3690, 3417, 2958, 732, 459 and 273 bp). The fragment (2 µg) of 732 bp was purified by preparative 0.8% agarose gel electrophoresis and DEAE TOYOPEARL 650M column chromatography.

Figure 14B:
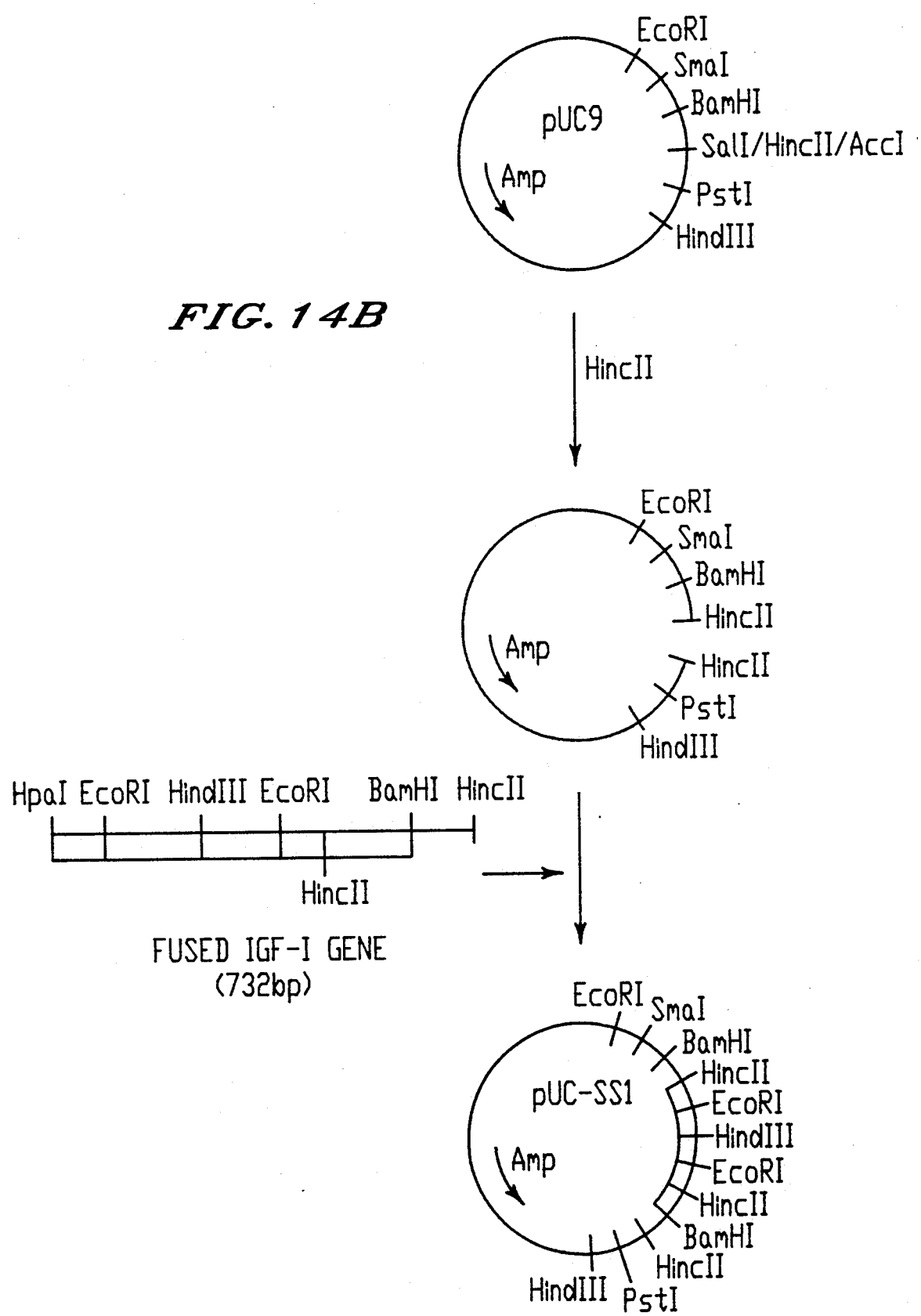
FIGS. 14A & B illustrate the construction of plasmid pUC-SS1.

On the other hand, plasmid pUC9 (purchased from Pharmacia) (10 µg) was digested with HincII (120 units) at 37° C. for 1 hour to give a pUC9 HincII linear fragment (2 µg). This DNA (1.9 µg) was incubated with calf intestinal alkaline phosphatase (hereinafter referred to as CIP) (purchased from Boehringer Mannheim) (20 units) for 30 minutes at 37° C. and then with additional CIP (20 units) for 30 minutes at 37° C. After inactivation of the enzyme by heating for 15 minutes at 65° C., the DNA was purified by phenol-chloroform extraction, followed by Sephadex G-50 superfine spun column chromatography and ethanol precipitation to give 1.5 µg of dephosphorylated, HincII digested linear fragment of pUC9. The DNA (1.2 µg) was ligated with HpaI-HincII digested linear fragment (732 bp) prepared above containing IGF-I fused with protein/peptide LH gene in the presence of T4 DNA ligase (8 units) for 20 hours at 16° C. The ligation mixture was transformed into E. coli MM 294 to give many ampicillin resistant colonies. One of the 22 colonies was the desired plasmid pUC-SS1 which was confirmed by restriction endonuclease analysis with PstI (3.4 kbp) and BamHI (2.9 kbp and 0.45 kbp). This process is shown in FIGS. 14(a) and 14(b).

EXAMPLE 29

Construction of expression plasmid pLS-T2 and pLS-T3

Plasmid pLHSdMmtrp (50 µg) was digested with BamHI (120 units) for 1 hour at 37° C. in BamHI digestion buffer, followed by preparative 0.8% agarose gel electrophoresis to give 20 µg of linear fragment (4.5 kbp). This DNA (16 µg) was treated with CIP to afford dephosphorylated, BamHI digested linear fragment of pLHSdMmtrp (4 µg).

On the other hand pUC-SS1 (10 µg) was digested with BamHI (60 units) to give two fragments (2.6 kbp and 464 bp). The small fragment (464 bp) was purified by preparative 0.8% agarose gel electrophoresis. The obtained BamHI digested fragment (464 bp) (36 ng) and the above dephosphorylated, BamHI digested linear fragment of pLHSdMmtrp (200 ng) were incubated in the presence of T4 DNA ligase (4 units) for 20 hours at 16° C. E. coli HB101 was transformed with the ligation mixture to give the ampicillin resistant colonies. Seven of twelve colonies were plasmid having two cistron IGF-I fused with protein/peptide LH gene (which is named pLS-T2) and one of them was plasmid having three cistron IGF-I gene fused with protein/peptide LH gene (which is named pLS-T3), which were confirmed by restriction endonuclease analysis (pLS-T2: PstI-PvuII (1.5, 3.4 kbp), EcoRI (198, 266 bp), PstI-SalI (3.0, 2.0 kbp) HpaI (4.98 kbp); pLS-T3: PstI-PvuII (1.5, 3.9 kbp), EcoRI (198, 266 bp), PstI-SalI (3.0, 2.5 kbp), HpaI (5.45 kbp).

Figure 15A:
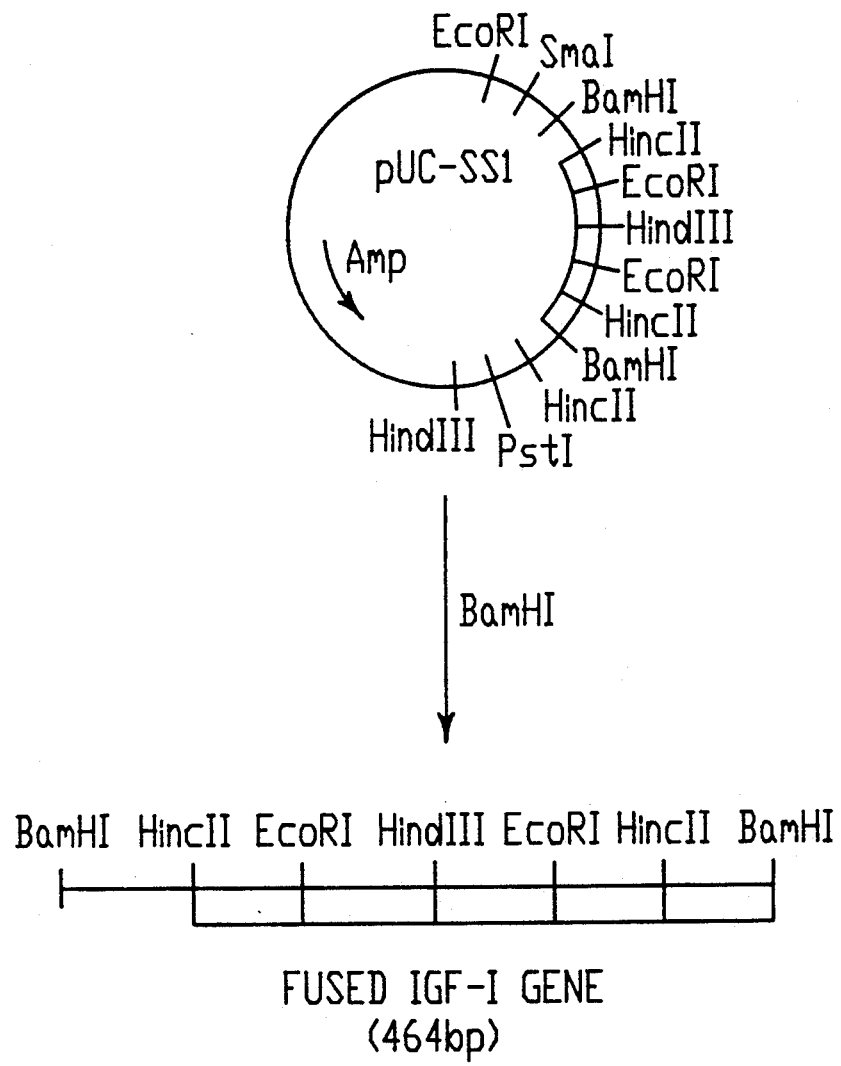
FIGS. 15A, B, & C illustrate the construction of plasmid pLS-T2 and pLS-T3.
Figure 15B:
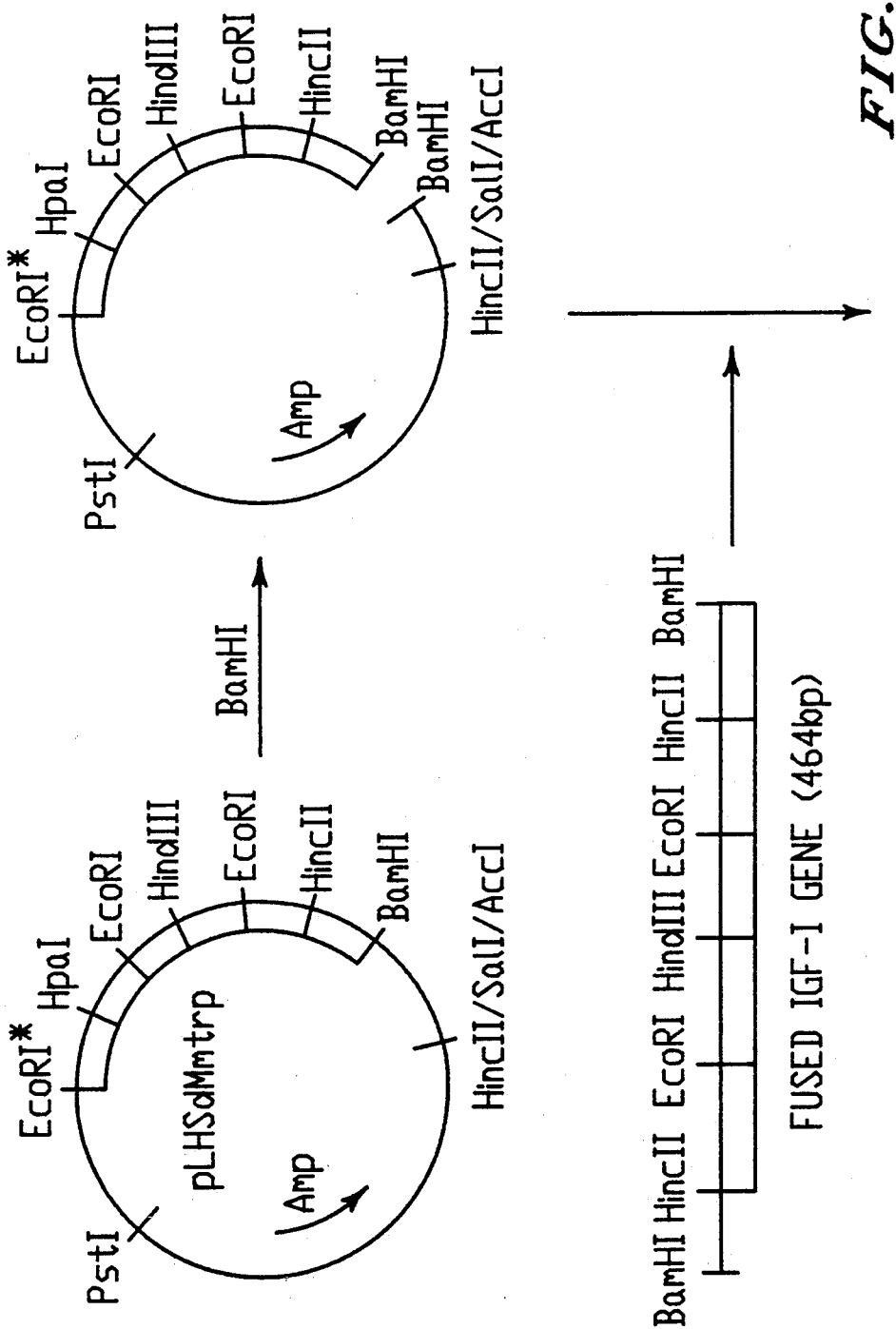
Figure 15C:
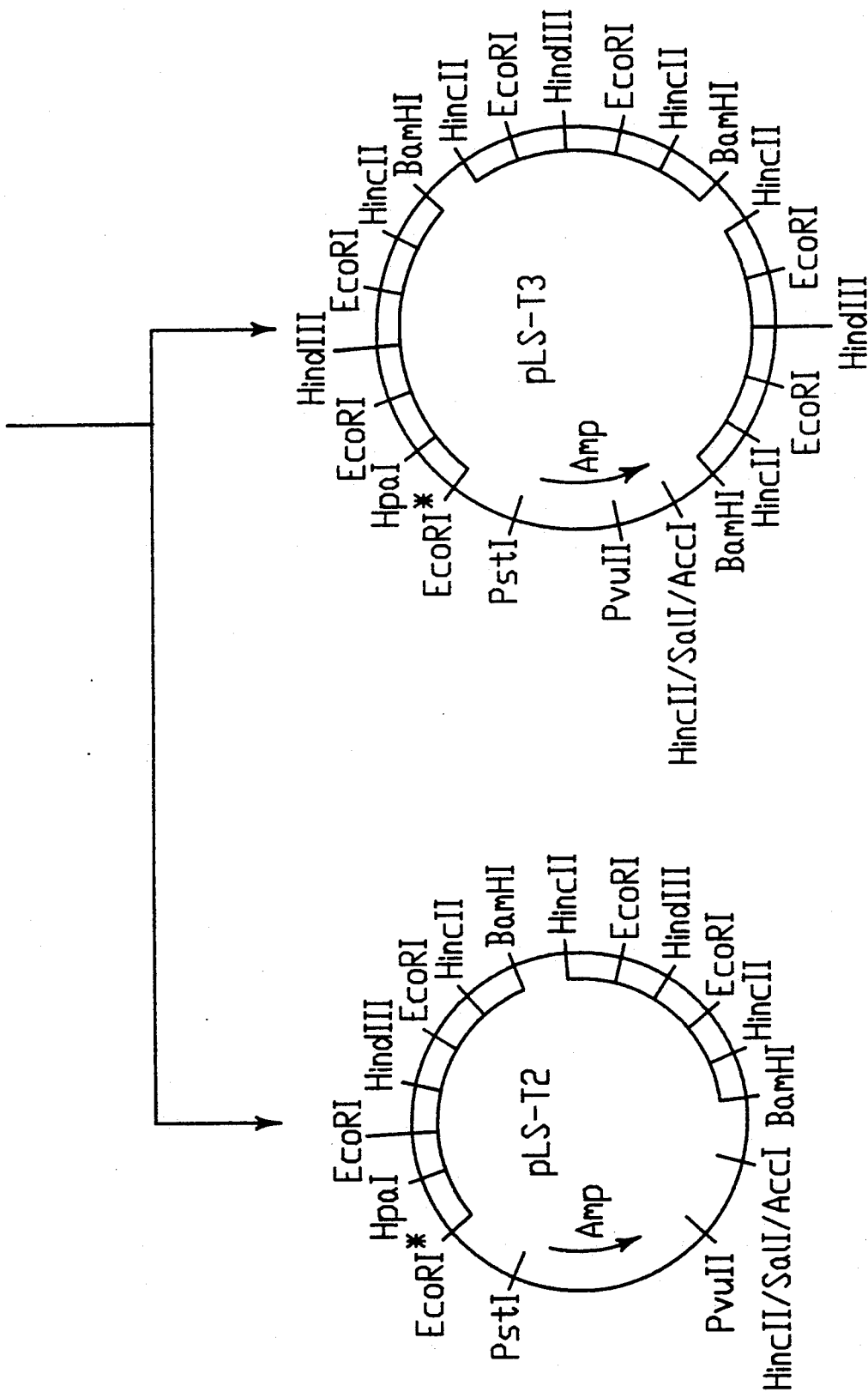

This process is shown in FIGS. 15(a), 15(b) and 15(c).

The E. coli HB101 containing plasmid pLS-T2 was named E. coli F-10 and the E. coli HB101 containing plasmid pLS-T3 was named E. coli F-11.

EXAMPLE 30

Expression of a gene coding for IGF-I fused with protein/peptide LH in E. coli F-10

An overnight culture of E. coli F-10 (which is E. coli HB101 containing plasmid PLS-T2) in L broth containing 50µg/ml ampicillin was diluted 1:20 in M9 medium containing 0.2% glucose, 0.5% casamino acid (acid-hydrolyzed casein), 50 µg/ml vitamin B1 and 25 g/ml ampicillin. β-Indole acrylic acid was added to a final concentration of 10µg/ml when $A_{600}$ was about 0.5. Then the cells were incubated and aliquots (20 ml of culture broth) were collected by centrifugation (7 krpm, 4° C., 5 minutes).

EXAMPLE 31

Expression of a gene coding for IGF-I fused with protein/peptide LH in E. coli F-11

An overnight culture of E. coli F-11 (which is E. coli HB101 containing plasmid pLS-T3) in L broth containing 50µg/ml ampicillin was diluted 1:20 in M9 medium containing 0.2% glucose, 0.5% casamino acid (acid-hydrolyzed casein), 50 µg/ml vitamin B1 and 25 µg/ml ampicillin. β-Indole acrylic acid was added to a final concentration of 10μg/ml when A600 was about 0.5. Then the cells were incubated and aliquots (20 ml of culture broth) were collected by centrifugation (7 krpm, 4° C., 5 minutes).

EXAMPLE 32

Isolation and purification of IGF-I fused with protein/peptide LH

E. coli F-11 was cultured for 4 hours after induction and collected by centrifugation (14 krpm, 4° C.). Wet cell paste (120 g: from 20 liter culture broth) was suspended in 300 ml of 10 mM PBS-10 mM EDTA (pH 8.0) and freezed at −80° C. The mixture was thawed and added to 50 ml of 0.5 M EDTA and 50 ml of 10 mg/ml lisozyme solution. After stirring for 1 hour at 0° C., the mixture was homogenized. The cell debris was suspended in 2 liter of 25 mM PBS-10 mM EDTA-0.5% sodium sarcosyl (pH 8.0), and then the mixture was homogenized. After stirring for 1 hour at 0° C., the mixture was centrifuged at 7,000 rpm for 35 minutes at 4° C. The pellet was suspended in 1 liter of 10 mM PBS-10 mM EDTA (pH 8.0). The mixture was homogenized and centrifuged using the above method. The pellet was dissolved in 200 ml of 6 M guanidine hydrochloride-100 mM Tris chloride-10mM EDTA-100 mM DTT (pH 8.0), and centrifuged at 40 krpm for 1 hour at 20° C. The supernatant was collected and applied to a Sephacryl S300 superfine column (5.0×86.6 cm; 1700 ml resin) equilibrated with 0.1 M Tris-HCl (pH 8.0)/8 M urea and 10 mM 2-mercaptoethanol. Elution was carried out at 4° C. with equilibration buffer, at a flow rate of 0.6 ml/min. Sephacryl S 300 chromatography was conducted and fractions of 35 ml were collected. Sephacryl S300 chromatography was conducted. Assays were performed immediately following fractionation for all chromatography steps. Active fractions were collected and the pooled fraction of 500 ml was dialyzed for 3 hours at room temperature against 16 liters of a 1 M acetic acid aqueous solution and then overnight against 16 liters of a fresh 1 M acetic acid aqueous solution. The fraction dialyzed was lyophilized to give IGF-I fused with protein/peptide LH (1.26 g) which contains a desired component. The IGF-I fused with protein/peptide LH showed a band at a position of molecular weight 15,500 on 15% SDS PAGE.

EXAMPLE 33

The content of IG-I fused with protein/peptide LH in culture fluid was assayed using RIA and calculated as the content of IGF-I:

RIA of IGF-I was followed the method established by N. Yanaihara.

Method

With 0.1 ml of the above sample or standard sample (IGF-I fragment (26-46)) sample buffer [0.5% BSA in 0.01M PBS, 0.025 M EDTA (pH 7.4) (0.4 ml)], rabbit antiserum (0.1 ml) of IGF-I (26-46) and $^{125}$I-IGF-I (26-46) (0.1 ml) were mixed. The mixture was allowed to stand for 48 hours at 4° C., and then added with rabbit serum (0.1 ml), rabbit γ-globulin antiserum (0.1 ml) and 5% PEG6000 (0.9 ml). After standing for additional 2 hours at 4° C. the pellet was collected by centrifugation (3 krpm, 4° C., 30 minutes). Redistribution was measured by γ-counter. The content of IGF-I was calculated from this radioactivity.

Results

The culture fluid (20 ml) (culture broth of E. coli F-10 and E. coli F-11 in M9-broth) which was prepared by the method described in Example 2 and Example 3, respectively, was centrifuged at 7,000 rpm. The obtained cells were suspended in 8M urea, 10 mM EDTA (pH 8.0) (2 ml) and then opened by sonication. The suspended solution was centrifuged (18,000 rpm, 30 minutes, 4° C.), the supernatant was diluted with 0.5% BSA, 10 mM PBS, 25 mM EDTA to use as RIA and HPLC sample.

The content of IGF-I was compared to that of culture fluid similarly prepared using E. coli F-6 which contained expression plasmid pLHSdMmtrp (which was prepared by the method described in European Patent Application No. 85103060.1 filed on Mar. 16, 1985).

| Culture fluid (expression plasmid) | Culture time (hour) | | | |
|---|---|---|---|---|
| | 1 | 2 | 3 | 4 |
| | (IGF-I μg/ml culture fluid) | | | |
| pLHSdMmtrp | 3.5 | 7.7 | 12.0 | 15.0 |
| pLS-T2 | 3.9 | 9.3 | 14.3 | 16.0 |
| pLS-T3 | 6.7 | 10.8 | 15.6 | 20.6 |

What we claim is:

1. A polycistronic gene encoding IGF-I fused to a protective protein or peptide, wherein said protective protein or peptide (i) is a protein or a peptide having a methionine residue as its carboxy-terminal amino acid, (ii) is fused to IGF-I through said methionine residue, and (iii) protects said IGF-I from degradation by proteases in cells of E. coli.

2. An expression plasmid containing a promoter and the gene of claim 1.

3. E. coli containing the expression plasmid of claim 2.

4. A process for the production of IGF-I fused to a protective protein or peptide which comprises:
   (a) culturing E. coli containing an expression plasmid containing a promoter and a polycistronic gene, said polycistronic gene encoding IGF-I fused to a protective protein or peptide, wherein said protective protein or peptide (i) is a protein or a peptide having a methionine residue as its carboxy-terminal amino acid, (ii) is fused to IGF-I through said methionine residue, and (iii) protects said IGF-I from degradation by proteases in cells of E. coli, and
   (b) recovering IGF-I fused to said protective protein or peptide from the culture.

5. A polycistronic gene, encoding IGF-I fused to a protective protein or peptide comprising the following amino acid sequence:

1         10
Cys—Tyr—Cys—Gln—Asp—Pro—Tyr—Val—Lys—Glu—Ala—Glu—Asn—Leu—

20
Lys—Lys—Tyr—Phe—Asn—Ala—Gly—His—Ser—Asp—Val—Ala—Asp—Asn—

-continued

```
                30                                      40
Gly—Thr—Leu—Phe—Leu—Gly—Ile—Leu—Lys—Asn—Trp—Lys—Glu—Glu—

50
Ser—Asp—Arg—Lys—Ile—Met—Gln—Ser—Gln—Ile—Val—Ser—Phe—Tyr—

60                              70
Phe—Lys—Leu—Glu—Val—Lys—His—Glu—Phe—Met—Gly—Pro—Glu—Thr—

80
Leu—Cys—Gly—Ala—Glu—Leu—Val—Asp—Ala—Leu—Gln—Phe—Val—Cys—

90
Gly—Asp—Arg—Gly—Phe—Tyr—Phe—Asn—Lys—Pro—Thr—Gly—Tyr—Gly—

100                             110
Ser—Ser—Ser—Arg—Arg—Ala—Pro—Gln—Thr—Gly—Ile—Val—Asp—Glu—

120
Cys—Cys—Phe—Arg—Ser—Cys—Asp—Leu—Arg—Arg—Leu—Glu—Met—Tyr—

130
Cys—Ala—Pro—Leu—Lys—Pro—Ala—Lys—Ser—Ala
```

6. An expression plasmid containing a promoter and the gene of claim 5.

7. *E. coli* containing the expression plasmid of claim 6.

8. A process for the production of IGF-I fused to a protective protein or peptide which comprises:
 (a) culturing *E. coli* containing an expression plasmid containing a promoter and a polycistronic gene, wherein said polycistronic gene encodes said IGF-I fused to said protective protein or peptide comprising the following amino acid sequence:

```
  1                                          10
Cys—Tyr—Cys—Gln—Asp—Pro—Tyr—Val—Lys—Glu—Ala—Glu—Asn—Leu—

20
Lys—Lys—Tyr—Phe—Asn—Ala—Gly—His—Ser—Asp—Val—Ala—Asp—Asn—

30                                      40
Gly—Thr—Leu—Phe—Leu—Gly—Ile—Leu—Lys—Asn—Trp—Lys—Glu—Glu—

50
Ser—Asp—Arg—Lys—Ile—Met—Gln—Ser—Gln—Ile—Val—Ser—Phe—Tyr—

60                                      70
Phe—Lys—Leu—Glu—Val—Lys—His—Glu—Phe—Met—Gly—Pro—Glu—Thr—

80
Leu—Cys—Gly—Ala—Glu—Leu—Val—Asp—Ala—Leu—Gln—Phe—Val—Cys—

90
Gly—Asp—Arg—Gly—Phe—Tyr—Phe—Asn—Lys—Pro—Thr—Gly—Tyr—Gly—

100                             110
Ser—Ser—Ser—Arg—Arg—Ala—Pro—Gln—Thr—Gly—Ile—Val—Asp—Glu—

120
Cys—Cys—Phe—Arg—Ser—Cys—Asp—Leu—Arg—Arg—Leu—Glu—Met—Tyr—

130
Cys—Ala—Pro—Leu—Lys—Pro—Ala—Lys—Ser—Ala;
``` and (b) recovering IGF-I fused to said protective protein or peptide from the culture.

* * * * *